US008846352B2

(12) United States Patent
Chua et al.

(10) Patent No.: US 8,846,352 B2
(45) Date of Patent: Sep. 30, 2014

(54) GENETICALLY ENGINEERED MICROORGANISMS THAT METABOLIZE XYLOSE

(75) Inventors: Penelope Chua, San Francisco, CA (US); Aravind Somanchi, Redwood City, CA (US)

(73) Assignee: Solazyme, Inc., South San Francisco, CA (US)

( * ) Notice: Subject to any disclaimer, the term of this patent is extended or adjusted under 35 U.S.C. 154(b) by 39 days.

(21) Appl. No.: 13/464,948

(22) Filed: May 4, 2012

(65) Prior Publication Data

US 2012/0329109 A1 Dec. 27, 2012

Related U.S. Application Data

(60) Provisional application No. 61/483,550, filed on May 6, 2011, provisional application No. 61/497,501, filed on Jun. 15, 2011.

(51) Int. Cl.
| | | |
|---|---|---|
| C12P 7/64 | (2006.01) |
| C12N 1/12 | (2006.01) |
| C12P 21/06 | (2006.01) |
| C12P 19/34 | (2006.01) |
| C12N 15/00 | (2006.01) |
| A23D 9/00 | (2006.01) |
| C07H 21/04 | (2006.01) |
| C07K 14/00 | (2006.01) |
| C12N 1/22 | (2006.01) |

(52) U.S. Cl.
CPC ... *C12P 7/64* (2013.01); *C12N 1/22* (2013.01); *Y02T 50/678* (2013.01); *C12P 7/6463* (2013.01); *Y02E 50/13* (2013.01); *C12P 2203/00* (2013.01); *C12N 1/12* (2013.01)
USPC ...... 435/134; 435/257.2; 435/69.1; 435/91.1; 435/320.1; 554/227; 536/23.1; 536/23.2; 530/350

(58) Field of Classification Search
USPC ................ 435/134, 257.2, 69.1, 91.1, 320.1; 554/227; 536/23.1, 23.2; 530/350
See application file for complete search history.

(56) References Cited

U.S. PATENT DOCUMENTS

| | | | |
|---|---|---|---|
| 3,280,502 A | 10/1966 | Farrow et al. |
| 3,475,274 A | 10/1969 | Harned |
| 3,957,578 A | 5/1976 | Narita et al. |
| 3,983,008 A | 9/1976 | Shinozaki et al. |
| 4,341,038 A | 7/1982 | Bloch et al. |
| 4,373,434 A | 2/1983 | Alexander et al. |
| 4,390,561 A | 6/1983 | Blair et al. |
| 4,901,635 A | 2/1990 | Williams |
| 4,992,605 A | 2/1991 | Craig et al. |
| 5,001,059 A | 3/1991 | Skatrud et al. |
| 5,130,242 A | 7/1992 | Barclay |
| 5,270,175 A | 12/1993 | Moll et al. |
| 5,304,481 A | 4/1994 | Davies et al. |
| 5,338,673 A | 8/1994 | Thepenier et al. |
| 5,391,724 A | 2/1995 | Kindl et al. |
| 5,395,455 A | 3/1995 | Scott et al. |
| 5,455,167 A | 10/1995 | Voelker et al. |
| 5,492,938 A | 2/1996 | Kyle et al. |
| 5,518,918 A | 5/1996 | Barclay et al. |
| 5,547,699 A | 8/1996 | Lizuka et al. |
| 5,680,812 A | 10/1997 | Linsgeseder |
| 5,685,218 A | 11/1997 | Kemper |
| 5,693,507 A | 12/1997 | Daniell et al. |
| 5,711,983 A | 1/1998 | Kyle et al. |
| 5,792,631 A | 8/1998 | Running |
| 5,826,500 A | 10/1998 | Kemper |
| 5,866,382 A * | 2/1999 | Hallborn et al. .............. 435/158 |
| 5,900,370 A | 5/1999 | Running |
| 6,166,231 A | 12/2000 | Hoeksema |
| 6,255,505 B1 | 7/2001 | Bijl et al. |
| 6,338,866 B1 | 1/2002 | Criggall et al. |
| 6,344,231 B1 | 2/2002 | Nakajo et al. |
| 6,372,460 B1 | 4/2002 | Gladue et al. |
| 6,441,208 B2 | 8/2002 | Bijl et al. |
| 6,680,426 B2 | 1/2004 | Daniell et al. |
| 6,750,048 B2 | 6/2004 | Ruecker et al. |
| 7,053,267 B2 | 5/2006 | Knauf et al. |
| 7,063,957 B2 | 6/2006 | Chen |
| 7,081,567 B2 | 7/2006 | Xue et al. |
| 7,135,620 B2 | 11/2006 | Daniell et al. |
| 7,268,276 B2 | 9/2007 | Ruezinsky et al. |

(Continued)

FOREIGN PATENT DOCUMENTS

| | | |
|---|---|---|
| CN | 1940021 A | 4/2007 |
| CN | 101037639 A | 9/2007 |

(Continued)

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Jeffries et al., Genome sequence of the lignocellulose-bioconverting and xylose-fermenting yeast *Pichia stipitis*. Nat. Biotechnol., 2007, Vo. 25 (3): 319-326.*
Kimchi-Sarfaty et al., A "Silent" polymorphism in the MDR1 gene changes substrate specificty. Science, 2007, vol. 315: 525-528.*
Kisselev L., Polypeptide release factors in prokaryotes and eukaryotes: same function, different structure. Structure, 2002, vol. 10: 8-9.*

(Continued)

*Primary Examiner* — Ganapathirama Raghu
(74) *Attorney, Agent, or Firm* — Alston & Bird LLP

(57) ABSTRACT

The invention provides methods of cultivating oil-bearing microbes using xylose as a fixed carbon source. Also provided are microorganisms that have been genetically engineered to metabolize xylose as a fixed carbon source allowing them to convert xylose into oils. Particular advantages of the processes provided herein include production of oils rather than alcohols through the microbial fermentation processes utilizing xylose.

11 Claims, No Drawings

(56) References Cited

U.S. PATENT DOCUMENTS

| | | | |
|---|---|---|---|
| 7,351,558 B2 | 4/2008 | Ruecker et al. | |
| 7,468,267 B2 | 12/2008 | Monod et al. | |
| 7,622,284 B2 * | 11/2009 | Op Den Camp et al. | 435/161 |
| 7,662,598 B2 | 2/2010 | Ruecker et al. | |
| 7,678,931 B2 | 3/2010 | Fichtali et al. | |
| 7,781,193 B2 | 8/2010 | Ruecker et al. | |
| 7,851,199 B2 | 12/2010 | Bailey et al. | |
| 7,883,882 B2 | 2/2011 | Franklin et al. | |
| 7,935,515 B2 | 5/2011 | Franklin et al. | |
| 7,939,710 B1 | 5/2011 | Apt et al. | |
| 8,029,579 B2 | 10/2011 | Knuth et al. | |
| 8,119,583 B2 | 2/2012 | Day et al. | |
| 8,187,860 B2 | 5/2012 | Franklin et al. | |
| 8,222,010 B2 | 7/2012 | Franklin et al. | |
| 8,435,767 B2 | 5/2013 | Franklin et al. | |
| 8,445,243 B2 * | 5/2013 | Matsushika et al. | 435/161 |
| 8,450,083 B2 | 5/2013 | Day et al. | |
| 2002/0012979 A1 | 1/2002 | Berry | |
| 2002/0178467 A1 | 11/2002 | Dehesh | |
| 2003/0097686 A1 | 5/2003 | Knauf et al. | |
| 2003/0145350 A1 | 7/2003 | Spener et al. | |
| 2004/0074760 A1 | 4/2004 | Portnoff et al. | |
| 2004/0235123 A1 | 11/2004 | Liao et al. | |
| 2005/0005333 A1 | 1/2005 | Ruezinsky et al. | |
| 2005/0084941 A1 | 4/2005 | Abe et al. | |
| 2005/0102716 A1 | 5/2005 | Venkatramesh et al. | |
| 2005/0112735 A1 | 5/2005 | Zappi et al. | |
| 2006/0048240 A1 | 3/2006 | Alexandrov et al. | |
| 2006/0075522 A1 | 4/2006 | Cleveland et al. | |
| 2006/0122410 A1 | 6/2006 | Fichtali et al. | |
| 2006/0153826 A1 | 7/2006 | Arnould et al. | |
| 2006/0162006 A9 | 7/2006 | Sherman et al. | |
| 2006/0199984 A1 | 9/2006 | Kuechler et al. | |
| 2006/0225341 A1 | 10/2006 | Rohr et al. | |
| 2006/0286205 A1 | 12/2006 | Fichtali et al. | |
| 2007/0009988 A1 | 1/2007 | Monod et al. | |
| 2007/0048848 A1 | 3/2007 | Sears | |
| 2007/0118916 A1 | 5/2007 | Puzio et al. | |
| 2007/0167396 A1 | 7/2007 | Dillon et al. | |
| 2007/0254354 A1 | 11/2007 | Millis et al. | |
| 2008/0014620 A1 | 1/2008 | Op Den Camp et al. | |
| 2008/0038804 A1 | 2/2008 | Du et al. | |
| 2008/0160593 A1 | 7/2008 | Oyler | |
| 2008/0206379 A1 | 8/2008 | Fabritius et al. | |
| 2008/0229451 A1 | 9/2008 | Cao et al. | |
| 2008/0256666 A1 | 10/2008 | Zhu et al. | |
| 2009/0004715 A1 | 1/2009 | Trimbur et al. | |
| 2009/0011480 A1 | 1/2009 | Trimbur et al. | |
| 2009/0018300 A1 | 1/2009 | Bloom et al. | |
| 2009/0035842 A1 | 2/2009 | Trimbur et al. | |
| 2009/0047721 A1 | 2/2009 | Trimbur et al. | |
| 2009/0061493 A1 | 3/2009 | Trimbur et al. | |
| 2009/0064567 A1 * | 3/2009 | Lippmeier et al. | 44/308 |
| 2009/0099260 A1 | 4/2009 | Namal Senanayake et al. | |
| 2009/0142322 A1 | 6/2009 | Ye | |
| 2009/0145392 A1 | 6/2009 | Clark et al. | |
| 2009/0148918 A1 | 6/2009 | Trimbur et al. | |
| 2009/0211150 A1 | 8/2009 | Wu et al. | |
| 2009/0274736 A1 | 11/2009 | Dillon et al. | |
| 2009/0298159 A1 | 12/2009 | Wu et al. | |
| 2010/0010088 A1 | 1/2010 | Chilton et al. | |
| 2010/0021912 A1 | 1/2010 | Farese et al. | |
| 2010/0035320 A1 | 2/2010 | Blanchard et al. | |
| 2010/0058651 A1 | 3/2010 | Knuth et al. | |
| 2010/0093031 A1 | 4/2010 | Kobayashi et al. | |
| 2010/0120643 A1 | 5/2010 | Brown et al. | |
| 2010/0151112 A1 | 6/2010 | Franklin et al. | |
| 2010/0151538 A1 | 6/2010 | Franklin et al. | |
| 2010/0151567 A1 | 6/2010 | Franklin et al. | |
| 2010/0170144 A1 | 7/2010 | Day et al. | |
| 2010/0239712 A1 | 9/2010 | Brooks et al. | |
| 2010/0297292 A1 | 11/2010 | Brooks et al. | |
| 2010/0297295 A1 | 11/2010 | Brooks et al. | |
| 2010/0297296 A1 | 11/2010 | Brooks et al. | |
| 2010/0297323 A1 | 11/2010 | Brooks et al. | |
| 2010/0297325 A1 | 11/2010 | Brooks et al. | |
| 2010/0297331 A1 | 11/2010 | Brooks et al. | |
| 2010/0303957 A1 | 12/2010 | Brooks et al. | |
| 2010/0303961 A1 | 12/2010 | Brooks et al. | |
| 2010/0303989 A1 | 12/2010 | Brooks et al. | |
| 2010/0303990 A1 | 12/2010 | Brooks et al. | |
| 2010/0323413 A1 | 12/2010 | Trimbur et al. | |
| 2010/0323414 A1 | 12/2010 | Trimbur et al. | |
| 2011/0014665 A1 | 1/2011 | Trimbur et al. | |
| 2011/0015417 A1 | 1/2011 | Trimbur et al. | |
| 2011/0047863 A1 | 3/2011 | Trimbur et al. | |
| 2011/0190522 A1 | 8/2011 | Trimbur et al. | |
| 2011/0195448 A1 * | 8/2011 | Lippmeier et al. | 435/41 |
| 2011/0203168 A1 | 8/2011 | Franklin et al. | |
| 2011/0252696 A1 | 10/2011 | Franklin et al. | |
| 2011/0256268 A1 | 10/2011 | Franklin et al. | |
| 2011/0256282 A1 | 10/2011 | Piechocki et al. | |
| 2011/0293785 A1 | 12/2011 | Franklin et al. | |
| 2011/0294174 A1 | 12/2011 | Franklin et al. | |
| 2012/0028319 A1 | 2/2012 | Trimbur et al. | |
| 2012/0034662 A1 | 2/2012 | Hu et al. | |
| 2012/0119862 A1 | 5/2012 | Franklin et al. | |
| 2012/0122192 A1 | 5/2012 | Trimbur et al. | |
| 2012/0128851 A1 | 5/2012 | Brooks et al. | |
| 2012/0149075 A1 | 6/2012 | Day et al. | |
| 2012/0164701 A1 | 6/2012 | Trimbur et al. | |
| 2012/0203018 A1 | 8/2012 | Franklin et al. | |
| 2012/0277452 A1 | 11/2012 | Franklin et al. | |
| 2012/0277453 A1 | 11/2012 | Franklin et al. | |
| 2012/0288930 A1 | 11/2012 | Trimbur et al. | |
| 2012/0324784 A1 | 12/2012 | Franklin et al. | |
| 2013/0004646 A1 | 1/2013 | Franklin et al. | |
| 2013/0006006 A1 | 1/2013 | Day et al. | |
| 2013/0034887 A1 | 2/2013 | Franklin et al. | |
| 2013/0078709 A1 | 3/2013 | Franklin et al. | |
| 2013/0089916 A1 | 4/2013 | Franklin et al. | |
| 2013/0096211 A1 | 4/2013 | Franklin et al. | |
| 2013/0102039 A1 | 4/2013 | Franklin et al. | |
| 2013/0165677 A1 | 6/2013 | Franklin et al. | |
| 2013/0273621 A1 | 10/2013 | Franklin et al. | |
| 2013/0295268 A1 | 11/2013 | Day et al. | |
| 2013/0296591 A1 | 11/2013 | Day et al. | |
| 2013/0316410 A1 | 11/2013 | Franklin et al. | |
| 2013/0317240 A1 | 11/2013 | Franklin et al. | |
| 2013/0323382 A1 | 12/2013 | Franklin et al. | |
| 2013/0323823 A1 | 12/2013 | Franklin et al. | |
| 2013/0330790 A1 | 12/2013 | Trimbur et al. | |
| 2013/0331584 A1 | 12/2013 | Franklin et al. | |
| 2013/0338385 A1 | 12/2013 | Franklin et al. | |

FOREIGN PATENT DOCUMENTS

| | | | |
|---|---|---|---|
| CN | 101130513 A | 2/2008 | |
| EP | 1178118 A1 | 2/2002 | |
| EP | 1681337 A1 | 7/2006 | |
| EP | 1741767 A1 | 1/2007 | |
| JP | 60006799 A | 1/1985 | |
| JP | 06/253872 A | 9/1994 | |
| WO | WO 92/11373 A1 | 7/1992 | |
| WO | WO 94/10288 A2 | 5/1994 | |
| WO | WO 95/13390 A2 | 5/1995 | |
| WO | WO 99/64618 A1 | 11/1999 | |
| WO | WO 00/61740 A1 | 10/2000 | |
| WO | WO 2005/035693 A2 | 4/2005 | |
| WO | WO 2007/027669 A1 | 3/2007 | |
| WO | WO 2007/117511 A2 | 10/2007 | |
| WO | WO 2007/134294 A2 | 11/2007 | |
| WO | WO 2008/002643 A2 | 1/2008 | |
| WO | WO 2008/011811 A1 | 1/2008 | |
| WO | WO 2008/083352 A1 | 7/2008 | |
| WO | WO 2008/130372 A2 | 10/2008 | |
| WO | WO 2008/134836 A2 | 11/2008 | |
| WO | WO 2008/151149 A2 | 12/2008 | |
| WO | WO 2009/126843 A2 | 10/2009 | |
| WO | WO 2010/019813 A2 | 2/2010 | |
| WO | WO 2010/045368 A2 | 4/2010 | |
| WO | WO 2010/063031 A2 | 6/2010 | |
| WO | WO 2010/063032 A2 | 6/2010 | |
| WO | WO 2010/120923 A1 | 10/2010 | |

(56) References Cited

FOREIGN PATENT DOCUMENTS

| WO | WO 2010/120939 A2 | 10/2010 |
|---|---|---|
| WO | WO 2011/090730 A1 | 7/2011 |
| WO | WO 2011/130573 A1 | 10/2011 |
| WO | WO 2011/130576 A1 | 10/2011 |
| WO | WO 2011/130578 A2 | 10/2011 |
| WO | WO 2011/150410 A2 | 12/2011 |
| WO | WO 2011/150411 A1 | 12/2011 |
| WO | WO 2012/061647 A2 | 5/2012 |
| WO | WO 2012/106560 A1 | 8/2012 |
| WO | WO 2012/154626 A1 | 11/2012 |
| WO | WO 2013/158938 | 10/2013 |

OTHER PUBLICATIONS

Nackley et al., Human Caechol-O-Methytransferase haplotypes modulate protein expression by altering mRNA secondary structure. Science, 2006, vol. 314: 1930-1933.*

Sauna et al., Silent polymorhisms speak: How they affect pharmacogenomics and the treatment of cancer. Cancer Res., 2007, vol. 67(20): 9609-9612.*

Seffernick et al., Melamine deaminase and Atrazine chlorohydrolase: 98 percent identical but functionally different. J. Bacteriol., 2001, vol. 183 (8): 2405-2410.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

"The Artisan Rototherm®," Artisan Industries Inc., Bulletin 9904, 2 pages, (2011). [Retrieved from the Internet Dec. 14, 2011: <URL: http://artisanind.com/ps/docs/rototherm.pdf>].

A Look Back at the U.S. Department of Energy's Aquatic Species Program: Biodiesel from Algae, NREL/TP-580-24190, John Sheehan, Terri Dunahay, John Benemann and Paul Roessler, (1998).

Abbadi et al., "Knockout of the regulatory site of 3-ketoacyl-ACP synthase III enhances short- and medium-chain acyl-ACP synthesis," The Plant Journal, 24(1):1-9, (2000).

Aggelis et al., "Enhancement of single cell oil production by *Yarrowia lipolytica* growing in the presence of *Teucrium polium* L. aqueous extract," Biotechnology Letters, 21:747-749, (1999).

Angerbauer et al., "Conversion of sewage sludge into lipids by Lipomyces starkeyi for biodiesel production," Bioresource Technology, 99:3051-3056, (2008).

Bigogno et al., "Biosynthesis of arachidonic acid in the oleaginous microalga *Parietochloris incisa* (Cholorphyceae): Radiolabeling studies," Lipids 37(2):209-216 (2002); Abstract Only.

Bonaventure et al., "Disruption of the FATB Gene in *Arabidopsis* Dethonstrates an Essential Role of Saturated Fatty Acids in Plant Growth," The Plant Cell 15:1020-1033, (2003).

Borza et al., "Multiple Metabolic Roles for the Nonphotosynthetic Plastid of the Green Alga *Prototheca Wickerhamii*," Eukaryotic Cell, 4(2):253-261, (2005).

Bouchard et al., "Characterization of Depolymerized Cellulosic Residues," Wood Sci. Technol., 23:343-355, (1989).

Broun et al., "A bifunctional oleate 12-hydroxylase: desaturase from *Lesquerella fendleri*," The Plant Journal, 13(2):201-210, (1998).

Brown et al., "The amino-acid and sugar composition of 16 species of micralgae used in mariculture," J. Exp. Mar. Biol. Ecol. 145:79-99 abstract (1991).

Canakci et al., "Biodiesel production from oils and fats with high free fatty acids," Transactions of the ASAE, 44(6):1429-1436, (2001).

Cartens et al,. "Eicosapentaenoic Acid (20:5n-3) from the Marine Microalga *Phaeodactylum tricornutum*," Journal of the American Oil Chemists' Society, 73(8)1025-1031, (1996).

Chasan, "Engineering Fatty Acids—The Long and Short of It," Plant Cell, 7:235-237, (1995).

Chen et al., "High cell density culture of microalgae in heterotrophic growth," Trends in Biotechnology, 14:421-426, (1996).

Chisti et al., "Biodiesel from microalgae," Biotechnology Advances, 25:294-306, (2007).

Courchesne et al., "Enhancement of Lipid Production Using Biochemical, Genetic and Transcription Factor Engineering Approaches," J Biotechnol. Epub, 141(1-2):31-41, (2009).

Covello et al., "Functional Expression of the Extraplastidial *Arabidopsis thaliana* Oleate Desaturase Gene (FAD2) in *Saccharomyces cerevisiae*'," Plant Physiol. 111:223-226, (1996).

Da Silva et al., "Effect of n-dodecane on *Crypthecodinium cohnii* fermentations and DHA production," J Ind Microbiol Biotechnol, DOI 10.1007/s10295-006-0081-8, 9 pages, (2006).

Dai et al., "Biodiesel generation from oleaginous yeast Rhodotorula glutinis with xylose assimilating capacity," African Journal of Biotechnology, 6(18):2130-2134, (2007).

Dehesh et al., "KAS IV: a 3-ketoacyl-ACP synthase from *Cuphea* sp. is a medium chain specific condensing enzyme," The Plant Journal, 15:383-390, (1998).

Dehesh et al., "Production of high levels of 8:0 and 10:0 fatty acids in transgenic canola by overexpression of Ch FatB2, a thioesterase cDNA from *Cuphea hookeriana*," The Plant Journal, 9(2):167-172, (1996).

Demirbas, "Fuel Conversional Aspects of Palm Oil and Sunflower Oil," Energy Sources, 25:457-466, (2003).

Dormann et al., "Cloning and Expression in *Escherichia coli* of a Novel Thioesterase from *Arabidopsis thaliana* Specific for Long-Chain Acyl-Acyl Carrier Proteins," Archives of Biochemistry and Biophysics, 316(1):612-618, 1995.

Dunahay et al., "Manipulation of Microalgal Lipid Production Using Genetic Engineering," Applied Biochemistry and Biotechnology, 57/58:223-231, (1996).

Eccleston et al., "Medium-chain Fatty Acid Biosynthesis and Utilization in Brassica Mapus Plants Expressing Lauroyl-Acyl Carrier Protein Thioesterase," Planta 198:46-53, (1996).

El-Fadaly et al., "Single Cell Oil Production by an Oleaginous Yeast Strain in a Low Cost Cultivation Medium," Research Journal of Microbiology, 4(8):301-313, (2009).

European Search Report and European Search Opinion for application EP08769988 mailed Jul. 1, 2011.

European Search Report and European Search Opinion for application EP11158642 mailed Jul. 1, 2011.

Evans et al., "A comparison of the oleaginous yeast, Candida curvata, grown on different carbon sources in continuous and batch culture," Lipids, 18(09):623-629, (1983).

Facciotti et al., "Improved stearate phenotype in transgenic canola expressing a modified acyl-acyl carrier protein thioesterase," Nat Biotechnol., 17(6):593-597, (1999).

Fall et al., "Bioconversion of Xylan to Triglycerides by Oil-Rich Yeasts," Applied and Environmental Microbiology, 47(5):1130-1134, (1984).

Ferrentino, "Microalgal oil extraction and in situ transesterification," University of New Hampshire, Pub. No. MT 1447885, 93 pages, (2007).

Ferrentino, et al., "Microalgal Oil Extraction and In-situ Transesterification," AIChE Annual Mtg, San Francisco, CA, Nov. 11-13, 2006. Abstract.

Fukuda et al., "Biodiesel Fuel Production by Transesterification of Oils," J. Biosci. Bioeng., 92(5):405-416, (2001).

Garrote et al., "Manufacture of Xylose-Based Fermentation Media from Corncobs by Posthydrolysis of Autohydrolysis Liquors," Appl Biochem Biotechnol., 95(3):195-207, (2001).

Gill et al., "Lipid Accumulation in an Oleaginous Yeast (Candida 107) Growing on Glucose in Single-Stage Continuous Culture," Applied and Environmental Microbiology, 33(02):231-239, (1977).

Gusakov et al., "Design of Highly Efficenet Cellulase Mixtures for Enzymatic Hydrolysis of Cellulose," Biotechnol and Bioengineering, 97(5):1028-1038, (2007).

Ha et al., "Engineered *Saccharomyces cerevisiae* capable of simultaneous cellobiose and xylose fermentation" PNAS, 108(2):504-509, (2011).

Hahn-Hägerdal et al., "Towards industrial pentose-fermenting yeast strains," Appl Microbiol Biotechnol, 74:937-953, (2007).

(56) References Cited

OTHER PUBLICATIONS

Hall et al., "Lipid Accumulation in an Oleaginous Yeast (Candida 107) Growing on Glucose Under Various Conditions in a One- and Two-Stage Continuous Culture," Applied and Environmental Microbiology, 33(3):577-584, (1977).
Heise et al., "Factors Controlling Medium-Chain Fatty Acid Synthesis in Plastids From *Cuphea* Embryos," Prog. Lipid Res., 330(1/2):87-95, (1994).
Helmensteine, "Gasoline and Octane Ratings," About.com, Chemistry, 1 page, (2011). [Retrieved from the Internet Oct. 3, 2011: <URL: http://chemistry.about.com/cs/howthingswork/a/aa070401a.htm>].
Henderson et al., "Lipid Composition and Biosynthesis in the Marine Dinoflagellate *Crypthecodznzum cohnii*," Phytochem. 27(6)1679-1683 (1988).
Heredia et al., "Simultaneous utilization of glucose and xylose by Candida curvata D in continuous culture," Biotechnology Letters, 10(01):25-30, (1988).
Hodge, "Chemistry and Emissions of NExBTL," Neste Oil, (2006). [Retrieved from the Internet Jan. 10, 2012: <http://bioenergy.ucdavis.edu/downloads/Neste_NExBTL_Enviro_Benefits_ofparaffins.pdf>]; p. 4.
Hossain et al., "The effect of the sugar source on citric acid production by *Aspergillus niger*," Appl Microbiol Biotechnol , 19:393-397, (1984).
Hu et al., "Microalgal Triacylglycerols as Feedstocks for Biofuel Production: Perspectives and Advances," The Plant Journal 54:621-639, (2008).
Huber et al., "Production of Liquid Alkanes by Aqueous-Phase Processing of Biomass-Derived Carbohydrates," Science, 308:1446-1450, (2005).
Huber et al., "Synthesis of Transportation Fuels from Biomass: Chemistry, Catalysts, and Engineering," Chem. Rev., 106: 4044-4098, (2006).
Jaworski et al., "Industrial oils from transgenic plants," Current Opinion in Plant Biology, 6:178-184, (2003).
Jeoh et al., "Cellulase Digestibility of Pretreated Biomass Is Limited by Cellulose Acessibility," Biotechnol Bioeng., 98(1)112-122, (2007).
Jha et al., "Cloning and functional expression of an acyl-ACP thioesterase FatB type from Diploknema (Madhuca) butyracea seeds in *Escherichia coli*," Plant Physiology and Biochemistry, 44:645-655, (2006).
Katayama et al, "Alpha-Linolenate and Photosynethetic Activity in Chlorella Protothecoides," Plant Physiol., 42:308-313, (1967).
Kenyon, "Fatty Acid Composition of Unicellular Strains of Blue-Green Algae," J. Bacteriology 109(2):827-834 (1972).
Kong et al., "Microbial production of lipids by cofermentation of glucose and xylose with Lipomyces starkeyi 2#," Chinese Journal of Bioprocess Engineering, 05(02):36, (2007). Abstract.
Lawford et al., "Performance Testing of *Zymomonas mobilis* Metabolically Engeineered for Confermation of Glucose, Xylose, and Arabinose," Appl Biochem Biotechnol., 98-100:429-48, (2002).
Leon-Banares et al., "Transgenic microalgae as green cell-factories," Trends in Biotechnology, 22(1):45-52, (2004).
Li et al., "Large-scale biodiesel production from microalga Chlorella protothecoides through heterotrophic cultivation in bioreactors," Biotechnology and Bioengineering, 98(04):764-771, (2007).
Li et al., "Articles: Biocatalysts and Bioreactor Design, Biofuels From Microalgae," Biotechnol. Prog., 24:815-820, (2008).
Li et al., "Enzymatic transesterification of yeast oil for biodiesel fuel production," The Chinese Journal of Process Engineering, 07(01):137-140 (2007), and machine translation.
Li et al., "High-density cultivation of oleaginous yeast *Rhodosporidium toruloides* Y4 in fed-batch culture," Enzyme and Microbial Technology, 41:312-317, (2007).
Li et al., "Screening of oleaginous yeasts for broad-spectrum carbohydrates assimilating capacity," China Biotechnology, 25(12):39-44 (2005), and machine translation.
Liu et al., "Biodiesel production by direct methanolysis of oleaginous microbial biomass," Journal of Chemical Technology and Biotechnology, 82:775-780, (2007).
Lubitz, "The Protein Quality, Digestibility, and Composition of Algae, *Chlorella* 71105," J. Food Sci. 28(2):229-232 (1963).
Mayer et al., A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Resid.
Meesters et al., "High-cell-density cultivation of the lipid accumulating yeast *Cryptococcus curvatus* using glycerol as a carbon source," Applied Microbiology and Biotechnology, 45:575-579, (1996).
Mekhedov et al., "Toward a Functional Catalog of the Plant Genome. A Survey of Genes for Lipid Biosynthesis," Plant Physiology, 122:389-401, (2000).
Miao et al., "Biodiesel Production From Heterotrophic Microalgal Oil," Biosource Technology, 97(06):841-846, (2006).
Miao et al., "High Yield Bio-Oil Production from Fast Pyrolysis by Metabolic Controlling of *Chlorella* Protothecoides," J. Biotech., 110:85-93, (2004).
Morris, "Effect of Growth Temperature on the Cryopreservation of *Prototheca*," Journal of General Microbiology, 94:395-399, (1976).
Murakami et al., "Lipid Composition of Commercial Bakers' Yeasts Having Different Freeze-tolerance in Frozen Dough," Biosci. Biotechnol. Biochem., 60(11)1874-1876, (1996).
Neish et al., "Carbohydrate Nutrition of *Cholorella vulgaris*," Canadian Journal of Botany, 29:68-78, (1951).
Otles et al., "Fatty Acid Composition of *Chlorella* and *Spirulina* Microalgae Species," Journal of AOAC International, 84(6):1708-1714, (2001).
Papanikolaou et al., "Lipid production by *Yarrowia lipolytica* growing on industrial glycerol in a single-stage continuous culture," Bioresource Technology, 82:43-49, (2002).
Papanikolaou et al., "*Yarrowia lipolytica* as a potential producer of citric acid from raw glycerol," Journal of Applied Microbiology , 92:737-744, (2002).
PCT International Preliminary Report on Patentability (Chapter I) of May 31, 2011 for application PCT/US09/066142.
PCT International Preliminary Report on Patentability (Chapter I) of Aug. 13, 2012 for application PCT/US11/38463.
PCT International Preliminary Report on Patentability (Chapter I) of Dec. 7, 2009 for application PCT/US08/65563.
PCT International Search Report for application PCT/US2011/032582 mailed Aug. 9, 2011.
PCT International Search Report for application PCT/US2011/038463 mailed Jan. 18, 2012.
PCT International Search Report for application PCT/US2012/023696 mailed May 23, 2012.
PCT International Search Report for application PCT/US2012/036690 mailed Aug. 30, 2012.
PCT International Search Report of Aug. 20, 2010 for application PCT/US2009/066142.
PCT International Search Report of Nov. 5, 2010 for application PCT/US2009/066141.
PCT International Search Report of Nov. 6, 2008 for application PCT/US08/65563.
PCT Written Opinion of the International Search Authority of Aug. 20, 2010 for application PCT/US2009/066142.
PCT Written Opinion of the International Searching Authority for application PCT/US2011/032582 mailed Aug. 9, 2011.
PCT Written Opinion of the International Searching Authority for application PCT/US2011/038463 mailed Jan. 18, 2012.
PCT Written Opinion of the International Searching Authority for application PCT/US2012/023696 mailed May 23, 2012.
PCT Written Opinion of the International Searching Authority for application PCT/US2012/036690 mailed Aug. 30, 2012.
PCT Written Opinion of the International Searching Authority of Nov. 5, 2010 for application PCT/US2009/066141.
PCT Written Opinion of the International Searching Authority of Nov. 6, 2008 for application PCT/US08/65563.
Petkov et al., "Which are fatty acids of the green alga *Chlorella*?," Biochemical Systematics and Ecology, 35:281-285, (2007).

(56) References Cited

OTHER PUBLICATIONS

Powell et al., "Algae Feeding in Humans," J. Nutrition, 75:7-12, (1961).
Radakovits et al., "Genetic Engineering of Algae for Enhanced Biofuel Production," Eukaryotic Cell, 9(04): 486-501, (2010).
Ratledge, "Regulation of lipid accumulation in oleaginous microorganisms," Biochem Soc Trans., 30(Pt 6):1047-1050, 2002.
Rehm et al., "Heterologous expression of the acyl-acyl carrier protein thioesterase gene from the plant *Umbellularia californica* mediates polyhydroxyalkanoate biosynthesis in recombinant *Escherichia coli*," Appl Microbiol Biotechnol, 55:205-209, (2001).
Rosenberg et al., "A Green Light for Engineered Algae: Redirecting Metabolism to Fuel a Biotechnology Revolution," Current Opinion in Biotechnology. Tissue, Cell and Pathyway Engineering, E-Pub 19:430-436, (2008).
Roy et al., "Production of Intracellular Fat by the Yeast Lipomyces starkeyi," Indian Journal of Experimental Biology, 16(4):511-512, (1978).
Running et al., "Extracellular production of L-ascorbic acid by *Chlorella* protothecoides, *Prototheca* species, and mutants of *P. moriformis* during aerobic culturing at low pH," Journal of Industrial Microbiology & Biotechnology, 29:93-98, (2002).
Running et al., "The pathway of L-ascorbic acid biosynthesis in the colourless microalga *Prototheca moriformis*," Journal of Experimental Botany, 54(389):1841-1849, (2003).
Sakai et al., "Effect of Lignocellulose-Derived Inhibitors on Growth of and Ethanol Production by Growth-Arrested Corynebacterium glutamicum R," Applied and Environmental Microbiology, 73(7):2349-2353, (2007).
Schütt et al., "The role of acyl carrier protein isoforms from *Cuphea lanceolata* seeds in the de-novo biosynthesis of medium-chain fatty acids," Publication, Planta, 205:263-268, (1998).
Schütti et al., "β-Ketoacyl-acyl carrier protein synthase IV: a key enzyme for regulation of medium-chain fatty acid synthesis in *Cuphea lanceolata* seeds," Planta, 215:847-854, (2002).
Spolaore et al., "Commercial Applications of Microalgae," J. Biosci. Bioeng. 101(2):87-96 (2006).
Sud et al., "Lipid Composition and Sensitivity of *Prototheca wickerhamii* to Membrane-Active Antimicrobial Agents," Antimicrobial Agents and Chemotherapy, 16:486-490, (1979).
Suh et al., "What limits production of unusual monoenoic fatty acids in transgenic plants?," Planta, 215:584-595, (2002).
U.S. Appl. No. 12/131,766, Advisory Action mailed Oct. 13, 2011.
U.S. Appl. No. 12/131,766, Non-Final Office Action mailed Aug. 1, 2011.
U.S. Appl. No. 12/131,766, Non-Final Office Action mailed Nov. 23, 2010.
U.S. Appl. No. 12/131,766, Non-Final Office Action mailed Dec. 10, 2009.
U.S. Appl. No. 12/131,766, Requirement for Restriction/Election mailed Aug. 5, 2009.
U.S. Appl. No. 12/131,766, Requirement for Restriction/Election mailed Aug. 17, 2010.
U.S. Appl. No. 12/131,773, Final Office Action mailed Mar. 21, 2011.
U.S. Appl. No. 12/131,773, Non-Final Office Action mailed Jun. 25, 2010.
U.S. Appl. No. 12/131,773, Non-Final Office Action mailed Dec. 15, 2009.
U.S. Appl. No. 12/131,773, Requirement for Restriction/Election mailed Aug. 6, 2009.
U.S. Appl. No. 12/131,783, Final Office Action mailed Jan. 12, 2012.
U.S. Appl. No. 12/131,783, Non-Final Office Action mailed Jun. 6, 2011.
U.S. Appl No. 12/131,783, Requirement for Restriction/Election mailed Apr. 19, 2011.
U.S. Appl. No. 12/131,793, Final Office Action mailed Mar. 30, 2010.
U.S. Appl. No. 12/131,793, Non-Final Office Action mailed Jun. 21, 2012.
U.S. Appl. No. 12/131,793, Non-Final Office Action mailed Sep. 16, 2009.
U.S. Appl. No. 12/131,793, Requirement for Restriction/Election mailed Aug. 6, 2009.
U.S. Appl. No. 12/131,804, Final Office Action mailed Feb. 2, 2011.
U.S. Appl. No. 12/131,804, Non-Final Office Action mailed Mar. 3, 2010.
U.S. Appl. No. 12/131,804, Non-Final Office Action mailed Jun. 7, 2012.
U.S. Appl. No. 12/131,804, Requirement for Restriction/Election mailed Sep. 17, 2009.
U.S. Appl. No. 12/131,804, Requirement for Restriction/Election mailed Nov. 18, 2009.
U.S. Appl. No. 12/194,389, Final Office Action mailed Jan. 5, 2011.
U.S. Appl. No. 12/194,389, Non-Final Office Action mailed Feb. 4, 2010.
U.S. Appl. No. 12/194,389, Requirement for Restriction/Election mailed Oct. 5, 2010.
U.S. Appl. No. 12/194,389, Requirement for Restriction/Election mailed Nov. 2, 2009.
U.S. Appl. No. 12/628,144, Final Office Action mailed Nov. 16, 2010.
U.S. Appl. No. 12/628,144, Final Office Action mailed Dec. 5, 2011.
U.S. Appl. No. 12/628,144, Non-Final Office Action mailed Jun. 7, 2011.
U.S. Appl. No. 12/628,144, Non-Final Office Action mailed Jul. 8, 2010.
U.S. Appl. No. 12/628,147, Examiner Interview Summary Record mailed Mar. 3, 2011.
U.S. Appl. No. 12/628,147, Final Office Action mailed Jul. 12, 2012.
U.S. Appl. No. 12/628,147, Final Office Action mailed Oct. 1, 2010.
U.S. Appl. No. 12/628,147, Non-Final Office Action mailed May 25, 2010.
U.S. Appl. No. 12/628,147, Non-Final Office Action mailed Oct. 25, 2011.
U.S. Appl. No. 12/628,149, Non-Final Office Action mailed Jun. 25, 2010.
U.S. Appl. No. 12/628,149, Non-Final Office Action mailed Sep. 16, 2010.
U.S. Appl. No. 12/628,149, Notice of Allowance mailed Dec. 15, 2010.
U.S. Appl. No. 12/628,150, Non-Final Office Action mailed Apr. 29, 2010.
U.S. Appl. No. 12/628,150, Non-Final Office Action mailed Oct. 13, 2010.
U.S. Appl. No. 12/628,150, Notice of Allowance mailed Mar. 21, 2011.
U.S. Appl. No. 12/772,163, Non-Final Office Action mailed May 25, 2012.
U.S. Appl. No. 12/772,163, Requirement for Restriction/Election mailed Jun. 24, 2011.
U.S. Appl. No. 12/772,164, Final Office Action mailed May 24, 2012.
U.S. Appl. No. 12/772,164, Non-Final Office Action mailed Oct. 12, 2011.
U.S. Appl. No. 12/772,164, Requirement for Restriction/Election mailed Jul. 20, 2011.
U.S. Appl. No. 12/772,170, Final Office Action mailed Feb. 21, 2012.
U.S. Appl. No. 12/772,170, Non-Final Office Action mailed Sep. 13, 2011.
U.S. Appl. No. 12/772,170, Requirement for Restriction/Election mailed Jul. 13, 2011.
U.S. Appl. No. 12/772,173, Final Office Action mailed May 7, 2012.
U.S. Appl. No. 12/772,173, Non-Final Office Action mailed Dec. 16, 2011.
U.S. Appl. No. 12/772,173, Requirement for Restriction/Election mailed Oct. 26, 2011.
U.S. Appl. No. 12/772,174, Non-Final Office Action mailed Nov. 29, 2011.
U.S. Appl. No. 12/772,174, Requirement for Restriction/Election mailed Aug. 10, 2011.
U.S. Appl. No. 12/981,409, Non-Final Office Action mailed Jan. 6, 2012.
U.S. Appl. No. 12/981,409, Notice of Allowance mailed May 29, 2012.

(56) References Cited

OTHER PUBLICATIONS

U.S. Appl. No. 12/981,409, Requirement for Restriction/Election mailed Apr. 19, 2012.
U.S. Appl. No. 12/981,409, Requirement for Restriction/Election mailed Oct. 28, 2011.
U.S. Appl. No. 13/029,061, Requirement for Restriction/Election mailed Nov. 29, 2011.
U.S. Appl. No. 13/045,500, Non-Final Office Action mailed Mar. 9, 2012.
U.S. Appl. No. 13/073,757, Non-Final Office Action mailed Aug. 15, 2011.
U.S. Appl. No. 13/073,757, Non-Final Office Action mailed Dec. 29, 2011.
U.S. Appl. No. 13/073,757, Notice of Allowance mailed Apr. 17, 2012.
U.S. Appl. No. 13/406,417, Requirement for Restriction/Election mailed Apr. 30, 2012.
U.S. Appl. No. 12/628,147, Notice of Allowance and Examiner Initiated Interview Summary mailed Aug. 7, 2012.
Van De Loo et al., "An oleate 12-hydroxylase from *Ricinus communis* L. is a fatty acyl desaturase homolog," Proc. Natl. Acad. Sci. USA, 92:6743-6747, (1995).
Van Gerpen, "Commercial Biodiesel Production," Oilseed and Biodiesel Workshop, Billings, Montana, Jan. 9, 2008, downloaded from http://www.deq.state.mt.us/Energy/bioenergy/Biodiesel_Production_Educ_Presentations/10Montana_Production_Jan_2008_JVP.pdf on.
Van Gerpen, Fuel Processing Technology, 86:1097-1107 (2005).
Voelker et al., "Alteration of the Specificity and Regulation of Fatty Acid Synthesis of *Escherichia coli* by Expression of a Plant Medium Chain Acyl-Acyl Carrier Protein Thioesterase," Journal of Bacteriology, 176(23):7320-7327, (1994).
Voelker et al., "Broad-Range and Binary-Range Acyl-Acyl-Carrier-Protein Thioesterases Suggest an Alternative Mechanism for Medium-Chain Production in Seeds," Plant Physiol., 114:669-677, (1997).
Voetz et al., "Three Different cDNAs Encoding Acyl Carrier Proteins from *Cuphea lanceolata*'," Plant Physiol., 106:785-786, (1994).
Wang et al., "Quantitative estimate of the effect of cellulase components during degradation of cotton fibers," Carbohydrate Research, 339:819-824, (2004).
Wiberg et al., "The distribution of caprylate, caprate and laurate in lipids from developing and mature seeds of transgenic *Brassica napus* L.," Planta, 212:33-40, (2000).
Wu et al., "A Comparative Study of Gases Generated from Simulant Thermal Degradation of Autotrophic and Heterotrophic *Chlorella*," Progress in Natural Science, 2(4):311-318, (1992).
Wu et al., "New Discoveries in Study on Hydrocarbons From Thermal Degradation of Heterotrophically Yellowing Algae," Science in China, 37(3):326-35, (1994).
Wyman et al., "Comparative Sugar Recovery Data From Laboratory Scale Application of Leading Pretreatment Technologies to Corn Stover," Bioresour Technol., 96(18):2026-2032, (2005).
Xu et al., "High quality biodiesel production from a microalga *Chlorella* protothecoides by heterotrophic growth in fermenters," Journal of Biotechnology, 126:499-507, (2006).
Yu et al., "Modifications of the metabolic pathways of lipid and triacylglycerol production in microalgae," Microbial Cell Factories, 10:91, (2011). [Retrieved from the Internet Jul. 24, 2012: <URL: http://www.microbialcellfactories.com/content/10/1/91>].
Zarowska et al., "Production of Citric Acid on Sugar Beet Molasses by Single and Mixed Cultures of *Yarrowia lipolytica*," Electronic Journal of Polish Agricultural Universities, 4(2):1-7, (2001). [Retrieved from the Internet Oct. 3, 2011: <URL: http://.
Zhao et al., "Medium optimization for lipid production through co-fermentation of glucose and xylose by the oleaginous yeast Lipomyces starkeyi," Eur. J. Lipid Sci. Technol., 110:405-412, (2008).
Zhao et al., "Toward cheaper microbial oil for biodiesel oil," China Biotechnology, 25(02):8-11 (2005).

Barnes et al., "Contribution of 5'- and 3'-untranslated regions of plastid mRNAs to the expression of *Chlamydomonas reinhardtii* chloroplast genes," Mol Genet Genomics, 274(6):625-636, (2005).
Blowers et al., "Studies on *Chlamydomonas* chloroplast transformation: foreign DNA can be stably maintained in the chromosome," Plant Cell, 1(1):123-132, (1989).
Ciferri, "Thiamine-deficiency of *Prototheca*, a Yeast-like Achloric Alga," Nature, 178:1475-1476, (1956).
Davies et al.,"Expression of the Arylsulfatase Gene from the Beta 2-Tubulin Promoter in *Chlamydomonas reinhardtii*," Nucleic Acids Research, 20(12):2959-2965, (1992).
Debuchy et al., "The argininosuccinate lyase gene of *Chlamydomonas reinhardtii*: an important tool for nuclear transformation and for correlating the genetic and molecular maps of the ARG7 locus," EMBO J., 8(10):2803-2809, (1989).
Deshnium et al., "Transformation of *Synechococcus* with a gene for choline oxidase enhances tolerance to salt stress," Plant Mol Biol, 29(5):897-907, (1995).
Franzen et al., "Chloroplast transit peptides from the green alga *Chlamydomonas reinhardtii* share features with both mitochondrial and higher plant chloroplast presequences," FEBS Letters, 260(2):165-168, (1990).
Frenz et al., "Hydrocarbon recovery by extraction with a biocompatible solvent from free and immobilized cultures of *Botryococcus braunii*," Enzyme Microb Technol, 11(11):717-724, (1989).
Frohns et al., "Potassium ion channels of Chlorella viruses cause rapid depolarization of host cells during infection," J Virol, 80(5):2437-2444, (2006).
Funes et al., "The typically mitochondrial DNA-encoded ATP6 subunit of the F1F0-ATPase is encoded by a nuclear gene in *Chlamydomonas reinhardtii*," J Biol Chem, 277(8):6051-6058, (2002).
Graves et al., "Hyaluronan synthesis in virus PBCV-1-infected *chlorella*-like green algae," Virology, 257(1):15-23, (1999).
Guiry et al., "How Many Species of Algae are There?," J. Phycol., 48:1057-1063, (2012).
Hall et al., "Expression of a foreign gene in *Chlamydomonas reinhardtii*," Gene, 124(1):75-81, (1993).
Hillen et al., "Hydrocracking of the Oils of *Botryococcus braunii* to Transport Fuels," Biotechnology and Bioengineering, 24(1):193-205, (1982).
Hiramatsu et al., "Expression of a chitinase gene and lysis of the host cell wall during Chlorella virus CVK2 infection," Virology, 260(2):308-315, (1999).
Hitz et al.,"Cloning of a Higher-Plant Plastid Omega-6 Fatty Acid Desaturase cDNA and Its Expression in a Cyanobacterium," Plant Physiology, 105(2):635-641, (1994).
Huang et al., "Expression of Mercuric Reductase From *Bacillus megaterium* MB1 in Eukaryotic Microalga *Chlorella* sp. DT: An Approach for Mercury Phytoremediation," Appl. Microbiol. Biotechnol., 72:197-205, (2006).
Inoue et al., "Analysis of oil derived from liquefaction of *Botryococcus braunii*," Biomass and Bioenergy, 6(4):269-274, (1994).
Jakobiak et al., "The Bacterial Paromomycin Resistance Gene, aphH, as a Dominant Selectable Marker in *Volvox carteri*," Protist, 55:381-393, (2004).
Jiang et al., "The actin gene promoter-driven bar as a dominant selectable marker for nuclear transformation of *Dunaliella salina*,"Yi Chuan Xue Bao, 32(4):424-433, (2005).
Kamiya, "Effects of Blue Light and Ammonia on Nitrogen Metabolism in a Colorless Mutant of *Chlorella*," Plant Celll Physiol., 30(4):513-521, (1989).
Kang et al., "Genetic diversity in chlorella viruses flanking kcv, a gene that encodes a potassium ion channel protein," Virology, 326(1):150-159, (2004).
Kang et al., "The regulation activity of Chlorella virus gene 5' upstream sequence in *Escherichia coli* and eucaryotic alage," Institute of Microbiology, Chinese Academy of Sciences, Beijing, 16(4):443-6, (2000). Abstract only.
Kawasaki et al., "Characterization of Immediate Early Genes Expressed in Chlorovirus Infections," Nucleic Acids Symp Ser, 44:161-162, (2000).

(56) References Cited

OTHER PUBLICATIONS

Kawasaki et al., "Immediate Early Genes Expressed in Chlorovirus Infections," Virology, 318(1):214-223, (2004).
Kindle, "High-Frequency Nuclear Transformation of *Chlamydomonas reinhardtii*," Proc Natl Acad Sci, 87(3):1228-1232, (1990).
Lapidot et al., "Stable Chloroplast Transformation of the Unicellular Red Alga *Porphyridium* Species," Plant Physiol, 129:7-12, (2002).
Manuell et al., "Robust expression of a bioactive mammalian protein in *Chlamydomonas* chloroplast," Plant Biotech J, 5(3):402-412, (2007).
Mayfield et al., "Expression and Assembly of a Fully Active Antibody in Algae," Proc Natl Acad Sci, 100(2):438-442, (2003).
Mendes et al., "Supercritical Carbon Dioxide Extraction of Compounds With Pharmaceutical Importance from Microalgae," Inorganica Chimica Acta, 356:328-334, (2003).
Metzger et al., "*Botryococcus braunii*: A Rich Source for Hydrocarbons and Related Ether Lipids," Applied Microbiology and Biotechnology, 66(5):486-496, (2005).
Minowa et al., "Oil Production from Algal Cells of *Dunaliella tertiolecta* by Direct Thermochemical Liquefaction," Fuel, 74(12):1735-1738, (1995).
Mitra et al., "A Chlorella Virus Gene Promoter Functions as a Strong Promoter Both in Plants and Bacteria," Biochemical and Biophysical Research Communications, 204(1):189-194, (1994).
Mitra et al., "The Chlorella Virus Adenine Methyltransferase Gene Promoter is a Strong Promoter in Plants," Plant Molecular Biology, 26(1):85-93, (1994).
PCT International Preliminary Report on Patentability for application PCT/US2011/059224 mailed May 16, 2013.
PCT International Search Report and Written Opinion of the International Searching Authority for application PCT/US2013/037261 mailed Aug. 23, 2013.
PCT International Search Report for application PCT/US2011/059224 mailed Jun. 27, 2012.
Proschold et al., "Portrait of a Species: *Chlamydomonas reinhardtii*," Genetics, 170(4):1601-1610, (2005).
Randolph-Anderson et al., "Further characterization of the respiratory deficient dum-1 mutation of *Chlamydomonas reinhardtii* and its use as a recipient for mitochondrial.transformation," Mol Gen Genet, 236(2-3):235-244, (1993).
Sakuradani, "Studies of Metabolic Engineering of Useful Lipid-producing Microorganisms," NISR Research Grant, (2004).
Sawayama et al., "Possibility of renewable energy production and $CO_2$ mitigation by thermochemical liquefaction of microalgae," Biomass and Bioenergy, 17(1):33-39, (1999).
Schreier et al., "The use of nuclear-encoded sequences to direct the light-regulated synthesis and transport of a foreign protein into plant chloroplasts," EMBO J, 4(1):25-32, (1985).
Shao et al., "Cloning and expression of metallothionein mutant α-KKS-α in *Anabaena* sp. PCC 7120," Marine Pollution Bulletin, 45(1012):163-167, (2002).
Suda, et al., "Evidence for a novel Chlorella virus-encoded alginate lyase," FEMS Microbiology Letters, 180(1):45-53, (1999).
Sun et al., "Characterization of two chitinase genes and one chitosanase gene encoded by Chlorella virus PBCV-1," Virology, 263(2):376-387, (1999).
Tang et al., "Insertion mutagenesis of *Chlamydomonas reinhardtii* by electroporation and heterologous DNA," Biochem Mol Biol Int, 36(5):1025-1035, (1995).
U.S. Appl. No. 12/131,773, Non-Final Office Action mailed Jun. 5, 2013.
U.S. Appl. No. 12/131,793, Non-Final Office Action mailed Apr. 3, 2013.
U.S. Appl. No. 12/131,793, Non-Final Office Action mailed Nov. 13, 2012.
U.S. Appl. No. 12/131,793, Notice of Allowance mailed Apr. 3, 2013.
U.S. Appl. No. 12/131,804, Non-Final Office Action mailed Oct. 26, 2012.
U.S. Appl. No. 12/628,140, Final Office Action mailed Mar. 15, 2013.
U.S. Appl. No. 12/628,140, Non-Final Office Action mailed Oct. 30, 2012.
U.S. Appl. No. 12/772,163, Non-Final Office Action mailed Dec. 12, 2012.
U.S. Appl. No. 12/772,163, Notice of Allowance mailed May 28, 2013.
U.S. Appl. No. 12/772,173, Notice of Allowance mailed Mar. 29, 2013.
U.S. Appl. No. 12/960,388, Notice of Allowance mailed May 28, 2013.
U.S. Appl. No. 12/960,388, Requirement for Restriction/Election mailed Apr. 1, 2013.
U.S. Appl. No. 13/118,365, Final Office Action mailed Jul. 22, 2013.
U.S. Appl. No. 13/118,365, Non-Final Office Action mailed Feb. 11, 2013.
U.S. Appl. No. 13/118,365, Requirement for Restriction/Election mailed Oct. 11, 2012.
U.S. Appl. No. 13/406,417, Non-Final Office Action mailed Nov. 5, 2012.
U.S. Appl. No. 13/479,200, Non-Final Office Action mailed Apr. 10, 2013.
U.S. Appl. No. 13/479,200, Non-Final Office Action mailed Sep. 9, 2013.
U.S. Appl. No. 13/479,200, Requirement for Restriction/Election mailed Jan. 15, 2013.
U.S. Appl. No. 13/527,480, Requirement for Restriction/Election mailed May 3, 2013.
U.S. Appl. No. 13/543,666, Non-Final Office Action mailed Sep. 5, 2013.
U.S. Appl. No. 13/543,666, Requirement for Restriction/Election mailed Jan. 3, 2013.
U.S. Appl. No. 13/547,457, Non-Final Office Action mailed Jul. 8, 2013.
U.S. Appl. No. 13/550,412, Non-Final Office Action mailed Oct. 29, 2012.
U.S. Appl. No. 13/550,412, Notice of Allowance mailed Feb. 21, 2013.
U.S. Appl. No. 13/558,252, Final Office Action mailed Jul. 9, 2013.
U.S. Appl. No. 13/558,252, Non-Final Office Action mailed Jan. 18, 2013.
U.S. Appl. No. 13/621,722, Requirement for Restriction/Election mailed Jan. 31, 2012.
U.S. Appl. No. 13/621,722, Non-Final Office Action mailed May 9, 2013.
U.S. Appl. No. 13/628,039, Non-Final Office Action mailed Jun. 4, 2013.
U.S. Appl. No. 13/628,039, Requirement for Restriction/Election mailed Mar. 7, 2013.
U.S. Appl. No. 13/650,018, Requirement for Restriction/Election mailed Aug. 22, 2013.
U.S. Appl. No. 13/650,024, Non-Final Office Action mailed Jul. 2, 2013.
U.S. Appl. No. 12/772,173, Notice of Allowance mailed Jul. 10, 2013.
Urano, et al., "Effect of Osmotic Stabilizers on Protoplast Generation of Chlorella ellipsoidea Yellow/White Color Mutants," Journal of Bioscience and Bioengineering, 90(5):567-569, (2000).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in *Synechococcus* sp. strain PCC 7942," FEMS Microbiology Letters, 221(2)155-159, (2003).
Vazquez-Bermudez et al., "Uptake of 2-Oxoglutarate in *Synechococcus* Strains Transformed with the *Escherichia coli* kgtP Gene," Journal of Bacteriology, 182(1):211-215, (2000).
Walker et al., "Characterization of the *Dunaliella tertiolecta* RbcS Genes and Their Promoter Activity in *Chlamydomonas reinhardtii*," Plant Cell Rep, 23(10-11):727-735, (2005).
Westphal, et al., "Vipp1 Deletion Mutant of Synechocystis: A Connection Between Bacterial Phage Shock and Thylakoid Biogenesis," Proc Natl Acad Sci U S A., 98(7):4243-4248, (2001).

(56) References Cited

OTHER PUBLICATIONS

Yamada et al., "Alternative expression of a chitosanase gene produces two different proteins in cells infected with Chlorella virus CVK2," Virology, 230(2):361-368, (1997).
Yamada et al., "Chlorella viruses," Adv Virus Res, 66:293-336, (2006).
Zhang et al., "Malic enzyme: the controlling activity for lipid production? Overexpression of malic enzyme in *Mucor circinelloides* leads to a 2.5-fold increase in lipid accumulation," Microbiology, 153(7):2013-2025, (2007).
Zurawski et al., "Nucleotide sequence of the gene for the Mr 32,000 thylakoid membrane protein from *Spinacia oleracea* and Nicotiana debneyi predicts a totally conserved primary translation product of Mr 38,950 " Proc Natl Acad Sci, 79(24):7699-7703, (1982.
"The research on the lipid content and composition of microalgae and their impact factors," Marine Science, 12(33)122-128, (2009). (English translation of first two pages).
Altschul et al., "Basic local alignment search tool," J Mol Biol, 215(3):403-410, (1990).
Andersen, "Biology and Systematics of Heterokont and Haptophyte Algae," American Journal of Botany, 91(10):1508-1522, (2004).
Appel et al., "A multicopy vector system for genetic studies in *Mucor circinelloides* and other zygomycetes," Molecular Genetics and Genomics, 271(5):595-602, (2004).
Apt et al., "Stable nuclear transformation of the diatom *Phaeodactylum tricornutum*," Mol Gen Genet, 252(5):572-579, (1996).
Bordes et al., "A new recombinant protein expression system for high-throughput screening in the yeast *Yarrowia lipolytica*," Journal of Microbiological Methods, 70(3):493-502, (2007).
Boutry et al., "Targeting of bacterial chloramphenicol acetyltransferase to mitochondria in transgenic plants," Nature, 328(6128):340-2, (1987).
Boynton et al., "Chloroplast Transformation in *Chlamydomonas* with High Velocity Microprojectiles," Science, 240(4858)1534-1538, (1988).
Chattopadhyay et al., "Effect of single amino acid mutations in the conserved GDNQ motif of L protein of Rinderpest virus on RNA synthesis in vitro and in vivo," Virus Research, 99:139-145, (2004).
Chen et al., "Recognition of prokaryotic transcription terminators by spinach chloroplast RNA polymerase," Nucleic Acids Research, 16(17):8411-8431, (1988).
Chen et al., "Highly Effective Expression of Rabbit Neutrophil Peptide-1 Gene in Chlorella ellipsoidea Cells," Current Genetics, 39:365-370, (2001).
Chow et al., "Electrotranformation of *Chlorella vulgaris*," Plant Cell Reports, 18:778-780, (1999).
Cobley et al., "CpeR is an activator required for expression of the phycoerythrin operon (cpeBA) in the cyanobacterium Fremyella diplosiphon and is encoded in the phycoerythrin linker-polypeptide operon (cpeCDESTR)," Molecular Microbiology, 44(6):1517-1531, (2002).
Cobley et al., Construction of Shuttle Plasmids Which Can Be Efficiently ficiently Mobilized From *Escherichia coli* Into the Chromatically Adapting Cyanobacterium, Plasmid, 30:90-105, (1993).
Comai et al., "Chloroplast Transport of a Ribulose Biphosphate Carboxylase Small Subunit-5-Enolpyruvyl 3-Phosphoshikimate Synthase Chimeric Protein Requires Part of the Mature Small Subunit in Addition to the Transit Peptide," Journal of Biological Chemistry, 263(29):15104-15109 (1988).
Dawson et al., "Stable Transformation of *Chlorella*: Rescure of Nitrate Reductase-Deficient Mutants with the Nitrate Reductase Gene," Current Microbiology, 35:356-362, (1997).
Dunahay et al., "Genetic Engineering of Microalgae for Fuel Production," Applied Biochemistry and Biotechnology, 34/35:331-339 (1992).
Eicks et al., "The Plastidic Pentose Phosphate Translocator Represents a Link between the Cytosolic and the Plastidic Pentose Phosphate Pathways in Plants," Plant Physiology, 128:512-522, (2002).
El-Sheekh, MM., "Stable Transformation of the Intact Cells of Chlorella Kessleri With High Velocity Microprojectiles," Biologia Plantarium 42(2): 209-216, (1999).
Falciatore et al., "Transformation of Nonselectable Reporter Genes in Marine Diatoms," Marine Biotechnology; 1:239-251, (1999).
Franklin et al., "Prospects for molecular farming in the green alga *Chlamydomonas reinhardtii*," Current Opinion in Plant Biology, 7:159-165, (2004).
Fromm et al., "Expression of Genes Transferred into Monocot and Dicot Plant Cells by Electroporation," Proc Natl Acad Sci, 82:5824-5828, (1985).
Gruber et al., "*Escherichia coli*-Anacystis nidulans plasmid shuttle vectors containing the PL promoter from bacteriophage lambda," Current Microbiology, 22(1):15-19, (1991).
Guo-Zhong et al., "The Actin Gene Promoter-driven Bar as a Dominant Selectable Marker for Nuclear Transformation of *Dunaliella salina*," Acta Genetica Sinica, 32(4): 424-433, (2005).
Hallman et al., "Reporter Genes and Highly Regulated Promoters as Tools for Transformation Experiements in *Volvox carteri*," Proc Natl Acad Sci U S A., 91(24):11562-11566, (1994).
Hanley-Bowdoin et al., "Chloroplast promoters," Trends in Biochemical Sciences, 12:67-70, (1987).
Hawkins et al., "Expression of Human Growth Hormone by the Eukaryotic Alga, *Chlorella*," Current Microbiology, 38:335-341, (1999).
Hawkins, et al., "Expression of Human Growth Hormone by the Eukaryotic Alga, *Chlorella*," Current Microbiology, 38:335-341, (1999).
Heifetz, "Genetic Engineering of the Chloroplast," Biochimie, 82:655-666, (2000).
Henikoff et al., "Amino Acid Substitution Matrices from Protein Blocks," Proc Natl Acad of Sci, 89(22):10915-10919, (1992).
Iturriaga et al. "Heterologous transformation of *Mucor circinelloides* with the *Phycomyces blakesleeanus* leu1 gene," Current Genetics, 21(3):215-223, (1992).
Jarvis et al. "Transient Expression of Firefly Luciferase in Protoplasts of the Green Alga Chlorella Ellipsoidea," Current Genet., 19: 317-322, (1991).
Kalscheuer et al., "Establishment of a Gene Transfer System for *Rhodococcus Opacus* PD630 Based on Electroporation and its Application for Recombinant Biosynthesis of Poly(3-hyroxyalkanoic acids)," Applied Microbiology and Biotechnology, 52(4):508-515, (1999).
Karlin et al., "Applications and statistics for multiple high-scoring segments in molecular sequences," Proc Natl Acad Sci, 90(12):5873-5877, (1993).
Kim et al. "Stable Integraion and Functional Expression of Flounder Growth Hormone Gene in Tranformed Microalga, Chlorella Ellipsoidea," Mar. Biotechnol. 4:63-73 (2002).
Klein et al., "High-velocity microprojectiles for delivering nucleic acids into living cells," Nature, 327:70-73, (1987).
Knauf, "The application of genetic engineering to oilseed crops," Trends in Biotechnology, 5(2):40-47, (1987).
Kohler et al., "The green fluorescent protein as a marker to visualize plant mitochondria in vivo," Plant J, 11(3):613-621, (1997).
Koksharova, "Genetic Tools for Cyanobacteria," Appl Microbiol Biotechnol, 58(2):123-37, (2002).
Krebbers et al., "The maize chloroplast genes for the beta and epsilon subunits of the photosynthetic coupling factor CF1 are fused," Nucleic Acids Res, 10(16): 4985-5002, (1982).
Levitan et al., "Dual targeting of the protein disulfide isomerase RB60 to the chloroplast and the endoplasmic reticulum," Proc Natl Acad Sci, 102(17):6225-6230, (2005).
Lu, "Biosynthesis and Gene Engineering of Plant Fatty Acids," Chinese Bulletin of Botany, 17(6):481-491, (2000). Abstract only.
Lumbreras et al., "Efficient Foreign Gene Expression in *Chlamydomonas reinhardtii* Mediated by an Endogenous Intron," Plant Journal, 14(4):441-447, (1998).
Maruyama et al., "Introduction of Foreign DNA Into Chlorella Saccharophila by Electroporation," Biotechnology Techniques, 8:821-826, (2004).

(56) References Cited

OTHER PUBLICATIONS

Mayfield et al., "Stable nuclear transformation of *Chlamydomonas reinhardtii* by using a *C. reinhardtii* gene as the selectable marker," Proc. Natl. Acad. Sci. USA, Cell Biology, 87:2087-2091, (1990).

Meng et al., "Biodiesel production from oleaginous microorganisms," Renewable Energy, 34:1-5, (2009).

Mullet et al., "Multiple transcripts for higher plantrbcL andatpB genes and localization of the transcription initiation site of therbcL gene," Plant Molecular Biology, 4(1):39-54, (1985).

Needleman et al., "A general method applicable to the search for similarities in the amino acid sequence of two proteins," Journal of Molecular Biology, 48(3):443-453, (1970).

Onai et al., "Natural Tranformation of the Termophillic Cyanbacterium Thermosynechococcus Elongatus BP-1: A Simple and Efficient Method for Gene Transfer," Mol Genet Genomics, 271(1):50-9, (2004).

Park et al., "Isolation and Characterization of Chlorella Virus From Fresh Water in Korea and Application in *Chlorella* Transformation System," Plant Pathol. J., 21(1):13-20, (2005).

Pearson et al., "Improved tools for biological sequence comparison," Proc Natl Acad Sci, 85(8):2444-2448, (1988).

Saha et al., "Transformation in *Aspergillus ochraceus*," Current Microbiology, 30(2):83-86, (1995).

Sanford, "The biolistic process," Trends in Biotechnology, 6(12):299-302, (1988).

Schultz et al., "A common core of secondary structure of the internal transcribed spacer 2 (ITS2) throughout the Eukaryota," RNA, 11(4):361-364, (2005).

Shi et al., "High-Yield Production of Lutein by the Green Microalga *Chlorella* protothecoides in Heterotrophic Fed-Batch Culture," Biotechnol. Prog., 18(4):723-727 (2002).

Skolnick et al., "From genes to protein structure and function: novel applications of computational approaches in the genomic era," TIBTECH, 18: 34-39, (2000).

Smallwood et al., "Different Substitutions at Conserved Amino Acids in Domains II and III in the Sendai L RNA Polymerase Protein Inactivate Viral RNA Synthesis," Virology, 304:135-145, (2002).

Smith et al., "Comparison of Biosequences," Adv Appl Math, 2(4):482-489, (1981).

Stemmer et al., "Single-Step Assembly of a Gene and Entire Plasmid from Large Numbers of Oligodeoxyribonucleotides," Gene, 164:49-53, (1995).

Tan et al., "Establishment of a Micro-Particle Bombardment Transformation System for *Dunaliella salina*," J Microbiol.;43(4):361-365, (2005).

Tomasinsig et al., "The Cathelicidins—Structure, Function and Evolution," Current Protein and Peptide Science, 6: 23-34, (2005).

U.S. Appl. No. 12/131,773, Final Office Action mailed Oct. 15, 2013.

U.S. Appl. No. 12/772,170, Non-Final Office Action mailed Dec. 17, 2013.

U.S. Appl. No. 13/273,179, Requirement for Restriction/Election mailed Nov. 14, 2013.

U.S. Appl. No. 13/479,200, Notice of Allowance mailed Nov. 25, 2013.

U.S. Appl. No. 13/527,480, Non-Final Office Action mailed Jun. 26, 2013.

U.S. Appl. No. 13/558,252, Notice of Allowance mailed Oct. 23, 2013.

U.S. Appl. No. 13/621,722, Final Office Action mailed Oct. 25, 2013.

U.S. Appl. No. 13/621,722, Notice of Allowance and Examiner Initiated Interview Summary mailed Jan. 10, 2014.

U.S. Appl. No. 13/650,018, Non-Final Office Action mailed Dec. 23, 2013.

U.S. Appl. No. 13/650,024, Notice of Allowance mailed Oct. 17, 2013.

U.S. Appl. No. 13/941,357, Requirement for Restriction/Election mailed Jan. 7, 2014.

Wirth et al., "Transforamtion of Various Species of Gram-Negitive Bacteria Belonging to 11 Difference Genera by Electroporation," Mol Gen Genet.; 216(1):175-177, (1989).

Wolk et al., "Construction of Shuttle Vectors Capable of Conjugative Transfer From *Escherichia coli* to Nitrogen-Fixing Filamentous Cyanobacteria," Proc Natl Acad Sci U S A., 81(5):1561-1565, (1984).

Wong et al., "*Arabidopsis thaliana* small subunit leader and transit peptide enhance the expression of *Bacillus thuringiensis* proteins in transgenic plants," Plant Mol Biol, 20(1):81-93, (1992).

Xiong et al., "High-density fermentation of microalga *Chlorella* protothecoides in bioreactor for microbio-diesel production," Appl. Microbiol. Biotechnol., 78:29-36, (2008).

\* cited by examiner

GENETICALLY ENGINEERED MICROORGANISMS THAT METABOLIZE XYLOSE

CROSS-REFERENCE TO RELATED APPLICATIONS

This application claims the benefit under 35 U.S.C. 119(e) of U.S. Provisional Patent Application No. 61/483,550, filed May 6, 2011, and U.S. Provisional Patent Application No. 61/497,501, filed Jun. 15, 2011. Each of these applications is incorporated herein by reference in its entirety.

GOVERNMENT INTERESTS

This invention was made with State of California support under California Energy Commission Grant Number PIR-08-018. The Energy Commission has certain rights to this invention.

REFERENCE TO A SEQUENCE LISTING

This application includes a sequence listing as shown in pages 1-49, appended hereto.

FIELD OF THE INVENTION

The present invention relates to the expression of xylose metabolizing pathways in oleaginous microorganisms to allow them to metabolize xylose so as to produce lipid or other useful biomass, and to oleochemical, food, fuel, and other products produced from the biomass.

BACKGROUND OF THE INVENTION

An important and difficult challenge in biotechnology is unleashing the vast potential of carbon capture in cellulosic materials for conversion into valuable substances such as liquid fuel, chemicals, food, and other products. One specific challenge relates to using xylose, commonly found in depolymerized hemicellulose, as a carbon source for the heterotrophic cultivation of microorganisms. Although much work has been done in using xylose in the production of ethanol using yeast, most yeast strains either cannot utilize xylose or utilize xylose only very inefficiently (see Jeffries, 2006, Curr. Op. Biotech. 17: 320-326; and Wang et al., 2004, Biotechnol. Lett. 26(11): 885-890).

Certain oleaginous microorganisms (e.g. oleaginous yeast and oleaginous microalgae) are capable of converting fixed-carbon energy sources into higher value products such as triglycerides, fatty acids, carbohydrates, and proteins. In addition, the microalgae themselves can be valuable as a food source. For example, certain species of oleaginous microalgae have been genetically engineered to produce "tailored oils", which means that their triglyceride content shows altered distributions of fatty acid chain lengths and saturation relative to the strains from which they were derived. See PCT Pub. Nos. 2008/151149, 2009/126843, 2010/045358, 2010/063031 and 2010/063032 and PCT App. Nos. U.S. Ser. No. 11/038,463 and U.S. Ser. No. 11/038,464.

The ability to convert xylose to lipid and other products in meaningful amounts using oleaginous microorganisms would be of major environmental significance because it would reduce our dependence on fossil fuels and reduce the cost of microbial oils.

SUMMARY OF THE INVENTION

In one aspect, the present invention provides a microorganism of the kingdom Plantae, the microorganism comprising a recombinant nucleic acid operable to produce an active xylose metabolic pathway enzyme. In some cases, the microorganism is capable of increasing in cell number or producing lipid when cultured on a carbon source consisting essentially of xylose. In some cases, the microorganism converts xylose to triglyceride. In some cases, the microorganism is capable of accumulating 10, 20, 30, 40, 50, 60, 70, or 80% triglyceride by dry cell weight when cultured using glucose as a carbon source. In some cases, the microorganism is capable of accumulating at least 10, 20, 30, 40, 50, 60, 70, or 80% triglyceride by dry cell weight when cultured on pure xylose. In some cases, the microorganism is capable of accumulating at least 50% triglyceride by dry cell weight when cultured on glucose as a carbon source and is capable of accumulating at least 20% triglyceride by dry cell weight when cultured on pure xylose. In some cases, the microorganism is cultured on a carbon source that is 60% glucose and 40% xylose under nitrogen limiting conditions, the cells produce lipid in which the carbon atoms are at least 5, 10, 20, 30, 40, or 50% derived from carbon atoms of xylose, as measured by isotopic tracing. In some cases, the microorganism is capable of consuming at least 90% of the xylose in a culture media having 2.5% xylose as a sole carbon source in less than or equal to 21, 14 or 7 days.

In some cases, the recombinant nucleic acid is operable to encode one or more of an active xylose transporter, a xylulose-5-phosphate transporter, a xylose isomerase, a xylulokinase, a xylitol dehydrogenase, or a xylose reductase. In some cases, the recombinant nucleic acid encodes an active xylulose-5-phosphate transporter in operable linkage with a plastid-targeting signal sequence and wherein the xylulose-5-phosphate transporter is operable to transport xylulose-5-phosphate into a plastid. In some cases, the recombinant nucleic acid is operable to encode (a) a xylulose-5-phosphate transporter protein with a plastid-targeting signal sequence, so as to cause transport of xylulose-5-phosphate into a plastid, (b) a xylulokinase, and (c) either a xylose isomerase, or both of a xylitol dehydrogenase and a xylose reductase.

In some cases, the microorganism is of the subkingdom Viridiplantae. In some cases, the microorganism is of the infrakingdom or phyla Chlorophytae, of the subphylum Tetraphytina, the class Trebouxiophyceae, or the order Chlorellales. In some cases, the microorganism is of the genus *Chlorella* or *Prototheca*. In some cases, the microorganism is of the species *Prototheca moriformis* or *Chlorella protothecoides*.

In some cases, the microorganism further comprising a recombinant modification operable to alter the fatty acid profile of lipid produced by the microorganism. In some cases, the recombinant modification comprises an exogenous gene that encodes an active acyl-ACP thioesterase, ketoacyl-ACP synthase or a fatty acid desaturase, or is operable to reduce or ablate an acyl-ACP thioesterase, ketoacyl-ACP synthase or fatty acid desaturase.

In another aspect, the present invention provides a method for producing microbial biomass or a product produced from the biomass, in which the method comprises heterotrophically cultivating a recombinant microorganism, as discussed above or herein, in a culture medium comprising xylose so as to convert xylose into the microbial biomass. In some cases, the microbial biomass comprises microbial lipid. In some cases, the lipid is used to make a product selected from the group consisting of: a chemical, a lubricant, a detergent, a fuel, a food oil, and a cosmetic ingredient. In some cases, the product is a fuel selected from biodiesel or renewable diesel.

In some cases, the culture medium comprises a carbon source that is greater than 50% xylose. In some cases, the carbon source is greater than 55%, 60%, 65%, 70%, 75%, 80%, 85%, 90%, or 95% xylose.

In another aspect, the present invention provides a natural oil produced by any of the microorganisms, as discussed above or herein, or produced by any of the methods discussed above or herein.

In another aspect, the present invention provides an oleochemical, food oil, fuel, or other product produced from the natural oil discussed above.

In another aspect, the present invention provides recombinant oleaginous microbes that utilize xylose as a carbon source. In one embodiment, the oleaginous microbe is a microalgae, oleaginous yeast, oleaginous fungi or oleaginous bacteria. In another embodiment, the recombinant microbes are microalgae cells, including but not limited to cells of the genus *Prototheca*, comprising one or more exogenous genes that allow the cells to utilize, or utilize more efficiently, xylose as a carbon source. In some embodiments, the cell is a strain of the species *Prototheca moriformis, Prototheca krugani, Prototheca stagnora* or *Prototheca zopfii*, and in other embodiments, the cell has a 23S rRNA sequence with at least 70, 75, 80, 85 or 95% nucleotide identity to one or more of SEQ ID NOs: 1-9. The exogenous gene comprises coding sequence in operable linkage with a promoter, and in some embodiments the promoter is from a gene endogenous to a species of the genus *Prototheca*. In further embodiments the coding sequence encodes a protein selected from the group consisting of oxidoreductase pathway proteins, xylose isomerase pathway proteins, xylose translocator proteins and xylose transporter proteins.

In various embodiments, the microalgae cell includes one or more exogenous genes that allow the cells to utilize, or utilize more efficiently, xylose as a carbon source. For example, microalgae cells of the invention include those that have been engineered to comprise: (i) one or more genes that encode a xylose isomerase pathway protein; or (ii) one or more genes that encode an oxidoreductase pathway protein; or (iii) one or more genes that encode a xylose isomerase pathway protein; (iv) one or more genese that encode a xylose transporter protein; or (v) one or more genes that encode a xylose translocator protein; or combinations of (i), (ii), (iii), (iv), and (v). In an embodiment, the microbial cell is engineered to express a xylose transporter protein and a xylose isomerase pathway protein. In another embodiment, the microbial cell is engineered to express a xylose transporter protein and an oxidoreductase pathway protein. In a further embodiment, the microbial cell is engineered to express a xylose transporter protein, an oxidoreductase pathway protein and a xylose isomerase protein. In yet another embodiment, the microbial cell is engineered to express a xylose transporter protein, an oxidoreductase pathway protein, and a xylose translocator protein. In another embodiment, the microbial cell is engineered to express a xylose transporter protein, a xylose isomerase pathway protein, and a xylose translocator protein. In another embodiment, the microbial cell is engineered to express a xylose transporter protein, a xylose isomerase pathway protein, a xylose isomerase pathway protein, and a xylose translocator protein.

In some embodiments of the present invention, the recombinant oleaginous microbe comprises a first exogenous gene that encodes a xylose translocator protein selected from GPT-A-XPT (SEQ ID NO: 45), GPT-F-XPT (SEQ ID NO: 47) or S106SAD-XPT (SEQ ID NO: 49), a second exogenous gene that encodes a xylose transporter protein selected from SUT1 (SEQ ID NO: 37), GXS1 (SEQ ID NO: 39), XLT1 (SEQ ID NO: 43) or symporter (SEQ ID NO: 41), a third exogenous gene that encodes an oxidoreductase pathway protein selected from XylA (SEQ ID NO: 15) or XYL3 (SEQ ID NO: 51), and a fourth exogenous gene that encodes a xylose isomerase pathway protein selected from XYL1 (SEQ ID NO: 35), XYL2 (SEQ ID NO: 50) or XYL3 (SEQ ID NO: 51).

In one embodiment, the recombinant oleaginous microbe comprises exogenous genes that encode XylA, XYL3, SUT1, and GPT-F-XPT. In one embodiment, the recombinant oleaginous microbe comprises exogenous genes that encode XylA, XYL2, XYL3, XLT1, and S106SAD-XPT. In one embodiment, the recombinant oleaginous microbe comprises exogenous genes that encode XylA, XYL1, XYL3, XLT1, and S106SAD-XPT. In one embodiment, the recombinant oleaginous microbe comprises exogenous genes that encode XylA, XYL1, XYL3, GXS1, and GPT-A-XPT. In one embodiment, the recombinant oleaginous microbe comprises exogenous genes that encode XYL1, XYL2, XYL3, symporter, and GPT-F-XPT. In one embodiment, the recombinant oleaginous microbe of comprises exogenous genes that encode XYL1, XYL2, XYL3, GXS1, and GPT-F-XPT. In one embodiment, the recombinant oleaginous microbe comprises exogenous genes that encode XYL2, XYL3, symporter, and S106SAD-XPT. In one embodiment, the recombinant oleaginous microbe comprises exogenous genes that encode XYL2, XYL3, XLT1, and S106SAD-XPT. In one embodiment, the recombinant oleaginous comprises exogenous genes that encode XYL2, XYL3, GXS1, and GPT-A-XPT.

In some cases, the recombinant oleaginous microbes are propagated or cultivated in a culture medium comprising a carbon source that is greater than 50% xylose. In some cases, the microbes are propagated or cultivated in a culture medium comprising a carbon source that is greater than 55%, greater than 60%, greater than 65%, greater than 70%, greater than 75%, greater than 80%, greater than 85%, greater than 90%, or greater than 95% xylose. In some cases, the microbes are propagated or cultivated in a culture medium comprising xylose as the sole carbon source. In some cases, the microbes, when propagated or cultivated in a culture medium comprising a carbon source that is greater than 50% xylose, or a culture medium comprising xylose as the sole carbon source, produce at least 25%, at least 30%, at least 35%, at least 40%, at least 45%, at least 50%, at least 55% or at least 60% of the lipid produced by a comparable microbial cell propagated or cultivated in a culture medium comprising glucose as the sole carbon source and lacking the one or more exogenous genes.

Unless otherwise indicated, reference above and throughout this specification to an exogenous gene that encodes a specified protein refers to a gene that is operable to encode the specified protein.

Another embodiment of the invention is microbial lipid composition produced by propagating or cultivating a recombinant oleaginous microbe in the presence of xylose. In one embodiment, the recombinant oleaginous microbes discussed herein are propagated and/or cultivated in the presence of cellulosic material that comprises xylose. Optionally, the cellulosic material can further comprise glucose and sucrose. The microbial lipid composition is produced by lysing the microbial cell and isolating the oil.

DETAILED DESCRIPTION OF THE INVENTION

I. Definitions

"Active" refers to a nucleic acid that is functional in a cell. For example, a promoter that has been used to drive an antibiotic resistance gene to impart antibiotic resistance to a microalgae is active in microalgae.

"Area Percent" refers to the determination of the area percent of chromatographic, spectroscopic, and other peaks generated during experimentation. The determination of the area under the curve of a peak and the area percent of a particular peak is routinely accomplished by one of skill in the art. For example, in FAME GC/FID detection methods in which fatty acid molecules in the sample are converted into a fatty acid methyl ester (FAME), a separate peak is observed for a fatty acid of 14 carbon atoms with no unsaturation (C14:0) compared to any other fatty acid such as C14:1. The peak area for each class of FAME is directly proportional to its percent composition in the mixture and is calculated based on the sum of all peaks present in the sample (i.e. [area under specific peak/total area of all measured peaks]×100). When referring to lipid profiles of oils and cells of the invention, "at least 4% C8-C14" means that at least 4% of the total fatty acids in the cell or in the extracted glycerolipid composition have a chain length that includes 8, 10, 12 or 14 carbon atoms.

"Biodiesel" is a biologically produced fatty acid alkyl ester suitable for use as a fuel in a diesel engine.

"Biomass" is material produced by growth and/or propagation of cells. Biomass may contain cells and/or intracellular contents as well as extracellular material, which includes, but is not limited to, compounds secreted by a cell.

"Bioreactor" is an enclosure or partial enclosure in which cells are cultured, optionally in suspension.

"Cellulosic material" is the product of digestion of fibrous material, typically including glucose and xylose (e.g., from hemicelullose), and optionally additional compounds such as disaccharides, oligosaccharides, lignin, furfurals and other compounds. Nonlimiting examples of sources of cellulosic material include sugar cane bagasses, sugar beet pulp, corn stover, wood chips, sawdust and switchgrass.

"Expression vector" or "expression construct" or "plasmid" or "recombinant DNA construct" refer to a nucleic acid that has been generated via human intervention, including by recombinant means or direct chemical synthesis, with a series of specified nucleic acid elements that permit transcription and/or translation of a particular nucleic acid in a host cell. The expression vector can be part of a plasmid, virus, or nucleic acid fragment. Typically, the expression vector includes a nucleic acid to be transcribed operably linked to a promoter.

"Exogenous gene" is a nucleic acid that codes for the expression of an RNA and/or protein that has been introduced ("transformed") into a cell. A transformed cell may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome or as an episomal molecule.

"Exogenously provided" refers to a molecule provided to the culture media of a cell culture.

"Fatty acid profile" shall mean the distribution of fatty acids in a cell or oil derived from a cell in terms of chain length and/or saturation pattern. In this context the saturation pattern can comprise a measure of saturated versus unsaturated acid or a more detailed analysis of the distribution of the positions of double bonds in the various fatty acids of a cell.

"Fixed carbon source" is a molecule(s) containing carbon, typically an organic molecule, that is present at ambient temperature and pressure in solid or liquid form in a culture media that can be utilized by a microorganism cultured therein.

"Heterotrophic cultivation" and variants thereof such as "heterotrophic culture" and "heterotrophic fermentation" refer to the intentional fostering of growth (increases in cell size, cellular contents, and/or cellular activity) in the presence of a fixed carbon source. Typically, heterotrophic cultivation is performed in the absence of light. However, the absence of light is not a requirement for heterotrophic cultivation. Cultivation in the absence of light means cultivation of microbial cells in the complete absence or near complete absence of light.

"Increase lipid yield" refers to an increase in the productivity of a microbial culture by, for example, increasing dry weight of cells per liter of culture, increasing the percentage of cells that constitute lipid, or increasing the overall amount of lipid per liter of culture volume per unit time.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"Microalgae" is a eukarytotic microbial organism that contains a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca*.

"Microorganism" and "microbe" are microscopic unicellular organisms.

A "natural oil" shall mean a predominantly triglyceride oil obtained from an organism, where the oil has not undergone blending with another natural or synthetic oil, or fractionation so as to substantially alter the fatty acid profile of the triglyceride. Here, the term "fractionation" means removing material from the oil in a way that changes its fatty acid profile relative to the profile produced by the organism, however accomplished. A natural oil encompasses such an oil obtained from an organism, where the oil has undergone minimal processing, including refining, bleaching and/or degumming, that does not substantially change its triglyceride profile. A natural oil can also be a "noninteresterified natural oil", which means that the natural oil has not undergone a process in which fatty acids have been redistributed in their acyl linkages to glycerol and remain essentially in the same configuration as when recovered from the organism.

"Naturally co-expressed" with reference to two proteins or genes means that the proteins or their genes are co-expressed naturally in a tissue or organism from which they are derived, e.g., because the genes encoding the two proteins are under the control of a common regulatory sequence or because they are expressed in response to the same stimulus.

"Oxidoreductase pathway" are the proteins and/or genes encoding them capable of converting xylose to xylulose 5-phosphase via xylitol and xylulose intermediates, including, without limitation, xylose reductase (converts xylose to xylitol), xylitol dehydrogenase (converts xylitol to xylulose), and xylulokinase (converts xylulose to xylulose 5-phosphate). Illustrative oxidoreductase pathway genes, include, without limitation, the XYL1, XYL2, and XYL3 genes from *Pichia stipitis*.

"Promoter" is a nucleic acid control sequence that directs transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

"Recombinant" is a cell, nucleic acid, protein or vector, that has been modified due to the introduction of an exogenous nucleic acid or the alteration of a native nucleic acid. Thus, e.g., recombinant cells express genes that are not found within the native (non-recombinant) form of the cell or express native genes differently than those genes are expressed by a non-recombinant cell. A "recombinant nucleic acid" is a nucleic acid originally formed in vitro, in general, by the manipulation of nucleic acid, e.g., using polymerases and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

"Renewable diesel" is a mixture of alkanes (such as C10:0, C12:0, C14:0, C16:0 and C18:0) produced through hydrogenation and deoxygenation of lipids.

"Saccharification" is a process of converting biomass, usually cellulosic or lignocellulosic biomass, into monomeric sugars, such as glucose and xylose. "Saccharified" or "depolymerized" cellulosic material or biomass refers to cellulosic material or biomass that has been converted into monomeric sugars through saccharification.

"Sucrose utilization gene" is a gene that, when expressed, aids the ability of a cell to utilize sucrose as an energy (carbon) source. Proteins encoded by a sucrose utilization gene are referred to herein as "sucrose utilization enzymes" and include sucrose transporters, sucrose invertases, and hexokinases such as glucokinases and fructokinases.

"Xylose isomerase pathway" are the proteins and/or genes encoding them capable of converting xylose to xylulose 5-phosphate via a xylulose intermediate, including, without limitation, xylose isomerase (converts xylose to xylulose) and xylulokinase (converts xylulose to xylulose 5-phosphate). Illustrative xylose isomerase pathway genes include, without limitation, the *Piromyces* sp. gene XylA and the *Pichia stipitis* gene XYL3.

"Xylulose 5-phosphate translocator", "xylulose 5-phosphate transporter" or "plastidic pentose phosphate translocator" is a family of plastidic membrane proteins and genes encoding such proteins that transports xylulose 5-phosphate. A non-limiting example of a xylose translocator is the XPT gene that encodes a xylulose 5-phosphate translocator from *Arabidopsis*.

"Xylose transporter" is a proteins and genes encoding such proteins that transports xylose from the cell medium into the cell and includes, without limitation, passive transporters and active transporters and translocators. Passive transporters facilitate the transport of molecule down a concentration gradient (from an area of higher concentration to an area of lower concentration) without energy consumption, and include, without limitation, the *Pichia stipitis* SUT1, SUT2, and SUT3 transporters and the *S. cerevisiae* HXT transporters. Active transporters consume energy in transporting molecules against a concentration gradient (and so transport from an area of lower concentration to an area of higher concentration). Active transporters include, without limitation, primary active transporters, which use ATP as an energy source, i.e., ATP-binding cassette (ABC) transporters, and secondary active transporters, which use energy from chemiosmotic gradients and include, without limitation antiporters and symporters, i.e., the GXS1 protein of *Candida intermedia*, the H+-symporter-like proteins (e.g. At5g59250n) from *Arabidopsis*, and the XLT1 protein from *Trichoderma reesei*.

"Xylose utilization gene" is a gene that, when expressed, aids the ability of a cell to utilize xylose as a carbon source (e.g., for producing energy and/or anabolism). Proteins encoded by a xylose utilization gene are referred to herein as "xylose utilization enzymes" and include xylose transporters, xylose translocators, oxidoreductase pathway proteins, and xylose isomerase pathway proteins.

II. General

Illustrative embodiments of the present invention overcome long standing challenges in using cell cultures to convert xylose into high-value cell biomass, by engineering a xylose utilization pathway into an organism that previously lacked the ability to metabolize xylose. In various aspects, the present disclosure provides for engineering an active xylose metabolism pathway into an organism, and especially a microorganism (also referred to herein as a microorganism), of the kingdom Plantae. Such organisms include microalgae. In another aspect, the present disclosure provides for engineering an active xylose metabolism pathway into an organism, and especially a microorganism, having both plastids and a type II fatty acid biosynthesis pathway.

Although others may have obtained ethanol production using xylose in *Saccharomyces*, such organisms are not useful for commercial scale production of lipid. By contrast, oleaginous microorganisms such as oleaginous yeast and oleaginous microalgae can accumulate greater than 20% lipid by dry cell weight, mostly as triglyceride. Although oleaginous yeast are useful in producing lipid, microalgae have a type II fatty acid biosynthesis pathway, which facilitates the use of genetic engineering to tailor the fatty acid profile of lipid, and especially triglyceride, produced by the cells. See PCT publications WO2011/151149, WO2010/063032, and WO2011/15040. In addition to producing lipid, the organisms described herein can be used to produce protein, vitamins, fiber, and other substances produced naturally, or as a result of further genetic engineering.

In accordance with an embodiment of the present invention, an exogenous nucleic acid is introduced into a cell with a plastid that is operable to produce a xylulose-5-phosphate transporter (e.g., a xylulose-5-phosphate translocator) protein that is operable to cause the transport of xylulose-5- phosphate into a plastid of the cell. In a specific embodiment, the cell is transformed with exogenous DNA that encodes a xylulose-5-phosphate transporter in operable linkage with a plastid targeting sequence. The plastid targeting sequence can direct the transporter protein to a plastid membrane (preferably the inner plastid membrane) so as to effectively transport xylulose-5-phosphate into a plastid, where it can be metabolized, and potentially into fatty acid. For example, the organism can have an endogenous pentose metabolism pathway in the plastid that metabolizes the xylulose-5-phosphate. As shown in the examples below, this has been found to be an effective method of boosting xylose utilization concurrent with cell growth and/or lipid production.

Optionally, or in addition, the cells may be capable of taking up xylose from the external milieu and converting the xylose to xylulose-5-phosphate. Exogenous genes may be needed to produce active proteins to perform these functions. For example, and as described in the Examples below, the cell may be transformed with DNA operable to encode an active xylose transporter for transporting xylose from an external medium into the cell, and a pathway for converting the xylose into xylulose-5-phosphate. For example, the pathway for converting the xylose into xylulose-5-phosphate can be a combination of a xylulokinase for converting xylulose to xylulose-5-phosphate with a pathway for converting xylose to xylulose. The pathway for converting xylose to xylulose can comprise a xylose isomerase or a combination of a xylose reductase and a xylitol dehydrogenase. Alternately, xylose transport into the cell can rely on the activity of native proteins such as hexose transport proteins.

Optionally, in a further refinement of any of the above embodiments, the cells may be transformed to express an active xylitol dehydrogenase. This modification may function to reduce or eliminate inhibition of xylose isomerase by xylitol.

The various genes may be integrated into a chromosome of the organism, or may be episomal. Preferably, the genes are stably expressed, and may be in multiple copy. In various embodiments, the genes are under the control of a regulatable or constitutive promoter. After transformation, and optionally for maintaining stability, the cells may be transformed with a selectable marker.

The cells are capable of propogation and/or lipid accumulation under heterotrophic growth conditions. Optionally, the cells may be those of an obligate heterotroph such as those of the microalgae genus, *Prototheca*. The cells, may be, for example, those of *Prototheca moriformis*. In the Examples below, *Prototheca* cells are transformed to express an active xylose metabolic pathway. It should be noted however, that the embodiments of the invention are applicable to many other species. Preferred species include those of the kingdom Plantae, the subkingdom Viridiplantae, the infrakingdom or phyla Chlorophytae, the subphylum Tetraphytina, the class Trebouxiophyceae, or the order Chlorellales. Specific examples include *Prototheca moriformis* and *Chlorella protothecoides*.

In a preferred embodiment, the resulting recombinant organism is capable of accumulating at least 10, 20, 30, 40, 50, 60, 70, or 80% triglyceride by dry cell weight when cultured using glucose as a carbon source. Further the organism can be capable of accumulating at least 10, 20, 30, 40, 50, 60, 70, or 80% triglyceride by dry cell weight when cultured on pure xylose. For example, the microorganism may be capable of accumulating at least 50% triglyceride by dry cell weight when cultured on glucose as a carbon source and is capable of accumulating at least 20% triglyceride by dry cell weight when cultured on pure xylose. In another embodiment, when cells of the recombinant organism are cultured on a carbon source that is 60% glucose and 40% xylose under nitrogen limiting conditions, the cells produce lipid in which the carbon atoms are at least 5, 10, 20, 30, 40, or 50% derived from carbon atoms of xylose, as measured by isotopic tracing. In yet another embodiment, the cells of the recombinant organism are capable of consuming at least 90% of the xylose in a culture media having 2.5% xylose as a sole carbon source in less than or equal to 35, 28, 21, 14 or 7 days.

In addition to the introduction of the xylose metabolic pathway, the organism can be genetically engineered by introducing genes that are operable to alter the fatty acid profile of lipid produced by the microorganism. As a result, xylose may be converted into acylglycerides having an altered fatty acid profile. For example, the cells can have a recombinant modification comprising one or more exogenous genes encoding an active acyl-ACP thioesterase, ketoacyl-ACP synthase or a fatty acid desaturase. Alternately, or in addition, the cells can have a recombinant modification that is operable to reduce or ablate an acyl-ACP thioesterase, ketoacyl-ACP synthase or fatty acid desaturase. Methods for performing such genetic manipulations are provided in PCT publications WO2011/151149, WO2010/063032, and WO2011/15040.

In a preferred embodiment, the xylose metabolizing cells are cultivated in a xylose containing medium. As a result, biomass is produced. In a specific embodiment, the xylose is converted into cell biomass, and triglyceride in particular. This may be shown by isotope tracing; e.g. using isotopically labeled xylose. To produce triglyceride, an oleaginous microorganism can be cultivated under nutrient limiting conditions, e.g., under nitrogen limitation. The resulting natural oil is harvested. Harvesting may include cell lysis to release oil. The oil may then be used to produce an oleochemical, a lubricant, detergent, fuel, food, oil, cosmetic ingredient, or other product. For example, the oil may be used to produce biodiesel (fatty acid esters) or renewable diesel (a fuel produced from the oil via cracking).

In an embodiment, the method includes cultivating the cells in a culture medium that comprises a carbon source that is greater than 50% xylose. For example, the carbon source can be greater than 55%, 60%, 65%, 70%, 75%, 80%, 85%, 90%, or 95% xylose.

Accordingly, a specific embodiment of the present invention comprises a microorganism having a plastid and an operable xylose metabolic pathway resulting from the introduction and expression of exogenous genes. The genes are active to convert xylose to xylulose-5-phosphate and to transport the xylulose-5-phosphate into the plastid for further metabolism. The microorganism optionally has a xylose transporter to transport xylose from an external milieu into the cell. As a result of the expression of the exogenous genes, the cell is able to grow on pure xylose and preferably can consume at least 90% of the xylose in a culture media having 2.5% xylose as a sole carbon source in, e.g., 21, 14 or 7 days or less.

III. Cultivation

The present invention generally relates to cultivation of oleaginous microbes including but not limited to microalgae, oleaginous yeast, oleaginous fungi, and oleaginous bacteria. In some embodiments, microalgae strains, particularly recombinant *Chlorella* and *Prototheca* strains, are suitable for the production of lipid. For the convenience of the reader, this section is subdivided into subsections. Subsection 1 describes *Prototheca* species and strains and how to identify new *Prototheca* species and strains and related microalgae by genomic DNA comparison. Subsection 2 describes bioreactors useful for cultivation. Subsection 3 describes media for cultivation. Subsection 4 describes oil production in accordance with illustrative cultivation methods of the invention.

1. *Prototheca* Species and Strains

*Prototheca* is a remarkable microorganism for use in the production of lipid, because it can produce high levels of lipid, particularly lipid suitable for fuel production. The lipid produced by *Prototheca* has hydrocarbon chains of shorter chain length and a higher degree of saturation than that produced by other microalgae. Moreover, *Prototheca* lipid is generally free of pigment (low to undetectable levels of chlorophyll and certain carotenoids) and in any event contains much less pigment than lipid from other microalgae. Moreover, recombinant *Prototheca* cells provided by the invention can be used to produce lipid in greater yield and efficiency, and with reduced cost, relative to the production of lipid from other microorganisms based on their increased ability to utilize xylose as a carbon source. In addition, this microalgae grows heterotrophically and can be genetically engineered. Illustrative *Prototheca* strains for use in the methods of the invention include *Prototheca wickerhamii, Prototheca stagnora* (including UTEX 327), *Prototheca portoricensis, Prototheca moriformis* (including UTEX strains 1441, 1435), and *Prototheca zopfii*. Species of the genus *Prototheca* are obligate heterotrophs.

Species of *Prototheca* for use in the invention can be identified by amplification of certain target regions of the genome. For example, identification of a specific *Prototheca* species or strain can be achieved through amplification and sequencing of nuclear and/or chloroplast DNA using primers and methodology using any region of the genome, for example using the methods described in Wu et al., *Bot. Bull. Acad. Sin.* (2001) 42:115-121 Identification of *Chlorella* spp. isolates using ribosomal DNA sequences. Well established methods of phylogenetic analysis, such as amplification and sequencing of ribosomal internal transcribed spacer (ITS1 and ITS2 rDNA), 23S rRNA, 18S rRNA, and other conserved genomic regions can be used by those skilled in the art to identify species of not only *Prototheca*, but other hydrocarbon and lipid producing organisms with similar lipid profiles and production capability. For examples of methods of identification and classification of algae also see for example *Genetics,* 2005 August; 170(4):1601-10 and *RNA,* 2005 April; 11(4): 361-4.

Thus, genomic DNA comparison can be used to identify suitable species of microalgae to be used in the present invention. Regions of conserved genomic DNA, such as but not limited to DNA encoding for 23S rRNA, can be amplified from microalgal species and compared to consensus sequences in order to screen for microalgal species that are taxonomically related to the preferred microalgae used in the present invention. Examples of such DNA sequence comparison for species within the *Prototheca* genus are shown below. Genomic DNA comparison can also be useful to identify microalgal species that have been misidentified in a strain collection. Often a strain collection will identify species of microalgae based on phenotypic and morphological characteristics. The use of these characteristics may lead to miscategorization of the species or the genus of a microalgae. The use of genomic DNA comparison can be a better method of categorizing microalgae species based on their phylogenetic relationship.

Microalgae for use in the present invention typically have genomic DNA sequences encoding for 23S rRNA that have at least 99%, least 95%, at least 90%, or at least 85% nucleotide identity to at least one of the sequences listed in SEQ ID NOs: 1-9.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Other considerations affecting the selection of microorganisms for use in the invention include, in addition to production of suitable lipids or hydrocarbons for production of oils, fuels, and oleochemicals: (1) high lipid content as a percentage of cell weight; (2) ease of growth; (3) ease of genetic engineering; and (4) ease of biomass processing. In particular embodiments, the wild-type or genetically engineered microorganism yields cells that are at least 40%, at least 45%, at least 50%, at least 55%, at least 60%, at least 65%, or at least 70% or more lipid. Preferred organisms grow heterotrophically (on sugars in the absence of light).

2. Bioreactor

Microorganisms are cultured both for purposes of conducting genetic manipulations and for production of hydrocarbons (e.g., lipids, fatty acids, aldehydes, alcohols, and alkanes). The former type of culture is conducted on a small scale and initially, at least, under conditions in which the starting microorganism can grow. Culture for purposes of hydrocarbon production is usually conducted on a large scale (e.g., 10,000 L, 40,000 L, 100,000 L or larger bioreactors) in a bioreactor. Prototheca are typically cultured in the methods of the invention in liquid media containing xylose within a bioreactor. In one embodiment, microalgae such as Prototheca are cultured in a bioreactor using a fed-batch process. Typically, the bioreactor does not allow light to enter, and the microorganisms are cultured heterotrophically, metabolizing a fixed carbon source, and in the substantial absence of light.

The bioreactor or fermentor is used to culture microalgal cells through the various phases of their physiological cycle. Bioreactors offer many advantages for use in heterotrophic growth and propagation methods. To produce biomass for use in food, microalgae are preferably fermented in large quantities in liquid, such as in suspension cultures as an example. Bioreactors such as steel fermentors can accommodate very large culture volumes (40,000 liter and greater capacity bioreactors are used in various embodiments of the invention). Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture. Other culture parameters, such as the pH of the culture media, the identity and concentration of trace elements, and other media constituents can also be more readily manipulated using a bioreactor.

Bioreactors can be configured to flow culture media though the bioreactor throughout the time period during which the microalgae reproduce and increase in number. In some embodiments, for example, media can be infused into the bioreactor after inoculation but before the cells reach a desired density. In other instances, a bioreactor is filled with culture media at the beginning of a culture, and no more culture media is infused after the culture is inoculated. In other words, the microalgal biomass is cultured in an aqueous medium for a period of time during which the microalgae reproduce and increase in number; however, quantities of aqueous culture medium are not flowed through the bioreactor throughout the time period. Thus in some embodiments, aqueous culture medium is not flowed through the bioreactor after inoculation.

Bioreactors equipped with devices such as spinning blades and impellers, rocking mechanisms, stir bars, means for pressurized gas infusion can be used to subject microalgal cultures to mixing. Mixing may be continuous or intermittent. For example, in some embodiments, a turbulent flow regime of gas entry and media entry is not maintained until a desired increase in number of said microalgae has been achieved.

Bioreactor ports can be used to introduce, or extract, gases, solids, semisolids, and liquids, into the bioreactor chamber containing the microalgae. While many bioreactors have more than one port (for example, one for media entry, and another for sampling), it is not necessary that only one substance enter or leave a port. For example, a port can be used to flow culture media into the bioreactor and later used for sampling, gas entry, gas exit, or other purposes. Preferably, a sampling port can be used repeatedly without altering compromising the axenic nature of the culture. A sampling port can be configured with a valve or other device that allows the flow of sample to be stopped and started or to provide a means of continuous sampling. Bioreactors typically have at least one port that allows inoculation of a culture, and such a port can also be used for other purposes such as media or gas entry.

Bioreactors ports allow the gas content of the culture of microalgae to be manipulated. To illustrate, part of the volume of a bioreactor can be gas rather than liquid, and the gas inlets of the bioreactor to allow pumping of gases into the bioreactor. Gases that can be beneficially pumped into a bioreactor include air, air/$CO_2$ mixtures, noble gases, such as argon, and other gases. Bioreactors are typically equipped to enable the user to control the rate of entry of a gas into the bioreactor. As noted above, increasing gas flow into a bioreactor can be used to increase mixing of the culture.

Increased gas flow affects the turbidity of the culture as well. Turbulence can be achieved by placing a gas entry port below the level of the aqueous culture media so that gas entering the bioreactor bubbles to the surface of the culture. One or more gas exit ports allow gas to escape, thereby preventing pressure buildup in the bioreactor. Preferably a gas exit port leads to a "one-way" valve that prevents contaminating microorganisms from entering the bioreactor.

3. Media

Microalgal culture media typically contains components such as a fixed nitrogen source, a fixed carbon source, trace elements, optionally a buffer for pH maintenance, and phosphate (typically provided as a phosphate salt). Other components can include salts such as sodium chloride, particularly for seawater microalgae. Nitrogen sources include organic and inorganic nitrogen sources, including, for example, without limitation, molecular nitrogen, nitrate, nitrate salts, ammonia (pure or in salt form, such as, $(NH_4)_2SO_4$ and $NH_4OH$), protein, soybean meal, cornsteep liquor, and yeast extract. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$.

Solid and liquid growth media are generally available from a wide variety of sources, and instructions for the preparation of particular media that is suitable for a wide variety of strains of microorganisms can be found, for example, from the culture collection of algae (UTEX) maintained by the University of Texas at Austin, 1 University Station A6700, Austin, Tex., 78712-0183For example, various fresh water and salt water media include those described in PCT Pub. No. 2008/151149, incorporated herein by reference.

In a particular example, Proteose Medium is suitable for axenic cultures, and a 1 L volume of the medium (pH ~6.8) can be prepared by addition of 1 g of proteose peptone to 1 liter of Bristol Medium. Bristol medium comprises 2.94 mM NaNO$_3$, 0.17 mM CaCl$_2$.2H$_2$O, 0.3 mM MgSO$_4$.7H$_2$O, 0.43 mM, 1.29 mM KH$_2$PO$_4$, and 1.43 mM NaCl in an aqueous solution. For 1.5% agar medium, 15 g of agar can be added to 1 L of the solution. The solution is covered and autoclaved, and then stored at a refrigerated temperature prior to use. Another example is the *Prototheca* isolation medium (PIM), which comprises 10 g/L potassium hydrogen phthalate (KHP), 0.9 g/L sodium hydroxide, 0.1 g/L magnesium sulfate, 0.2 g/L potassium hydrogen phosphate, 0.3 g/L ammonium chloride, 10 g/L glucose 0.001 g/L thiamine hydrochloride, 20 g/L agar, 0.25 g/L 5-fluorocytosine, at a pH in the range of 5.0 to 5.2 (see Pore, 1973, App. Microbiology, 26: 648-649). Other suitable media for use with the methods of the invention can be readily identified by consulting the URL identified above, or by consulting other organizations that maintain cultures of microorganisms, such as SAG, CCAP, or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCALA refers to the culture collection of algal laboratory at the Institute of Botany (Třeboň, Czech Republic). Additionally, U.S. Pat. No. 5,900,370 describes media formulations and conditions suitable for heterotrophic fermentation of *Prototheca* species.

For oil production, selection of a fixed carbon source is important, as the cost of the fixed carbon source must be sufficiently low to make oil production economical. In one embodiment, the fixed carbon source is xylose. Xylose is a five-carbon monosaccharide that is found as a component of hemicellulose. Hemicellulose is a complex polysaccharide that is found in almost all plant cell walls, comprising about 30% of all plant matter. In addition to xylose, other carbon sources can be included, for example, acetate, floridoside, fructose, galactose, glucuronic acid, glucose, glycerol, lactose, mannose, N-acetylglucosamine, rhamnose, sucrose, and/or xylose, selection of feedstocks containing those compounds, particularly xylose, is an important aspect of the methods of the invention.

Other suitable feedstocks useful in accordance with the methods of the invention include, for example, black liquor, corn starch, depolymerized cellulosic material, milk whey, molasses, potato, sorghum, sucrose, sugar beet, sugar beet juice, sugar cane, sugar cane juice, thick cane juice, rice, and wheat. Carbon sources can also be provided as a mixture, such as a mixture of sucrose or xylose and depolymerized sugar beet pulp, depolymerized cellulosic material and the like. The one or more carbon source(s) can be supplied at a concentration of at least about 50 μM, at least about 100 μM, at least about 250 μM, at least about 500 μM, at least about 1 mM, at least about 2.5 mM, at least about 5 mM, at least about 10 mM, at least about 25 mM, at least about 50 mM, at least about 100 mM, at least 250 mM, and at least about 500 mM, of one or more exogenously provided fixed carbon source(s). In some cases, one or more carbon source(s) can be supplied, as a feedstock for fed-batch fermentation, at a concentration of at least about 100 g/L, of at least about 200 g/L, of at least about 300 g/L of at least about 400 g/L, at least about 500 g/L, at least about 600 g/L, at least about 700 g/L, at least about 800 g/L or more or the exogenously provided fixed carbon source(s) into the fermentation culture. Carbon sources of particular interest for purposes of the present invention include xylose, depolymerized cellulosic material, glycerol, glucose, sucrose, and sorghum, each of which is discussed in more detail below.

In accordance with the present invention, microorganisms can be cultured using depolymerized cellulosic biomass as a feedstock. Cellulosic biomass (e.g., stover, such as corn stover) is inexpensive and readily available. Microalgae can grow on processed cellulosic material, and microalgae of the invention are especially designed to utilize xylose as a carbon source with high efficiency. Cellulosic materials generally include about 40-60% cellulose; about 20-40% hemicellulose; and 10-30% lignin.

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and miscanthus, fiber cane, and fiber sorghum. Five-carbon sugars that are produced from such materials include xylose.

Cellulosic materials may be treated to increase the efficiency with which the microbe can utilize the sugar(s) contained within the materials. As discussed above, lignocellulosic biomass is comprised of various fractions, including cellulose, a crystalline polymer of beta 1,4 linked glucose (a six-carbon sugar), hemicellulose, a more loosely associated polymer predominantly comprised of xylose (a five-carbon sugar) and to a lesser extent mannose, galactose, arabinose, lignin, a complex aromatic polymer comprised of sinapyl alcohol and its derivatives, and pectins, which are linear chains of an alpha 1,4 linked polygalacturonic acid. Because of the polymeric structure of cellulose and hemicellulose, the sugars (e.g., monomeric glucose and xylose) in them are not in a form that can be efficiently used (metabolized) by many microbes. For such microbes, further processing of the cellulosic biomass to generate the monomeric sugars that make up the polymers can be very helpful to ensuring that the cellulosic materials are efficiently utilized as a feedstock (carbon source).

Cellulose or cellulosic biomass can be subjected to a process, termed "explosion", in which the biomass is treated with dilute sulfuric (or other) acid at elevated temperature and pressure. This process conditions the biomass such that it can be efficiently subjected to enzymatic hydrolysis of the cellulosic and hemicellulosic fractions into glucose and xylose monomers. The resulting monomeric sugars are termed cellulosic sugars. Cellulosic sugars can subsequently be utilized by microorganisms to produce a variety of metabolites (e.g., lipid). The acid explosion step results in a partial hydrolysis of the hemicellulose fraction to constituent monosaccharides. These sugars can be completely liberated from the biomass with further treatment. In some embodiments, the further treatment is a hydrothermal treatment that includes washing the exploded material with hot water, which removes contaminants such as salts. This step is not necessary for cellulosic ethanol fermentations due to the more dilute sugar concentrations used in such processes. In other embodiments, the further treatment is additional acid treatment. In still other embodiments, the further treatment is enzymatic hydrolysis of the exploded material. These treatments can also be used in any combination. The type of treatment can affect the type of sugars liberated (e.g., five carbon sugars versus six carbon sugars) and the stage at which they are liberated in the process. As a consequence, different streams of sugars, whether they are predominantly five-carbon or six-carbon, can be created. These enriched five-carbon or six-carbon streams can thus be directed to specific microorganisms with different carbon utilization cabilities. In certain embodiments of the methods of the present invention, five-carbon xylose enriched streams are preferred. In other embodiments, different sugar streams containing five-carbon sugars, six-carbon sugars, or a combination of five-carbon/six carbon sugars that have been saccharified, can be combined for use in microbial fermentation to produce high cell density lipid-producing microbial biomass.

Embodiments of the present invention related to lipid production may involve fermentation to higher cell densities than what is achieved in ethanol fermentation. Because of the higher densities of the cultures for heterotrophic cellulosic oil production, the fixed carbon source (e.g., the cellulosic derived sugar stream(s)) is preferably in a concentrated form. For example, the glucose concentration, or the xylose concentration, or the sum of glucose and xylose concentration of the depolymerized cellulosic material can be at least about 100 g/liter, at least about 200 g/liter, at least about 300 g/liter, at least about 400 g/liter, at least about 500 g/liter at least about 600 g/liter at least about 700 g/liter, at least about 800 g/liter or more of glucose or xylose or a combination of glucose and xylose in the feedstock prior to the cultivation step, which is optionally a fed batch cultivation in which the material is fed to the cells over time as the cells grow and accumulate lipid. Various methods for such saccharification methods and other methods for processing cellulosics for use in microalgal fermentations are described in U.S. Patent Application Publication 20100151112.

The explosion process treatment of the cellulosic material utilizes significant amounts of sulfuric acid, heat and pressure, thereby liberating by-products of carbohydrates, namely furfurals and hydroxymethyl furfurals. Furfurals and hydroxymethyl furfurals are produced during hydrolysis of hemicellulose through dehydration of xylose into furfural and water. While this loss of xylose is not desired in many embodiments of the methods of the present invention, such that either a non-explosion process is employed or the production of furfurals and hydroxymethyl furfurals is minimized when they are used, these by-products (e.g., furfurals and hydroxymethyl furfurals) can be removed from the saccharified lignocellulosic material prior to introduction into the bioreactor, and the conductivities of the cellulosic materials resulting from the explosion process can be reduced by methods described in U.S. Patent Application Publication 20100151112.

In other embodiments, the explosion process itself is changed so as to avoid the generation of salts at unacceptably high levels. For example, a suitable alternative to sulfuric acid (or other acid) explosion of the cellulosic biomass is mechanical pulping to render the cellulosic biomass receptive to enzymatic hydrolysis (saccharification). In still other embodiments, native strains of microorganisms resistant to high levels of salts or genetically engineered strains with resistance to high levels of salts are used. A non-limiting example of a method of treating cellulosic sugars so that it is suitable for use as a concentrated feedstock for the present invention is described in U.S. Patent Application Publication 20100151538, hereby incorporated by reference. In one embodiment, the saccharified lignocellulosic sugars have been treated to reduce both the toxins (e.g., furfurals and hydroxymethyl furfurals) and the salt level and then concentrated to a concentration of at least 600 g/L or more sugar monomer in the concentrated sugar stream or fixed carbon source feedstock. In other embodiments, such concentrated saccharified lignocellulosic sugars have a salt level of less than 700 mM sodium equivalents. In other embodiments, such concentrated saccharified lignocellulosic sugars have a salt level of less than 100 mM sodium equivalents, less than 200 mM sodium equivalents, less than 300 mM sodium equivalents, less than 400 mM sodium equivalents, less than 500 mM sodium equivalents, less than 600 mM sodium equivalents, less than 700 mM sodium equivalents, or less than 1000 mM sodium equivalents, In still other embodiments, such concentrated saccharified lignocellulosic sugar feedstock has a conductivity of less than 20,000 µS/cm, less than 15,000 µS/cm, less than 10,000 µS/cm, less than 7,500 µS/cm, less than 5,000 µS/cm, less than 1000 µS/cm, less than 500 µS/cm, less than 300 µS/cm, or less than 200 µS/cm of conductivity. In still other embodiments, such concentrated saccharified lignocellulosic sugar feedstock have been enriched for five carbon sugar monomers, or six carbon sugar mononers, or a combination of five and six carbon sugar monomers.

In another embodiment of the methods of the invention, the carbon source includes glycerol, such as acidulated and non-acidulated glycerol byproduct from biodiesel transesterification. In one embodiment, the carbon source includes glycerol and xylose. In some cases, all of the glycerol and the xylose are provided to the microorganism at the beginning of the fermentation. In some cases, the glycerol and the xylose are provided to the microorganism simultaneously at a predetermined ratio. In some cases, the glycerol and the xylose are fed to the microbes at a predetermined rate over the course of fermentation.

Some microalgae undergo cell division faster in the presence of glycerol than in the presence of another carbon source, such as glucose (see PCT Pub. No. 2008/151149). In instances where this is true for glycerol and xylose, two-stage growth processes in which cells are first fed glycerol to rapidly increase cell density, and are then fed xylose to accumulate lipids can improve the efficiency with which lipids are produced. The use of the glycerol byproduct of the transesterification process provides significant economic advantages when put back into the production process. Other feeding methods are provided as well, such as mixtures of glycerol and xylose. Feeding such mixtures also captures the same economic benefits. Thus, the invention provides methods of feeding alternative sugars to microalgae such as xylose in various combinations with glycerol.

In various embodiments of the methods of the invention, the carbon source is xylose, including a complex feedstock containing xylose, such as a cellulosics-derived material. In one embodiment, the culture medium further includes at least one xylose utilization enzyme. The use of complex feedstocks containing xylose can provide significant cost savings in the production of hydrocarbons and other oils.

4. Oil Production

For the production of oil in accordance with the methods of the invention, it is preferable to culture cells in the dark (or in the substantial absence of light), as is the case, for example, when using extremely large (40,000 liter and higher) fermentors that do not allow light to strike the culture. Obligate heterotroph species such as species of *Prototheca* are grown and propagated for the production of oil in a medium containing a fixed carbon source and in the absence of light; such growth is known as heterotrophic growth.

As an example, an inoculum of lipid-producing microalgal cells are introduced into the medium; there is a lag period (lag phase) before the cells begin to propagate. Following the lag period, the propagation rate increases steadily and enters the log, or exponential, phase. The exponential phase is in turn followed by a slowing of propagation due to decreases in nutrients such as nitrogen, increases in toxic substances, and quorum sensing mechanisms. After this slowing, propagation stops, and the cells enter a stationary phase or steady growth state, depending on the particular environment provided to the cells. For obtaining lipid rich biomass, the culture is typically harvested well after the end of the exponential phase, which may be terminated early by allowing nitrogen or another key nutrient (other than carbon) to become depleted, forcing the cells to convert the carbon sources, present in excess, to lipid. Culture condition parameters can be manipulated to optimize total oil production, the combination of lipid species produced, and/or production of a specific oil.

As discussed above, a bioreactor or fermentor is used to allow cells to undergo the various phases of their growth cycle. As an example, an inoculum of lipid-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells. Lipid production by cells disclosed herein can occur during the log phase or thereafter, including the stationary phase wherein nutrients are supplied, or still available, to allow the continuation of lipid production in the absence of cell division.

Preferably, microorganisms grown using conditions described herein and known in the art comprise at least about 20% by weight of lipid, at least about 40% by weight, at least about 50% by weight, at least about 60% by weight, and at least about 70% by weight. Process conditions can be adjusted to increase the yield of lipids suitable for a particular use and/or to reduce production cost. For example, in certain embodiments, a microalgae is cultured in the presence of a limiting concentration of one or more nutrients, such as, for example, nitrogen, phosphorous, or sulfur, while providing an excess of fixed carbon energy such as glucose. Nitrogen limitation tends to increase microbial lipid yield over microbial lipid yield in a culture in which nitrogen is provided in excess. In particular embodiments, the increase in lipid yield is at least about: 10%, 50%, 100%, 200%, or 500% greater than obtained under nitrogen replete conditions. The microbe can be cultured in the presence of a limiting amount of a nutrient for a portion of the total culture period or for the entire period. In particular embodiments, the nutrient concentration is cycled between a limiting concentration and a non-limiting concentration at least twice during the total culture period. Lipid content of cells can be increased by continuing the culture for increased periods of time while providing an excess of carbon, but limiting or no nitrogen.

In another embodiment, lipid yield is increased by culturing a lipid-producing microbe (e.g., microalgae) in the presence of one or more cofactor(s) for a lipid pathway enzyme (e.g., a fatty acid synthetic enzyme). Generally, the concentration of the cofactor(s) is sufficient to increase microbial lipid (e.g., fatty acid) yield over microbial lipid yield in the absence of the cofactor(s). In a particular embodiment, the cofactor(s) are provided to the culture by including in the culture a microbe (e.g., microalgae) containing an exogenous gene encoding the cofactor(s). Alternatively, cofactor(s) may be provided to a culture by including a microbe (e.g., microalgae) containing an exogenous gene that encodes a protein that participates in the synthesis of the cofactor. In certain embodiments, suitable cofactors include any vitamin required by a lipid pathway enzyme, such as, for example: biotin, pantothenate. Genes encoding cofactors suitable for use in the invention or that participate in the synthesis of such cofactors are well known and can be introduced into microbes (e.g., microalgae), using contructs and techniques such as those described above.

The specific examples of bioreactors, culture conditions, and heterotrophic growth and propagation methods described herein can be combined in any suitable manner to improve efficiencies of microbial growth and lipid and/or protein production.

Microalgal biomass with a high percentage of oil/lipid accumulation by dry weight has been generated using different methods of culture, which are known in the art (see PCT Pub. No. 2008/151149). Microalgal biomass generated by the culture methods described herein and useful in accordance with the present invention comprises at least 10% microalgal oil by dry weight. In some embodiments, the microalgal biomass comprises at least 25%, at least 50%, at least 55%, at least 60% microalgal oil, or at least 70% microalgal oil by dry weight. In some embodiments, the microalgal biomass contains from 10-90% microalgal oil, from 25-75% microalgal oil, from 40-75% microalgal oil, or from 50-70% microalgal oil by dry weight.

The microalgal oil of the biomass described herein, or extracted from the biomass for use in the methods and compositions of the present invention can comprise glycerolipids with one or more distinct fatty acid ester side chains. Glycerolipids are comprised of a glycerol molecule esterified to one, two or three fatty acid molecules, which can be of varying lengths and have varying degrees of saturation. The length and saturation characteristics of the fatty acid molecules (and the microalgal oils) can be manipulated to modify the properties or proportions of the fatty acid molecules in the microalgal oils of the present invention via culture conditions or via lipid pathway engineering, as described in more detail in Section V, below. Thus, specific blends of algal oil can be prepared either within a single species of algae by mixing together the biomass or algal oil from two or more species of microalgae, or by blending algal oil of the invention with oils from other sources such as soy, rapeseed, canola, palm, palm kernel, coconut, corn, waste vegetable, Chinese tallow, olive, sunflower, cottonseed, chicken fat, beef tallow, porcine tallow, microalgae, macroalgae, microbes, Cuphea, flax, peanut, choice white grease, lard, *Camelina sativa*, mustard seed, cashew nut, oats, lupine, kenaf, calendula, help, coffee, linseed (flax), hazelnut, euphorbia, pumpkin seed, coriander, camellia, sesame, safflower, rice, tung tree, cocoa, copra, pium poppy, castor beans, pecan, jojoba, macadamia, Brazil nuts, avocado, petroleum, or a distillate fraction of any of the preceding oils.

The oil composition, i.e., the properties and proportions of the fatty acid constituents of the glycerolipids, can also be manipulated by combining biomass or oil from at least two distinct species of microalgae. In some embodiments, at least two of the distinct species of microalgae have different glycerolipid profiles. The distinct species of microalgae can be cultured together or separately as described herein, preferably under heterotrophic conditions, to generate the respective oils. Different species of microalgae can contain different percentages of distinct fatty acid constituents in the cell's glycerolipids.

Generally, wild type *Protheca* strains have very little or no fatty acids with the chain length C8-C14. For example, *Prototheca moriformis* (UTEX 1435), *Prototheca krugani* (UTEX 329), *Prototheca stagnora* (UTEX 1442) and *Prototheca zopfii* (UTEX 1438) contains no (or undectable amounts) C8 fatty acids, between 0-0.01% C10 fatty acids, between 0.03-2.1% C12 fatty acids and between 1.0-1.7% C14 fatty acids.

Microalgal oil can also include other constituents produced by the microalgae, or incorporated into the microalgal oil from the culture medium. These other constituents can be present in varying amount depending on the culture conditions used to culture the microalgae, the species of microalgae, the extraction method used to recover microalgal oil from the biomass and other factors that may affect microalgal oil composition. Non-limiting examples of such constituents include carotenoids, present from 0.1-0.4 micrograms/ml, chlorophyll present from 0-0.02 milligrams/kilogram of oil, gamma tocopherol present from 0.4-0.6 milligrams/100 grams of oil, and total tocotrienols present from 0.2-0.5 milligrams/gram of oil.

The other constituents can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-cryptoxanthin), and various organic or inorganic compounds.

In some cases, the oil extracted from *Prototheca* species comprises no more than 0.02 mg/kg chlorophyll. In some cases, the oil extracted from *Prototheca* species comprises no more than 0.4 mcg/ml total carotenoids. In some cases the *Prototheca* oil comprises between 0.40-0.60 milligrams of gamma tocopherol per 100 grams of oil. In other cases, the *Prototheca* oil comprises between 0.2-0.5 milligrams of total tocotrienols per gram of oil.

IV. Genetic Engineering Methods and Materials

Embodiments of the present invention provide methods and materials for genetically modifying cells and recombinant host cells useful in the methods of the present invention, including but not limited to recombinant oleaginous microorganisms, microalgae, and oleaginous microalgae such as *Prototheca moriformis*, *Prototheca zopfii*, *Prototheca krugani*, and *Prototheca stagnora* host cells. The description of these methods and materials is divided into subsections for the convenience of the reader. In subsection 1, transformation methods are described. In subsection 2, homologous recombination methods are described. In subsection 3, expression vectors and vector components are described.

1. Transformation Methods

Cells can be transformed by any suitable technique including, e.g., biolistics, electroporation (see Maruyama et al. (2004), Biotechnology Techniques 8:821-826), glass bead transformation and silicon carbide whisker transformation. Another method that can be used involves forming protoplasts and using $CaCl_2$ and polyethylene glycol (PEG) to introduce recombinant DNA into microalgal cells (see Kim et al. (2002), *Mar. Biotechnol.* 4:63-73, which reports the use of this method for the transformation of *Chorella ellipsoidea*). Co-transformation of microalgae can be used to introduce two distinct vector molecules into a cell simultaneously (see for example Protist 2004 December; 155(4):381-93).

Biolistic methods (see, for example, Sanford, Trends In Biotech. (1988) 6:299 302, U.S. Pat. No. 4,945,050; electroporation (Fromm et al., Proc. Nat'l. Acad. Sci. (USA) (1985) 82:5824 5828); use of a laser beam, microinjection or any other method capable of introducing DNA into a microalgae can also be used for transformation of a *Prototheca* cell.

2. Homologous Recombination Methods

Homologous recombination refers to the ability of complementary DNA sequences in a host cell to align and exchange regions of homology. Transgenic DNA ("donor") containing sequences homologous to the genomic sequences being targeted ("template") is introduced into the host cell and then undergoes recombination into the genome at the site of the corresponding genomic homologous sequences. The mechanistic steps of this process, in most cases, include: (1) pairing of homologous DNA segments; (2) introduction of double-stranded breaks into the donor DNA molecule; (3) invasion of the template DNA molecule by the free donor DNA ends followed by DNA synthesis; and (4) resolution of double-strand break repair events that result in final recombination products.

The ability to carry out homologous recombination in a host organism has many practical implications for what can be carried out at the molecular genetic level and is useful in the generation of an oleaginous microbe that can produced tailored oils. By its very nature homologous recombination is a precise gene targeting event; hence, most transgenic lines generated with the same targeting sequence will be essentially identical in terms of phenotype, necessitating the screening of far fewer transformation events. Homologous recombination also targets gene insertion events into the host chromosome, resulting in excellent genetic stability, even in the absence of genetic selection. Because different chromosomal loci can impact gene expression, even from heterologous promoters/UTRs, homologous recombination can be a method of querying loci in an unfamiliar genome environment and to assess the impact of these environments on gene expression.

Particularly useful genetic engineering applications using homologous recombination is to co-opt specific host regulatory elements such as promoters/UTRs to drive heterologous gene expression in a highly specific fashion. For example, precise ablation of the endogenous stearoyl ACP desaturase gene with a heterologous C12:0 specific FATB (thioesterase) gene cassette and suitable selective marker, might be expected to dramatically decrease endogenous levels of C18:1 fatty acids concomitant with increased levels of the C12:0 fatty acids. See U.S. Patent Application Publication 20100151112.

Because homologous recombination is a precise gene targeting event, it can be used to modify any nucleotide(s) within a gene or region of interest precisely, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, and thus affecting the desired change in metabolism of the host cell. Homologous recombination provides a powerful means to manipulate the gost genome resulting in gene targeting, gene conversion, gene deletion, gene duplication, gene inversion, and the exchange of gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/ region of interest, or can flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

3. Vectors and Vector Components

Vectors for transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to (or contains) one or more control sequences that regulate gene expression or target the gene product to a particular location in the recombinant cell. To aid the reader, this subsection is divided into subsections. Subsection A describes control sequences typically contained on vectors as well as control sequences for use particularly in microalgae such as *Prototheca*. Subsection B describes genes typically contained in vectors as well as codon optimization methods and genes prepared using them for use particularly in microalgae, such as *Prototheca*.

A. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of an exogenous gene in a microalgae contains a coding sequence for a desired gene product (for example, a selectable marker, a lipid pathway modification enzyme, or a xylose utilization enzyme) in operable linkage with a promoter active in microalgae. Alternatively, if the vector does not contain a promoter in operable linkage with the coding sequence of interest, the coding sequence can be transformed into the cells such that it becomes operably linked to an endogenous promoter at the point of vector integration.

Many promoters are active in microalgae, including promoters that are endogenous to the algae being transformed, as well as promoters that are not endogenous to the algae being transformed (i.e., promoters from other algae, promoters from higher plants, and promoters from plant viruses or algae viruses). Illustrative exogenous and/or endogenous promoters that are active in microalgae (as well as antibiotic resistance genes functional in microalgae) are described in PCT Pub. No. 2008/151149 and references cited therein). See also U.S. Patent Application Publication 20100151112.

The promoter used to express an exogenous gene can be the promoter naturally linked to that gene or can be a heterologous promoter. Some promoters are active in more than one species of microalgae. Other promoters are species-specific. Illustrative promoters include promoters such as β-tubulin from *Chlamydomonas reinhardtii*, used in the Examples below, and viral promoters, such as cauliflower mosaic virus (CMV) and *chlorella* virus, which have been shown to be active in multiple species of microalgae (see for example Plant Cell Rep. 2005 March; 23(10-11):727-35; J. Microbiol. 2005 August; 43(4):361-5; Mar Biotechnol (NY). 2002 January; 4(1):63-73). Another promoter that is suitable for use for expression of exogenous genes in *Prototheca* is the *Chlorella sorokiniana* glutamate dehydrogenase promoter/5'UTR (SEQ ID NO: 10). Optionally, at least 10, 20, 30, 40, 50, or 60 nucleotides or more of these sequences containing a promoter are used. Illustrative promoters useful for expression of exogenous genes in *Prototheca* are listed in the sequence listing of this application, such as the promoter of the *Chlorella* HUP1 gene (SEQ ID NO:11) and the *Chlorella ellipsoidea* nitrate reductase promoter (SEQ ID NO:12). *Chlorella* virus promoters can also be used to express genes in *Prototheca*, such as SEQ ID NOs: 1-7 of U.S. Pat. No. 6,395,965. Additional promoters active in *Prototheca* can be found, for example, in Biochem Biophys Res Commun. 1994 Oct. 14; 204(1):187-94; Plant Mol. Biol. 1994 October; 26(1):85-93; Virology. 2004 Aug. 15; 326(1):150-9; and Virology. 2004 Jan. 5; 318 (1):214-23.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule (e.g, glucose, as in SEQ ID NO:11), temperature (heat or cold), lack of nitrogen in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is be primarily one of convenience, as the termination region is relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

The present invention also provides control sequences and recombinant genes and vectors containing them that provide for the compartmentalized expression of a gene of interest. Organelles for targeting are chloroplasts, plastids, mitochondria, and endoplasmic reticulum. In addition, the present invention provides control sequences and recombinant genes and vectors containing them that provide for the secretion of a protein outside the cell.

Proteins expressed in the nuclear genome of *Prototheca* can be targeted to the plastid using plastid targeting signals. Plastid targeting sequences endogenous to *Chlorella* are known, such as genes in the *Chlorella* nuclear genome that encode proteins that are targeted to the plastid; see for example GenBank Accession numbers AY646197 and AF499684, and in one embodiment, such control sequences are used in the vectors of the present invention to target expression of a protein to a *Prototheca* plastid.

The use of algal plastid targeting sequences to target heterologous proteins to the correct compartment in the host cell has been described. See Examples 11 and 12 of U.S. Patent Application Publication 20100151112. In one embodiment the native plastid targeting sequence of the heterologous protein is used to traffic the heterologous protein to the plastid/chloroplast. In some embodiment, the native plastid targeting sequences are replaced with heterologous plastid targeting sequences in order to increase the trafficking of the recombinant or heterologous proteins into the plastid/chloroplast. In some embodiments, native plastid targeting sequences are replaced with plastid targeting sequences of microalgal proteins. Sequences were BLASTed and analyzed for homology to known proteins that traffic to the plastid/chloroplast. The cDNAs encoding these proteins were cloned and plastid targeting sequences were isolated from these cDNAs. Such algal plastid targeting sequences can be used in expression vectors useful in the cells and methods of the invention.

In another embodiment of the present invention, the expression of a polypeptide in *Prototheca* is targeted to the endoplasmic reticulum. The inclusion of an appropriate retention or sorting signal in an expression vector ensure that proteins are retained in the endoplasmic reticulum (ER) and do not go downstream into Golgi. For example, the IMPACTVECTOR1.3 vector, from Wageningen UR-Plant Research International, includes the well known KDEL retention or sorting signal. With this vector, ER retention has a practical advantage in that it has been reported to improve expression levels 5-fold or more. The main reason for this appears to be that the ER contains lower concentrations and/or different proteases responsible for post-translational degradation of expressed proteins than are present in the cytoplasm. ER retention signals functional in green microalgae are known. For example, see Proc Natl Acad Sci USA. 2005 Apr. 26; 102(17):6225-30.

In another embodiment of the present invention, a polypeptide is targeted for secretion outside the cell into the culture media. See Hawkins et al., Current Microbiology Vol. 38 (1999), pp. 335-341 for examples of secretion signals active in *Chlorella* that can be used, in accordance with the methods of the invention, in *Prototheca*.

B. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated, in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, and its corresponding gene product, is called a selectable marker. Selectable markers can be employed in a transgene construct useful for transforming *Prototheca*. Examples of suitable selectable markers include the G418 resistance gene, the nitrate reductase gene (see Dawson et al. (1997), Current Microbiology 35:356-362), the hygromycin phosphotransferase gene (HPT; see Kim et al. (2002), Mar. Biotechnol. 4:63-73), the neomycin phosphotransferase gene, and the ble gene, which confers resistance to phleomycin (Huang et al. (2007), Appl. Microbiol. Biotechnol. 72:197-205). Methods of determining sensitivity of microalgae to antibiotics are well known. For example, Mol Gen Genet. 1996 Oct. 16; 252(5):572-9.

For purposes of the present invention, the expression vector used to prepare a recombinant host cell of embodiments of the invention can include at least two, and often three, genes, if one of the genes is a selectable marker. For example, a genetically engineered *Prototheca* of the invention can be made by transformation with vectors of the invention that comprise, in addition to a selectable marker, one or more exogenous genes, such as, for example, a xylose utilization gene or a xylose utilization gene and an acyl ACP-thioesterase gene. One or both genes can be expressed using an inducible promoter, which allow the relative timing of expression of these genes to be controlled to enhance the lipid yield and conversion to fatty acid esters. Expression of the two or more exogenous genes may be under control of the same inducible promoter or under control of different inducible (or constitutive) promoters. In the latter situation, expression of a first exogenous gene can be induced for a first period of time (during which expression of a second exogenous gene may or may not be induced) and expression of a second exogenous gene can be induced for a second period of time (during which expression of a first exogenous gene may or may not be induced).

In other embodiments, the two or more exogenous genes (in addition to any selectable marker) are a xylose utilization gene, a fatty acyl-ACP thioesterase, a keto-acyl-ACP synthase, a steroyl-ACP desturase, a fatty acid desaturase, and a fatty acyl-CoA/aldehyde reductase, the combined action of which yields an alcohol product. Further provided are other combinations of exogenous genes in addition to the xylose utilization gene, including without limitation, a fatty acyl-ACP thioesterase and a fatty acyl-CoA reductase to generate aldehydes. In one embodiment, the vector provides, in addition to the xylose utilization gene, for the combination of a fatty acyl-ACP thioesterase, a fatty acyl-CoA reductase, and a fatty aldehyde decarbonylase to generate alkanes. In each of these embodiments, one or more of the exogenous genes can be expressed using an inducible promoter.

Other illustrative vectors that express two or more exogenous genes include those encoding both a xylose utilization enzyme and a selectable marker. The recombinant *Prototheca* transformed with vectors of the invention can be used to produce lipids at lower manufacturing cost due to the engineered ability to use xylose as a carbon source. Insertion of exogenous genes as described above can be combined with the disruption of polysaccharide biosynthesis through directed and/or random mutagenesis, which steers even greater carbon flux into lipid production. Individually and in combination, trophic conversion, engineering to alter lipid production, and treatment with exogenous enzymes alter the lipid composition produced by a microorganism. The alteration can be a change in the amount of lipids produced, the amount of one or more hydrocarbon species produced relative to other lipids, and/or the types of lipid species produced in the microorganism. For example, microalgae can be engineered to produce a higher amount and/or percentage of TAGs.

For optimal expression of a recombinant protein, it is beneficial to employ coding sequences that produce mRNA with codons preferentially used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA.

The present invention provides codon-optimized nucleic acids useful for the successful expression of recombinant proteins in *Prototheca*. Codon usage in *Prototheca* species was analyzed by studying cDNA sequences isolated from *Prototheca moriformis*. This analysis represents the interrogation over 24,000 codons and resulted in Table 1 below.

TABLE 1

Preferred codon usage in Prototheca strains.

| Ala | GCG | 345 (0.36) | Asn | AAT | 8 (0.04) |
|---|---|---|---|---|---|
|  | GCA | 66 (0.07) |  | AAC | 201 (0.96) |
|  | GCT | 101 (0.11) | Pro | CCG | 161 (0.29) |
|  | GCC | 442 (0.46) |  | CCA | 49 (0.09) |
| Cys | TGT | 12 (0.10) |  | CCT | 71 (0.13) |
|  | TGC | 105 (0.90) |  | CCC | 267 (0.49) |
| Asp | GAT | 43 (0.12) | Gln | CAG | 226 (0.82) |
|  | GAC | 316 (0.88) |  | CAA | 48 (0.18) |
| Glu | GAG | 377 (0.96) | Arg | AGG | 33 (0.06) |
|  | GAA | 14 (0.04) |  | AGA | 14 (0.02) |
| Phe | TTT | 89 (0.29) |  | CGG | 102 (0.18) |
|  | TTC | 216 (0.71) |  | CGA | 49 (0.08) |
| Gly | GGG | 92 (0.12) |  | CGT | 51 (0.09) |
|  | GGA | 56 (0.07) |  | CGC | 331 (0.57) |
|  | GGT | 76 (0.10) | Ser | AGT | 16 (0.03) |
|  | GGC | 559 (0.71) |  | AGC | 123 (0.22) |
| His | CAT | 42 (0.21) |  | TCG | 152 (0.28) |
|  | CAC | 154 (0.79) |  | TCA | 31 (0.06) |
| Ile | ATA | 4 (0.01) |  | TCT | 55 (0.10) |
|  | ATT | 30 (0.08) |  | TCC | 173 (0.31) |
|  | ATC | 338 (0.91) | Thr | ACG | 184 (0.38) |
| Lys | AAG | 284 (0.98) |  | ACA | 24 (0.05) |
|  | AAA | 7 (0.02) |  | ACT | 21 (0.05) |
| Leu | TTG | 26 (0.04) |  | ACC | 249 (0.52) |
|  | TTA | 3 (0.00) | Val | GTG | 308 (0.50) |
|  | CTG | 447 (0.61) |  | GTA | 9 (0.01) |
|  | CTA | 20 (0.03) |  | GTT | 35 (0.06) |
|  | CTT | 45 (0.06) |  | GTC | 262 (0.43) |
|  | CTC | 190 (0.26) | Trp | TGG | 107 (1.00) |
| Met | ATG | 191 (1.00) | Tyr | TAT | 10 (0.05) |
|  |  |  |  | TAC | 180 (0.95) |
|  |  |  | Stop | TGA/TAG/TAA |  |

In other embodiments, the gene in the recombinant vector has been codon-optimized with reference to a microalgal strain other than a *Prototheca* strain. For example, methods of recoding genes for expression in microalgae are described in U.S. Pat. No. 7,135,290. Additional information for codon optimization is available, e.g., at the codon usage database of GenBank.

While the methods and materials of the invention allow for the introduction of any exogenous gene into *Prototheca*, genes relating to xylose utilization and lipid pathway modification are of particular interest, as discussed in the following sections.

V. Xylose Utilization

An embodiment of the present invention also provides recombinant oleaginous microbes that have been modified to alter the ability of the microbe to metabolize different feedstocks that include pentose sugars such as xylose, which is abundant in cellulosic sources. Such recombinant oleaginous microbes include those that have plastids and type II fatty acid synthesis pathways, are of the kingdom Plantae, microalgae, oleaginous yeast, oleaginous bacteria and oleaginous fungi.

In some embodiments, the recombinant oleaginous microbe is a microalgae. In other embodiments, the recombinant oleaginous microbe is a microalgae of the genus *Prototheca*. In one embodiment, the recombinant oleaginous microbe is genetically engineered to contain one or more exogenous genes that are involved in xylose utilization. Genes involved in xylose utilization are described in detail below. It is contemplated in one or more embodiments of the invention that the genes involved in xylose utilization can be used alone, or in combination with other genes that involve xylose utilization, without limit to the number or combination(s) of such genes. It is contemplated in one or more embodiments of the invention that genes involved in xylose utilization can be used in combination with other exogenous genes that involve utilization of other carbon sources or lipid production, without limit to the number or combination(s) of such genes.

In one embodiment, the recombinant cell of the invention further contains one or more exogenous xylose utilization genes. There are at least two different pathways utilized by eukaryotic organisms to metabolize xylose. One such pathway is the oxo-reductive (oxidoreductase) pathway or aldo keto reductase pathway. In the first step in this pathway, D-xylose is reduced into xylitol by xylose reductase. Xylitol is then oxidized into xylulose by xylitol dehydrogenase. Xylulose is then converted into xylulose-5-phosphate by xylulose kinase and then metabolized via the pentose phosphate pathway. Another pathway that is utilized to metabolize xylose is the xylose isomerase pathway. In the first step in the xylose isomerase pathway, xylose is isomerized into xylulose by xylose isomerase. Xylulose is then converted into xylulose-5-phosphate by xyulose kinase. Xylulose-5-phosphate is then metabolized via the pentose phosphate pathway.

In some organisms, one or more of these pathways exist and are utilized in concert. In some organisms, both the oxo-reductive pathway and the xylose isomerase pathways exist. In such organisms, the production of xylitol may inhibit xylose isomerase activity. In such cases, xylitol dehydrogenase is expressed to relieve such inhibition.

In organisms that do not utilize xylose, or are unable to utilize xylose in an efficient manner, one or both of the above pathways may not exist or only exist partially in these organisms. Genetically engineering such organisms to efficiently utilize xylose may encompass the introduction of one or several (or all) members of one or both of these pathways. The introduction of a transporter protein may be necessary to transport xylose or more efficiently transport xylose into the cell from the extracellular environment. A transporter protein, including a transporter protein that has specificity for pentose sugars such as xylose, is a family of cell membrane proteins and genes encoding such proteins that transport sugars (such as xylose) from the extracellular environment, such as the culture medium, into the cytosol of the cell. A transporter may be active or passive. Passive transporters facilitate the transport of molecule(s) down a concentration gradient (from an area of higher concentration to an area of lower concentration) without energy consumption. In some embodiments, the transporter is a pentose transporter, having specificity for pentose sugars. In other embodiments, the transporter is a transporter derived from *Pichia stipitis*. In still other embodiments, the transporter is derived from *Pichia stipitis* SUT1 (without limitation, GenBank Accession number XP_001387, hereby incorporated by this reference) (SEQ ID NO: 37), SUT2, and/or SUT3 transporters or from the *S. cerevisiae* HXT transporters. Active transporters consume energy in transporting molecules, usually against a concentration gradient. Active transporters include, without limitation, primary active transporters, which use ATP as an energy source, i.e., ATP-binding cassette (ABC) transporters, and secondary active transporters, which use energy from chemiosmotic gradients and include, without limitation antiporters and symporters, i.e., the GXS1 protein (SEQ ID NO: 39) of *Candida intermedia* (without limitation, GenBank Accession number CAI44932.1, hereby incorporated by this reference), and the H+-symporter-like proteins (e.g., SEQ ID NO: 41). In some embodiments, the transporter is derived from the At5g59250n gene from *Arabidopsis*. In other embodiments, the transporter is derived from the gene encoding the XLT1 protein (SEQ ID NO: 43) from *Trichoderma reesei*.

Additionally, the introduction of a transporter protein (e.g., xylulose-5-phosphate translocator) may also be necessary or preferred in order to distribute the correct substrate into the correct subcompartment of the microbe. Pentose sugar metabolism is thought to occur through the pentose phosphate pathway, which occurs mainly in the plastid. Such translocators are a family of plastidic membrane proteins and genes encoding such proteins that transport hexose, triose, or pentose or phosphate versions of these molecules from the cytosol to the plastid. In one embodiment, such a translocator has a preference for pentose or pentose phosphate molecules over hexose/hexose phosphate or triose/triose phosphate. In another embodiment, the translocator is derived from a gene encoding a xylulose 5-phosphate translocator protein. In another embodiment, the translocator is derived from the XPT gene from *Arabidopsis*. In some cases, the translocator is a chimeric protein comprising a transit peptide endogenous to the microbe being engineered to utilize xylose. For example, chimeric translocators with a transit peptide endogenous to *Prototheca* (e.g., SEQ ID NOs: 45, 47 and 49) are useful in some embodiments.

In some embodiments, the heterologous exogenous gene that is introduced into the microorganism is a part of the oxo-reductive or aldo keto reductase pathway. In some cases, the heterologous exogenous gene is a xylose reductase. In other cases, the heterologous exogenous gene is a xylitol dehydrogenase. In other embodiments, the xylitol dehydrogenase is the XYL2 gene from *Pichia stipitis*.

In other embodiments, the heterologous exogenous gene that is introduced into the microorganism is part of the xylose isomerase pathway. In some cases, the heterologous exogenous gene is a xylose isomerase. In some embodiments, the xylose isomerase is encoded by the XYLA gene from *Piromyces* sp. In other embodiments, the heterologous exogenous gene is a xylulose kinase. In some embodiments, the xylulose kinase is encoded by the XYL3 gene from *Pichia stipitis*.

In some embodiments, the heterologous exogenous gene encodes a translocator protein. In other embodiments, such translocator is a pentose phosphate translocator. In still other embodiments, the pentose phosphate translocator is encoded by the XPT gene from *Arabidopsis thaliana*. In still other embodiments, the genetically engineered microorganism comprises one or more of the foregoing exogenous heterologous genes. In other embodiments, the genetically engineered microorganism comprises all of the foregoing exogenous heterologous genes.

Example 3 below demonstrates the successful introduction of different members of the xylose isomerase pathway proteins, oxo-reductive pathway enzymes, and a xylose translocator into microalgae to produce a genetically engineered microalgae cells that can utilize xylose as a fixed carbon source when grown under heterotrophic conditions.

Example 7 demonstrates the introduction of various combinations of xylose transporters, xylose oxidoreductase/isomerase enzymes, and xylose translocators (see Table 6) into *Prototheca*. Example 8 demonstrates the lipid production capability of several selected strains.

In some embodiments, the cell may further contain one or more exogenous sucrose utilization genes, as described in U.S. Patent Application Publication 20100151112. Such a cell can metabolize both xylose and sucrose.

VI. Lipid Pathway Engineering

In addition to altering the ability of *Prototheca* to utilize feedstocks such as xylose-containing feedstocks, the present invention also provides recombinant *Prototheca* that have been further modified to alter the properties and/or proportions of lipids produced. The pathway can further, or alternatively, be modified to alter the properties and/or proportions of various lipid molecules produced through enzymatic processing of lipids and intermediates in the fatty acid pathway. In various embodiments, the recombinant *Prototheca* cells of the invention have, relative to their untransformed counterparts, optimized lipid yield per unit volume and/or per unit time, carbon chain length (e.g., for renewable diesel production or for industrial chemicals applications requiring lipid feedstock), reduced number of double or triple bonds, optionally to zero, and increasing the hydrogen:carbon ratio of a particular species of lipid or of a population of distinct lipid.

In particular embodiments, one or more key enzymes that control metabolism to fatty acid synthesis have been "up-regulated" or "down-regulated" to improve lipid production. Up-regulation can be achieved, for example, by transforming cells with expression constructs in which a gene encoding the enzyme of interest is expressed, e.g., using a strong promoter and/or enhancer elements that increase transcription. Such constructs can include a selectable marker such that the transformants can be subjected to selection, which can result in maintenance or amplification of the construct and an increase in the expression level of the encoded enzyme. Examples of enzymes suitable for up-regulation according to the methods of the invention are described in U.S. Patent Application Publication 20100151112.

Up- and/or down-regulation of genes can be applied to global regulators controlling the expression of the genes of the fatty acid biosynthetic pathways. Accordingly, one or more global regulators of fatty acid synthesis can be up- or down-regulated, as appropriate, to inhibit or enhance, respectively, the expression of a plurality of fatty acid synthetic genes and, ultimately, to increase lipid production. Examples include sterol regulatory element binding proteins (SREBPs), such as SREBP-1a and SREBP-1c (for examples see Genbank accession numbers NP_035610 and Q9WTN3).

Embodiments of the present invention also provide recombinant microalgal cells that have been modified to contain one or more exogenous genes encoding lipid modification enzymes such as, for example, fatty acyl-ACP thioesterases, fatty acyl-CoA/aldehyde reductases, fatty acyl-CoA reductases, fatty aldehyde decarbonylase, fatty aldehyde reductases, and squalene synthases (see U.S. Patent Application Publication 20100151112).

Thus, in particular embodiments, microbes of the present invention are genetically engineered to express a xylose utilization gene as well as one or more exogenous genes selected from an acyl-ACP thioesterase, an acyl-CoA/aldehyde reductase, a fatty acyl-CoA reductase, a fatty aldehyde reductase, a fatty aldehyde decarbonylase, or a naturally co-expressed acyl carrier protein. Suitable expression methods are described above with respect to the expression of a lipase gene, including, among other methods, inducible expression and compartmentalized expression. A fatty acyl-ACP thioesterase cleaves a fatty acid from an acyl carrier protein (ACP) during lipid synthesis. Through further enzymatic processing, the cleaved fatty acid is then combined with a coenzyme to yield an acyl-CoA molecule. This acyl-CoA is the substrate for the enzymatic activity of a fatty acyl-CoA reductase to yield an aldehyde, as well as for a fatty acyl-CoA/aldehyde reductase to yield an alcohol. The aldehyde produced by the action of the fatty acyl-CoA reductase identified above is the substrate for further enzymatic activity by either a fatty aldehyde reductase to yield an alcohol, or a fatty aldehyde decarbonylase to yield an alkane or alkene.

In some embodiments, fatty acids, glycerolipids, or the corresponding primary alcohols, aldehydes, alkanes or alkenes, generated by the methods described herein, contain 8, 10, 12, or 14 carbon atoms. Preferred fatty acids for the production of diesel, biodiesel, renewable diesel, or jet fuel, or the corresponding primary alcohols, aldehydes, alkanes and alkenes, for industrial applications contain 8 to 14 carbon atoms. In certain embodiments, the above fatty acids, as well as the other corresponding hydrocarbon molecules, are saturated (with no carbon-carbon double or triple bonds); mono unsaturated (single double bond); poly unsaturated (two or more double bonds); are linear (not cyclic) or branched. For fuel production, greater saturation is preferred.

The enzymes described directly above have a preferential specificity for hydrolysis of a substrate containing a specific number of carbon atoms. For example, a fatty acyl-ACP thioesterase may have a preference for cleaving a fatty acid having 12 carbon atoms from the ACP. In some embodiments, the ACP and the length-specific thioesterase may have an affinity for one another that makes them particularly useful as a combination (e.g., the exogenous ACP and thioesterase genes may be naturally co-expressed in a particular tissue or organism from which they are derived). Therefore, in various embodiments, a recombinant cell of an embodiment of the invention can contain an exogenous gene that encodes a protein with specificity for catalyzing an enzymatic activity (e.g., cleavage of a fatty acid from an ACP, reduction of an acyl-CoA to an aldehyde or an alcohol, or conversion of an aldehyde to an alkane, or the gene product of a KAS, SAD, or FAD gene) with regard to the number of carbon atoms and saturation pattern contained in the substrate. See U.S. Patent Application Publication 20100151112 for various vectors and methods for expressing an exogenous thioesterase. Thus, in an embodiment of the present invention a genetically modified cell both metabolizes xylose and produces an altered fatty acid profile (i.e. distribution of chain length and/or saturation pattern in fatty acids produced by the cell).

Thus, the present invention provides a cell (and in specific embodiments, a *Prototheca* cell) that has been genetically engineered to express a xylose utilization enzyme and one or more lipid pathway enzymes at an altered level compared to a wild-type cell of the same species. In some cases, the cell produces more lipid compared to the wild-type cell when both cells are grown under the same conditions. In some cases, the cell has been genetically engineered and/or selected to express a lipid pathway enzyme at a higher level than the wild-type cell. In some cases, the lipid pathway enzyme is selected from the group consisting of pyruvate dehydrogenase, acetyl-CoA carboxylase, acyl carrier protein, and glycerol-3 phosphate acyltransferase. In some cases, the cell has been genetically engineered and/or selected to express a lipid pathway enzyme at a lower level than the wild-type cell. In at least one embodiment in which the cell expresses the lipid pathway enzyme at a lower level, the lipid pathway enzyme comprises citrate synthase.

In some embodiments, the cell has been genetically engineered and/or selected to express a global regulator of fatty acid synthesis at an altered level compared to the wild-type cell, whereby the expression levels of a plurality of fatty acid synthetic genes are altered compared to the wild-type cell. In some cases, the lipid pathway enzyme comprises an enzyme that modifies a fatty acid. In some cases, the lipid pathway enzyme is selected from a stearoyl-ACP desaturase and a glycerolipid desaturase.

In other embodiments, the present invention is directed to an oil-producing microbe containing one or more exogenous genes, wherein the exogenous genes encode protein(s) selected from xylose utilization enzymes as well as proteins selected from the group consisting of a fatty acyl-ACP thioesterase, a fatty acyl-CoA reductase, a fatty aldehyde reductase, a fatty acyl-CoA/aldehyde reductase, a fatty aldehyde decarbonylase, and an acyl carrier protein. In one embodiment, the exogenous gene is in operable linkage with a promoter, that is inducible or repressible in response to a stimulus. In some cases, the stimulus is selected from the group consisting of an exogenously provided small molecule, heat, cold, and limited or no nitrogen in the culture media. In some cases, the exogenous gene is expressed in a cellular compartment. In some embodiments, the cellular compartment is selected from the group consisting of a chloroplast, a plastid and a mitochondrion. In some embodiments the microbe is *Prototheca moriformis, Prototheca krugani, Prototheca stagnora* or *Prototheca zopfii*. Various exogenous gene and gene combinations for lipid pathway modification are described in U.S. Patent Application Publication 20100151112.

An embodiment of the present invention also provides methods for producing an alcohol comprising culturing a population of recombinant *Prototheca* cells in a culture medium, wherein the cells contain a first exogenous gene encoding a xylose utilization enzyme; a second exogenous gene encoding a fatty acyl-ACP thioesterase; and a third exogenous gene encoding a fatty acyl-CoA/aldehyde reductase, and the cells synthesize a fatty acid linked to an acyl carrier protein (ACP), the fatty acyl-ACP thioesterase catalyzes the cleavage of the fatty acid from the ACP to yield, through further processing, a fatty acyl-CoA, and the fatty acyl-CoA/aldehyde reductase catalyzes the reduction of the acyl-CoA to an alcohol.

An embodiment of the present invention also provides methods of producing an aldehyde in a *Prototheca* cell. In one embodiment, the method comprises culturing a population of *Prototheca* cells in a culture medium, wherein the cells contain a first exogenous gene encoding a xylose utilization enzyme; a second exogenous gene encoding a fatty acyl-ACP thioesterase; and a third exogenous gene encoding a fatty acyl-CoA reductase, and the cells synthesize a fatty acid linked to an acyl carrier protein (ACP), the fatty acyl-ACP thioesterase catalyzes the cleavage of the fatty acid from the ACP to yield, through further processing, a fatty acyl-CoA, and the fatty acyl-CoA reductase catalyzes the reduction of the acyl-CoA to an aldehyde.

An embodiment of the present invention also provides methods of producing a fatty acid molecule having a specified carbon chain length in a *Prototheca* cell that contains an exogenous xylose utilization gene. In one embodiment, the method comprises culturing a population of lipid-producing *Prototheca* cells in a culture medium, wherein the microbes contain an exogenous gene encoding an exogenous xylose utilization gene and a fatty acyl-ACP thioesterase having an activity specific or preferential to a certain carbon chain length, such as 8, 10, 12 or 14 carbon atoms, and wherein the microbes synthesize a fatty acid linked to an acyl carrier protein (ACP) and the thioesterase catalyzes the cleavage of the fatty acid from the ACP when the fatty acid has been synthesized to the specific carbon chain length.

In the various embodiments described above, the cell can contain at least one exogenous gene encoding a lipid pathway enzyme. In some cases, the lipid pathway enzyme is selected from the group consisting of a stearoyl-ACP desaturase, a glycerolipid desaturase, a pyruvate dehydrogenase, an acetyl-CoA carboxylase, an acyl carrier protein, and a glycerol-3 phosphate acyltransferase. In other cases, the cell contains a lipid modification enzyme selected from the group consisting of a fatty acyl-ACP thioesterase, a fatty acyl-CoA/aldehyde reductase, a fatty acyl-CoA reductase, a fatty aldehyde reductase, a fatty aldehyde decarbonylase, and/or an acyl carrier protein.

VII. Production of Fuels and Chemicals or Other Products

For the production of fuel in accordance with the embodiments of the invention lipids produced by cells of the invention are harvested, or otherwise collected, by any convenient means. Lipids can be isolated by whole cell extraction. The cells are first disrupted, and then intracellular and cell membrane/cell wall-associated lipids as well as extracellular hydrocarbons can be separated from the cell mass, such as by use of centrifugation as described above. Intracellular lipids produced in microorganisms are, in some embodiments, extracted after lysing the cells of the microorganism. Once extracted, the lipids are further refined to produce oils, fuels, or oleochemicals.

After completion of culturing, the microorganisms can be separated from the fermentation broth. Optionally, the separation is effected by centrifugation to generate a concentrated paste. The biomass can then optionally be washed with a washing solution (e.g., DI water) to get rid of the fermentation broth and debris. Optionally, the washed microbial biomass may also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Microorganisms containing a lipid can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes, using ultrasound, mechanical lysis, using osmotic shock, infection with a lytic virus, and/or expression of one or more lytic genes. Lysis is performed to release intracellular molecules which have been produced by the microorganism. Each of these methods for lysing a microorganism can be used as a single method or in combination simultaneously or sequentially. The extent of cell disruption can be observed by microscopic analysis. Using one or more of the methods described herein, typically more than 70% cell breakage is observed. Preferably, cell breakage is more than 80%, more preferably more than 90% and most preferred about 100%.

In particular embodiments, the microorganism is lysed after growth, for example to increase the exposure of cellular lipid and/or hydrocarbon for extraction or further processing. The timing of lipase expression (e.g., via an inducible promoter) or cell lysis can be adjusted to optimize the yield of lipids and/or hydrocarbons. Below are described a number of lysis techniques. These techniques can be used individually or in combination.

In one embodiment of the present invention, the step of lysing a microorganism comprises heating of a cellular suspension containing the microorganism. In this embodiment, the fermentation broth containing the microorganisms (or a suspension of microorganisms isolated from the fermentation broth) is heated until the microorganisms, i.e., the cell walls and membranes of microorganisms degrade or breakdown. Typically, temperatures applied are at least 50° C. Higher temperatures, such as at least 60° C., at least 70° C., at least 80° C., at least 90° C., at least 100° C., at least 110° C., at least 120° C., at least 130° C. or higher are used for more efficient cell lysis. Lysing cells by heat treatment can be performed by boiling the microorganism. Alternatively, heat treatment (without boiling) can be performed in an autoclave. The heat treated lysate may be cooled for further treatment. Cell disruption can also be performed by steam treatment, i.e., through addition of pressurized steam. Steam treatment of microalgae for cell disruption is described, for example, in U.S. Pat. No. 6,750,048. In some embodiments, steam treatment may be achieved by sparging steam into the fermentor and maintaining the broth at a desired temperature for less than about 90 minutes, preferably less than about 60 minutes, and more preferably less than about 30 minutes.

In another embodiment of the present invention, the step of lysing a microorganism comprises adding a base to a cellular suspension containing the microorganism. The base should be strong enough to hydrolyze at least a portion of the proteinaceous compounds of the microorganisms used. Bases which are useful for solubilizing proteins are known in the art of chemistry. Exemplary bases which are useful in the methods of the present invention include, but are not limited to, hydroxides, carbonates and bicarbonates of lithium, sodium, potassium, calcium, and mixtures thereof. A preferred base is KOH. Base treatment of microalgae for cell disruption is described, for example, in U.S. Pat. No. 6,750,048.

In another embodiment of the present invention, the step of lysing a microorganism comprises adding an acid to a cellular suspension containing the microorganism. Acid lysis can be effected using an acid at a concentration of 10-500 mN or preferably 40-160 mN. Acid lysis is preferably performed at above room temperature (e.g., at 40-160°, and preferably a temperature of 50-130°. For moderate temperatures (e.g., room temperature to 100° C. and particularly room temperature to 65°, acid treatment can usefully be combined with sonication or other cell disruption methods.

In another embodiment of the present invention, the step of lysing a microorganism comprises lysing the microorganism by using an enzyme. Preferred enzymes for lysing a microorganism are proteases and polysaccharide-degrading enzymes such as hemicellulase (e.g., hemicellulase from *Aspergillus niger*; Sigma Aldrich, St. Louis, Mo.; #H2125), pectinase (e.g., pectinase from *Rhizopus* sp.; Sigma Aldrich, St. Louis, Mo.; #P2401), Mannaway 4.0 L (Novozymes), cellulase (e.g., cellulose from *Trichoderma viride*; Sigma Aldrich, St. Louis, Mo.; #C9422), and driselase (e.g., driselase from *Basidiomycetes* sp.; Sigma Aldrich, St. Louis, Mo.; #D9515.

In other embodiments of the present invention, lysis is accomplished using an enzyme such as, for example, a cellulase such as a polysaccharide-degrading enzyme, optionally from *Chlorella* or a *Chlorella* virus, or a proteases, such as *Streptomyces griseus* protease, chymotrypsin, proteinase K, proteases listed in Degradation of Polylactide by Commercial Proteases, Oda Y et al., Journal of Polymers and the Environment, Volume 8, Number 1, January 2000, pp. 29-32 (4), Alcalase 2.4 FG (Novozymes), and Flavourzyme 100 L (Novozymes). Any combination of a protease and a polysaccharide-degrading enzyme can also be used, including any combination of the preceding proteases and polysaccharide-degrading enzymes.

Lysis can be performed using an expeller press. In this process, biomass is forced through a screw-type device at high pressure, lysing the cells and causing the intracellular lipid to be released and separated from the protein and fiber (and other components) in the cell. See PCT patent application number U.S. Ser. No. 10/031,108, incorporated herein by reference.

In some cases, the step of lysing a microorganism is performed by using ultrasound, i.e., sonication. Thus, cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension.

In some cases, the step of lysing a microorganism is performed by mechanical lysis. Cells can be lysed mechanically and optionally homogenized to facilitate hydrocarbon (e.g., lipid) collection. For example, a pressure disrupter can be used to pump a cell containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules. Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring blender as examples), the french press, or even centrifugation in case of weak cell walls, to disrupt cells.

In some cases, the step of lysing a microorganism is performed by applying an osmotic shock.

In some cases, the step of lysing a microorganism comprises infection of the microorganism with a lytic virus. A wide variety of viruses are known to lyse microorganisms suitable for use in the present invention, and the selection and use of a particular lytic virus for a particular microorganism is within the level of skill in the art. For example, *paramecium bursaria chlorella* virus (PBCV-1) is the prototype of a group (family Phycodnaviridae, genus *Chlorovirus*) of large, icosahedral, plaque-forming, double-stranded DNA viruses that replicate in, and lyse, certain unicellular, eukaryotic *chlorella*-like green algae. Accordingly, any susceptible microalgae can be lysed by infecting the culture with a suitable *Chlorella* virus. Methods of infecting species of *Chlorella* with a *chlorella* virus are known. See for example *Adv. Virus Res.* 2006; 66:293-336; *Virology,* 1999 Apr. 25; 257(1):15-23; *Virology,* 2004 Jan. 5; 318(1):214-23; *Nucleic Acids Symp. Ser.* 2000; (44):161-2; *J. Virol.* 2006 March; 80(5): 2437-44; and *Annu. Rev. Microbiol.* 1999; 53:447-94.

In some cases, the step of lysing a microorganism comprises autolysis. In this embodiment, a microorganism according to the invention is genetically engineered to produce a lytic protein that will lyse the microorganism. This lytic gene can be expressed using an inducible promoter so that the cells can first be grown to a desirable density in a fermentor, followed by induction of the promoter to express the lytic gene to lyse the cells. In one embodiment, the lytic gene encodes a polysaccharide-degrading enzyme. In certain other embodiments, the lytic gene is a gene from a lytic virus. Thus, for example, a lytic gene from a *Chlorella* virus can be expressed in an algal cell; see Virology 260, 308-315 (1999); *FEMS Microbiology Letters* 180 (1999) 45-53; *Virology* 263, 376-387 (1999); and *Virology* 230, 361-368 (1997). Expression of lytic genes is preferably done using an inducible promoter, such as a promoter active in microalgae that is induced by a stimulus such as the presence of a small molecule, light, heat, and other stimuli.

Various methods are available for separating lipids from cellular lysates produced by the above methods. For example, lipids and lipid derivatives such as fatty aldehydes, fatty alcohols, and hydrocarbons such as alkanes, can be extracted with a hydrophobic solvent such as hexane (see Frenz et al. 1989, Enzyme Microb. Technol., 11:717). Lipids and lipid derivatives can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12): 1735-1738); and supercritical $CO_2$ extraction (see for example Mendes et al. 2003, Inorganica Chimica Acta 356: 328-334). Miao and Wu describe a protocol of the recovery of microalgal lipid from a culture of *Chlorella prototheocoides* in which the cells were harvested by centrifugation, washed with distilled water and dried by freeze drying. The resulting cell powder was pulverized in a mortar and then extracted with n-hexane. Miao and Wu, Biosource Technology (2006) 97:841-846.

Thus, lipids, lipid derivatives and hydrocarbons generated by the microorganisms of the present invention can be recovered by extraction with an organic solvent. In some cases, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid or hydrocarbon components. Hexane extraction methods are well known in the art.

Lipids and lipid derivatives such as fatty aldehydes, fatty alcohols, and hydrocarbons such as alkanes produced by cells as described herein can be modified by the use of one or more enzymes, including a lipase, as described above. When the hydrocarbons are in the extracellular environment of the cells, the one or more enzymes can be added to that environment under conditions in which the enzyme modifies the hydrocarbon or completes its synthesis from a hydrocarbon precursor. Alternatively, the hydrocarbons can be partially, or completely, isolated from the cellular material before addition of one or more catalysts such as enzymes. Such catalysts are exogenously added, and their activity occurs outside the cell or in vitro.

Thus, lipids and hydrocarbons produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon and triglyceride oil processing. Catalytic methods involve the use of a catalyst, such as a solid acid catalyst. For example, the catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size. An elevated temperature of about 800° C. and pressure of about 700 kPa can be used. These conditions generate "light," a term that is sometimes used to refer to hydrogen-rich hydrocarbon molecules (as distinguished from photon flux), while also generating, by condensation, heavier hydrocarbon molecules which are relatively depleted of hydrogen. The methodology provides homolytic, or symmetrical, breakage and produces alkenes, which may be optionally enzymatically saturated as described above.

Catalytic and thermal methods are standard in plants for hydrocarbon processing and oil refining. Thus hydrocarbons produced by cells as described herein can be collected and processed or refined via conventional means. See Hillen et al. (Biotechnology and Bioengineering, Vol. XXIV: 193-205 (1982)) for a report on hydrocracking of microalgae-produced hydrocarbons. In alternative embodiments, the fraction is treated with another catalyst, such as an organic compound, heat, and/or an inorganic compound. For processing of lipids into biodiesel, a transesterification process can be used as described in Section V herein.

Hydrocarbons produced via methods of the present invention are useful in a variety of industrial applications. For example, the production of linear alkylbenzene sulfonate (LAS), an anionic surfactant used in nearly all types of detergents and cleaning preparations, utilizes hydrocarbons generally comprising a chain of 10-14 carbon atoms. See, for example, U.S. Pat. Nos. 6,946,430; 5,506,201; 6,692,730; 6,268,517; 6,020,509; 6,140,302; 5,080,848; and 5,567,359. Surfactants, such as LAS, can be used in the manufacture of personal care compositions and detergents, such as those described in U.S. Pat. Nos. 5,942,479; 6,086,903; 5,833,999; 6,468,955; and 6,407,044.

Increasing interest is directed to the use of hydrocarbon components of biological origin in fuels, such as biodiesel, renewable diesel, and jet fuel, because renewable biological starting materials that may replace starting materials derived from fossil fuels are available, and the use thereof is desirable. There is an urgent need for methods for producing hydrocarbon components from biological materials. The present invention fulfills this need by providing methods for production of biodiesel, renewable diesel, and jet fuel using the lipids generated by the methods described herein as a biological material to produce biodiesel, renewable diesel, and jet fuel.

Traditional diesel fuels are petroleum distillates rich in paraffinic hydrocarbons. They have boiling ranges as broad as 370° to 780° F., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Technically, any hydrocarbon distillate material derived from biomass or otherwise that meets the appropriate ASTM specification can be defined as diesel fuel (ASTM D975), jet fuel (ASTM D1655), or as biodiesel if it is a fatty acid methyl ester (ASTM D6751).

After extraction, lipid and/or hydrocarbon components recovered from the microbial biomass described herein can be subjected to chemical treatment to manufacture a fuel for use in diesel vehicles and jet engines.

Biodiesel is a liquid which varies in color—between golden and dark brown—depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear. Typically, biodiesel comprises C14-C18 alkyl esters. Various processes convert biomass or a lipid produced and isolated as described herein to diesel fuels. A preferred method to produce biodiesel is by transesterification of a lipid as described herein. A preferred alkyl ester for use as biodiesel is a methyl ester or ethyl ester.

Biodiesel produced by a method described herein can be used alone or blended with conventional diesel fuel at any concentration in most modern diesel-engine vehicles. When blended with conventional diesel fuel (petroleum diesel), biodiesel may be present from about 0.1% to about 99.9%. Much of the world uses a system known as the "B" factor to state the amount of biodiesel in any fuel mix. For example, fuel containing 20% biodiesel is labeled B20. Pure biodiesel is referred to as B100.

Biodiesel can also be used as a heating fuel in domestic and commercial boilers. Existing oil boilers may contain rubber parts and may require conversion to run on biodiesel. The conversion process is usually relatively simple, involving the exchange of rubber parts for synthetic parts due to biodiesel being a strong solvent. Due to its strong solvent power, burning biodiesel will increase the efficiency of boilers. Biodiesel can be used as an additive in formulations of diesel to increase the lubricity of pure Ultra-Low Sulfur Diesel (ULSD) fuel, which is advantageous because it has virtually no sulfur content. Biodiesel is a better solvent than petrodiesel and can be used to break down deposits of residues in the fuel lines of vehicles that have previously been run on petrodiesel.

Biodiesel can be produced by transesterification of triglycerides contained in oil-rich biomass. Thus, in another aspect of the present invention a method for producing biodiesel is provided. In a preferred embodiment, the method for producing biodiesel comprises the steps of (a) cultivating a lipid-containing microorganism using methods disclosed herein (b) lysing a lipid-containing microorganism to produce a lysate, (c) isolating lipid from the lysed microorganism, and (d) transesterifying the lipid composition, whereby biodiesel is produced. Methods for growth of a microorganism, lysing a microorganism to produce a lysate, treating the lysate in a medium comprising an organic solvent to form a heterogeneous mixture and separating the treated lysate into a lipid composition have been described above and can also be used in the method of producing biodiesel.

The lipid profile of the biodiesel is usually highly similar to the lipid profile of the feedstock oil. Other oils provided by the methods and compositions of the invention can be subjected to transesterification to yield biodiesel with lipid profiles including (a) at least 4% C8-C14; (b) at least 0.3% C8; (c) at least 2% C10; (d) at least 2% C12; and (3) at least 30% C8-C14.

Lipid compositions can be subjected to transesterification to yield long-chain fatty acid esters useful as biodiesel. Preferred transesterification reactions are outlined below and include base catalyzed transesterification and transesterification using recombinant lipases. In a base-catalyzed transesterification process, the triacylglycerides are reacted with an alcohol, such as methanol or ethanol, in the presence of an alkaline catalyst, typically potassium hydroxide. This reaction forms methyl or ethyl esters and glycerin (glycerol) as a byproduct.

Animal and plant oils are typically made of triglycerides which are esters of free fatty acids with the trihydric alcohol, glycerol. In transesterification, the glycerol in a triacylglyceride (TAG) is replaced with a short-chain alcohol such as methanol or ethanol. A typical reaction scheme is as follows:

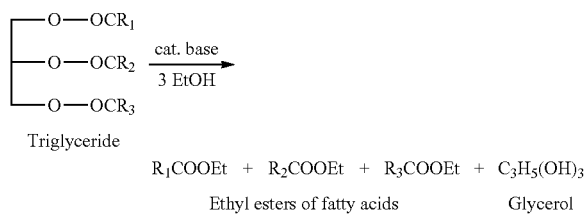

In this reaction, the alcohol is deprotonated with a base to make it a stronger nucleophile. Commonly, ethanol or methanol is used in vast excess (up to 50-fold). Normally, this reaction will proceed either exceedingly slowly or not at all. Heat, as well as an acid or base can be used to help the reaction proceed more quickly. The acid or base are not consumed by the transesterification reaction, thus they are not reactants but catalysts. Almost all biodiesel has been produced using the base-catalyzed technique as it requires only low temperatures and pressures and produces over 98% conversion yield (provided the starting oil is low in moisture and free fatty acids).

Transesterification has also been carried out, as discussed above, using an enzyme, such as a lipase instead of a base. Lipase-catalyzed transesterification can be carried out, for example, at a temperature between the room temperature and 80° C., and a mole ratio of the TAG to the lower alcohol of greater than 1:1, preferably about 3:1. Lipases suitable for use in transesterification include, but are not limited to, those listed in Table 7. Other examples of lipases useful for transesterification are found in, e.g. U.S. Pat. Nos. 4,798,793; 4,940,845; 5,156,963; 5,342,768; 5,776,741 and WO89/01032. Such lipases include, but are not limited to, lipases produced by microorganisms of *Rhizopus, Aspergillus, Candida, Mucor, Pseudomonas, Rhizomucor, Candida*, and *Humicola* and pancreas lipase. Lipases suitable for use in transesterification are described in Table 7 of U.S. Patent Application Publication 20100151112.

One challenge to using a lipase for the production of fatty acid esters suitable for biodiesel is that the price of lipase is much higher than the price of sodium hydroxide (NaOH) used by the strong base process. This challenge has been addressed by using an immobilized lipase, which can be recycled. However, the activity of the immobilized lipase must be maintained after being recycled for a minimum number of cycles to allow a lipase-based process to compete with the strong base process in terms of the production cost. Immobilized lipases are subject to poisoning by the lower alcohols typically used in transesterification. U.S. Pat. No. 6,398,707 (issued Jun. 4, 2002 to Wu et al.) describes methods for enhancing the activity of immobilized lipases and regenerating immobilized lipases having reduced activity. Some suitable methods include immersing an immobilized lipase in an alcohol having a carbon atom number not less than 3 for a period of time, preferably from 0.5-48 hours, and more preferably from 0.5-1.5 hours. Some suitable methods also include washing a deactivated immobilized lipase with an alcohol having a carbon atom number not less than 3 and then immersing the deactivated immobilized lipase in a vegetable oil for 0.5-48 hours.

In particular embodiments, a recombinant lipase is expressed in the same microorganisms that produce the lipid on which the lipase acts. Suitable recombinant lipases include those listed above in and/or having GenBank Accession numbers listed in Table 7 of U.S. Patent Application Publication 20100151112, or a polypeptide that has at least 70% amino acid identity with one of the lipases listed in that Table 7 and that exhibits lipase activity. In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference as if fully set forth. DNA encoding the lipase and selectable marker is preferably codon-optimized cDNA. Methods of recoding genes for expression in microalgae are described herein and in U.S. Pat. No. 7,135,290.

The common international standard for biodiesel is EN 14214. ASTM D6751 is the most common biodiesel standard referenced in the United States and Canada. Germany uses DIN EN 14214 and the UK requires compliance with BS EN 14214. Basic industrial tests to determine whether the products conform to these standards typically include gas chromatography, HPLC, and others. Biodiesel meeting the quality standards is very non-toxic, with a toxicity rating ($LD_{50}$) of greater than 50 mL/kg.

Although biodiesel that meets the ASTM standards has to be non-toxic, there can be contaminants which tend to crystallize and/or precipitate and fall out of solution as sediment. Sediment formation is particularly a problem when biodiesel is used at lower temperatures. The sediment or precipitates may cause problems such as decreasing fuel flow, clogging fuel lines, clogging filters, and the like. Processes are well-known in the art that specifically deal with the removal of these contaminants and sediments in biodiesel in order to produce a higher quality product. Examples for such processes include, but are not limited to, pretreatment of the oil to remove contaminants such as phospholipids and free fatty acids (e.g., degumming, caustic refining and silica adsorbant filtration) and cold filtration. Cold filtration is a process that was developed specifically to remove any particulates and sediments that are present in the biodiesel after production. This process cools the biodiesel and filters out any sediments or precipitates that might form when the fuel is used at a lower temperature. Such a process is well known in the art and is described in US Patent Application Publication No. 2007-0175091. Suitable methods may include cooling the biodiesel to a temperature of less than about 38° C. so that the impurities and contaminants precipitate out as particulates in the biodiesel liquid. Diatomaceous earth or other filtering material may then added to the cooled biodiesel to form a slurry, which may then filtered through a pressure leaf or other type of filter to remove the particulates. The filtered biodiesel may then be run through a polish filter to remove any remaining sediments and diatomaceous earth, so as to produce the final biodiesel product.

Example 14 of U.S. Patent Application Publication 20100151112 describes the production of biodiesel using triglyceride oil from *Prototheca moriformis*. The Cold Soak Filterability by the ASTM D6751 A1 method of the biodiesel produced in that Example 14 was 120 seconds for a volume of 300 ml. This test involves filtration of 300 ml of B100, which is chilled to 40° F. for 16 hours, allowed to warm to room temp, and filtered under vacuum using 0.7 micron glass fiber filter with stainless steel support. Oils of the invention can be transesterified to generate biodiesel with a cold soak time of less than 120 seconds, less than 100 seconds, and less than 90 seconds.

Subsequent processes may also be used if the biodiesel will be used in particularly cold temperatures. Such processes include winterization and fractionation. Both processes are designed to improve the cold flow and winter performance of the fuel by lowering the cloud point (the temperature at which the biodiesel starts to crystallize). There are several approaches to winterizing biodiesel. One approach is to blend the biodiesel with petroleum diesel. Another approach is to use additives that can lower the cloud point of biodiesel. Another approach is to remove saturated methyl esters indiscriminately by mixing in additives and allowing for the crystallization of saturates and then filtering out the crystals. Fractionation selectively separates methyl esters into individual components or fractions, allowing for the removal or inclusion of specific methyl esters. Fractionation methods include urea fractionation, solvent fractionation and thermal distillation.

Another valuable fuel provided by the methods of the present invention is renewable diesel, which comprises alkanes, such as C10:0, C12:0, C14:0, C16:0 and C18:0 and thus, are distinguishable from biodiesel. High quality renewable diesel conforms to the ASTM D975 standard. The lipids produced by the methods of the present invention can serve as feedstock to produce renewable diesel. Thus, in another aspect of the present invention, a method for producing renewable diesel is provided. Renewable diesel can be produced by at least three processes: hydrothermal processing (hydrotreating); hydroprocessing; and indirect liquefaction. These processes yield non-ester distillates. During these processes, triacylglycerides produced and isolated as described herein, are converted to alkanes.

In one embodiment, the method for producing renewable diesel comprises (a) cultivating a lipid-containing microorganism using methods disclosed herein (b) lysing the microorganism to produce a lysate, (c) isolating lipid from the lysed microorganism, and (d) deoxygenating and hydrotreating the lipid to produce an alkane, whereby renewable diesel is produced. Lipids suitable for manufacturing renewable diesel can be obtained via extraction from microbial biomass using an organic solvent such as hexane, or via other methods, such as those described in U.S. Pat. No. 5,928,696. Some suitable methods may include mechanical pressing and centrifuging. See PCT patent application U.S. Ser. No. 10/031,108, incorporated herein by reference.

In some methods, the microbial lipid is first cracked in conjunction with hydrotreating to reduce carbon chain length and saturate double bonds, respectively. The material is then isomerized, also in conjunction with hydrotreating. The naptha fraction can then be removed through distillation, followed by additional distillation to vaporize and distill components desired in the diesel fuel to meet an ASTM D975 standard while leaving components that are heavier than desired for meeting the D975 standard. Hydrotreating, hydrocracking, deoxygenation and isomerization methods of chemically modifying oils, including triglyceride oils, are well known in the art. See for example European patent applications EP1741768 (A1); EP1741767 (A1); EP1682466 (A1); EP1640437 (A1); EP1681337 (A1); EP1795576 (A1); and U.S. Pat. Nos. 7,238,277; 6,630,066; 6,596,155; 6,977,322; 7,041,866; 6,217,746; 5,885,440; 6,881,873.

In one embodiment of the method for producing renewable diesel, treating the lipid to produce an alkane is performed by hydrotreating of the lipid composition. In hydrothermal processing, typically, biomass is reacted in water at an elevated temperature and pressure to form oils and residual solids. Conversion temperatures are typically 300° to 660° F., with pressure sufficient to keep the water primarily as a liquid, 100 to 170 standard atmospheres (atm). Reaction times are on the order of 15 to 30 minutes. After the reaction is completed, the organics are separated from the water. Thereby a distillate suitable for diesel is produced.

In some methods of making renewable diesel, the first step of treating a triglyceride is hydroprocessing to saturate double bonds, followed by deoxygenation at elevated temperature in the presence of hydrogen and a catalyst. In some methods, hydrogenation and deoxygenation occur in the same reaction. In other methods, deoxygenation occurs before hydrogenation. Isomerization is then optionally performed, also in the presence of hydrogen and a catalyst. Naphtha components are preferably removed through distillation. For examples, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

One suitable method for the hydrogenation of triglycerides includes preparing an aqueous solution of copper, zinc, magnesium and lanthanum salts and another solution of alkali metal or preferably, ammonium carbonate. The two solutions may be heated to a temperature of about 20° C. to about 85° C. and metered together into a precipitation container at rates such that the pH in the precipitation container is maintained between 5.5 and 7.5 in order to form a catalyst. Additional water may be used either initially in the precipitation container or added concurrently with the salt solution and precipitation solution. The resulting precipitate may then be thoroughly washed, dried, calcined at about 300° C. and activated in hydrogen at temperatures ranging from about 100° C. to about 400° C. One or more triglycerides may then be contacted and reacted with hydrogen in the presence of the above-described catalyst in a reactor. The reactor may be a trickle bed reactor, fixed bed gas-solid reactor, packed bubble column reactor, continuously stirred tank reactor, a slurry phase reactor, or any other suitable reactor type known in the art. The process may be carried out either batchwise or in continuous fashion. Reaction temperatures are typically in the range of from about 170° C. to about 250° C. while reaction pressures are typically in the range of from about 300 psig to about 2000 psig. Moreover, the molar ratio of hydrogen to triglyceride in the process of the present invention is typically in the range of from about 20:1 to about 700:1. The process is typically carried out at a weight hourly space velocity (WHSV) in the range of from about 0.1 $hr^{-1}$ to about 5 $hr^{-1}$. One skilled in the art will recognize that the time period required for reaction will vary according to the temperature used, the molar ratio of hydrogen to triglyceride, and the partial pressure of hydrogen. The products produced by such hydrogenation processes include fatty alcohols, glycerol, traces of paraffins and unreacted triglycerides. These products are typically separated by conventional means such as, for example, distillation, extraction, filtration, crystallization, and the like.

Petroleum refiners use hydroprocessing to remove impurities by treating feeds with hydrogen. Hydroprocessing conversion temperatures are typically 300° to 700° F. Pressures are typically 40 to 100 atm. The reaction times are typically on the order of 10 to 60 minutes. Solid catalysts are employed to increase certain reaction rates, improve selectivity for certain products, and optimize hydrogen consumption.

Suitable methods for the deoxygenation of an oil includes heating an oil to a temperature in the range of from about 350° F. to about 550° F. and continuously contacting the heated oil with nitrogen under at least pressure ranging from about atmospheric to above for at least about 5 minutes.

Suitable methods for isomerization include using alkali isomerization and other oil isomerization known in the art.

Hydrotreating and hydroprocessing ultimately lead to a reduction in the molecular weight of the triglyceride feed. The triglyceride molecule is reduced to four hydrocarbon molecules under hydroprocessing conditions: a propane molecule and three heavier hydrocarbon molecules, typically in the C8 to C18 range.

Thus, in one embodiment, the product of one or more chemical reaction(s) performed on lipid compositions of the invention is an alkane mixture that comprises ASTM D975 renewable diesel. Production of hydrocarbons by microorganisms is reviewed by Metzger et al. Appl Microbiol Biotechnol (2005) 66: 486-496 and A Look Back at the U.S. Department of Energy's Aquatic Species Program: Biodiesel from Algae, NREL/TP-580-24190, John Sheehan, Terri Dunahay, John Benemann and Paul Roessler (1998).

The distillation properties of a diesel fuel is described in terms of T10-T90 (temperature at 10% and 90%, respectively, volume distilled). Renewable diesel can be produced from *Prototheca moriformis* triglyceride oil as described in Example 14 of U.S. Patent Application Publication 20100151112. The T10-T90 of the material produced in that Example 14 was 57.9° C. Methods of hydrotreating, isomerization, and other covalent modification of oils disclosed herein, as well as methods of distillation and fractionation (such as cold filtration) disclosed herein, can be employed to generate renewable diesel compositions with other T10-T90 ranges, such as 20, 25, 30, 35, 40, 45, 50, 60 and 65° C. using triglyceride oils produced according to the methods disclosed herein.

The T10 of the material produced in Example 14 of U.S. Patent Application Publication 20100151112 was 242.1° C. Methods of hydrotreating, isomerization, and other covalent modification of oils disclosed herein, as well as methods of distillation and fractionation (such as cold filtration) disclosed herein, can be employed to generate renewable diesel compositions with other T10 values, such as T10 between 180 and 295, between 190 and 270, between 210 and 250, between 225 and 245, and at least 290.

The T90 of the material produced in Example 14 of U.S. Patent Application Publication 20100151112 was 300° C. Methods of hydrotreating, isomerization, and other covalent modification of oils disclosed herein, as well as methods of distillation and fractionation (such as cold filtration) disclosed herein can be employed to generate renewable diesel compositions with other T90 values, such as T90 between 280 and 380, between 290 and 360, between 300 and 350, between 310 and 340, and at least 290.

The FBP of the material produced in Example 14 U.S. Patent Application Publication 20100151112 was 300° C. Methods of hydrotreating, isomerization, and other covalent modification of oils disclosed herein, as well as methods of distillation and fractionation (such as cold filtration) disclosed herein, can be employed to generate renewable diesel compositions with other FBP values, such as FBP between 290 and 400, between 300 and 385, between 310 and 370, between 315 and 360, and at least 300.

Other oils provided by the methods and compositions of the invention can be subjected to combinations of hydrotreating, isomerization, and other covalent modification including oils with lipid profiles including (a) at least 4% C8-C14; (b) at least 0.3% C8; (c) at least 2% C10; (d) at least 2% C12; and (3) at least 30% C8-C14.

A traditional ultra-low sulfur diesel can be produced from any form of biomass by a two-step process. First, the biomass is converted to a syngas, a gaseous mixture rich in hydrogen and carbon monoxide. Then, the syngas is catalytically converted to liquids. Typically, the production of liquids is accomplished using Fischer-Tropsch (FT) synthesis. This technology applies to coal, natural gas, and heavy oils. Thus, in yet another preferred embodiment of the method for producing renewable diesel, treating the lipid composition to produce an alkane is performed by indirect liquefaction of the lipid composition.

The present invention also provides methods to produce jet fuel. Jet fuel is clear to straw colored. The most common fuel is an unleaded/paraffin oil-based fuel classified as Aeroplane A-1, which is produced to an internationally standardized set of specifications. Jet fuel is a mixture of a large number of different hydrocarbons, possibly as many as a thousand or more. The range of their sizes (molecular weights or carbon numbers) is restricted by the requirements for the product, for example, freezing point or smoke point. Kerosone-type Aeroplane fuel (including Jet A and Jet A-1) has a carbon number distribution between about 8 and 16 carbon numbers. Wide-cut or napthatype Aeroplane fuel (including Jet B) typically has a carbon number distribution between about 5 and 15 carbons.

Both Aeroplanes (Jet A and Jet B) may contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient is an example. Corrosion inhibitors, e.g., DCI-4A, can be used for civilian and military fuels and DCI-6A is used for military fuels. FSII agents include, e.g., Di-EGME.

In one embodiment of the invention, a jet fuel is produced by blending algal fuels with existing jet fuel. The lipids produced by the methods of the present invention can serve as feedstock to produce jet fuel. Thus, in another aspect of the present invention, a method for producing jet fuel is provided. Herewith two methods for producing jet fuel from the lipids produced by the methods of the present invention are provided: fluid catalytic cracking (FCC); and hydrodeoxygenation (HDO).

Fluid Catalytic Cracking (FCC) is one method which is used to produce olefins, especially propylene from heavy crude fractions. The lipids produced by the method of the present invention can be converted to olefins. The process involves flowing the lipids produced through an FCC zone and collecting a product stream comprised of olefins, which is useful as a jet fuel. The lipids produced are contacted with a cracking catalyst at cracking conditions to provide a product stream comprising olefins and hydrocarbons useful as jet fuel.

In one embodiment, the method for producing jet fuel comprises (a) cultivating a lipid-containing microalgae in xylose-containing media using *Prototheca* cells and methods disclosed herein, (b) lysing the lipid-containing microorganism to produce a lysate, (c) isolating lipid from the lysate, and (d) treating the lipid composition, whereby jet fuel is produced. In one embodiment of the method for producing a jet fuel, the lipid composition can be flowed through a fluid catalytic cracking zone, which, in one embodiment, may comprise contacting the lipid composition with a cracking catalyst at cracking conditions to provide a product stream comprising $C_2$-$C_5$ olefins.

In certain embodiments of this method, it may be desirable to remove any contaminants that may be present in the lipid composition. Thus, prior to flowing the lipid composition through a fluid catalytic cracking zone, the lipid composition is pretreated. Pretreatment may involve contacting the lipid composition with an ion-exchange resin. The ion exchange resin is an acidic ion exchange resin, such as Amberlyst™-15 and can be used as a bed in a reactor through which the lipid composition is flowed, either upflow or downflow. Other pretreatments may include mild acid washes by contacting the lipid composition with an acid, such as sulfuric, acetic, nitric, or hydrochloric acid. Contacting is done with a dilute acid solution usually at ambient temperature and atmospheric pressure.

The lipid composition, optionally pretreated, is flowed to an FCC zone where the hydrocarbonaceous components are cracked to olefins. Catalytic cracking is accomplished by contacting the lipid composition in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons, such as those of the lipid composition described herein, in a fluidized stream of catalyst, transporting catalyst between reaction and regeneration zones, and combusting coke in the regenerator are well known by those skilled in the art of FCC processes. Exemplary FCC applications and catalysts useful for cracking the lipid composition to produce $C_2$-$C_5$ olefins are described in U.S. Pat. Nos. 6,538,169 and 7,288,685, which are incorporated in their entirety herein by reference.

Suitable FCC catalysts generally comprise at least two components that may or may not be on the same matrix. In some embodiments, both components may be circulated throughout the entire reaction vessel. The first component generally includes any of the well-known catalysts that are used in the art of fluidized catalytic cracking, such as an active amorphous clay-type catalyst and/or a high activity, crystalline molecular sieve. Molecular sieve catalysts may sometimes be preferred over amorphous catalysts because of their much-improved selectivity to desired products. In some preferred embodiments, zeolites may be used as the molecular sieve in the FCC processes. Preferably, the first catalyst component comprises a large pore zeolite, such as an Y-type zeolite, an active alumina material, a binder material, comprising either silica or alumina and an inert filler such as kaolin.

In one embodiment, cracking the lipid composition of the present invention, takes place in the riser section or, alternatively, the lift section, of the FCC zone. The lipid composition is introduced into the riser by a nozzle resulting in the rapid vaporization of the lipid composition. Before contacting the catalyst, the lipid composition will ordinarily have a temperature of about 149° C. to about 316° C. (300° F. to 600° F.). The catalyst is flowed from a blending vessel to the riser where it contacts the lipid composition for a time of abort 2 seconds or less.

The blended catalyst and reacted lipid composition vapors are then discharged from the top of the riser through an outlet and separated into a cracked product vapor stream including olefins and a collection of catalyst particles covered with substantial quantities of coke and generally referred to as "coked catalyst." In an effort to minimize the contact time of the lipid composition and the catalyst which may promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of lipid composition and preferably about 15 wt-% of lipid composition. Other diluents such as dry gas can be used to reach equivalent hydrocarbon partial pressures.

The temperature of the cracked stream at the riser outlet will be about 510° C. to 621° C. (950° F. to 1150° F.). However, riser outlet temperatures above 566° C. (1050° F.) make more dry gas and more olefins. Whereas, riser outlet temperatures below 566° C. (1050° F.) make less ethylene and propylene. Accordingly, it is preferred to run the FCC process at a preferred temperature of about 566° C. to about 630° C., preferred pressure of about 138 kPa to about 240 kPa (20 to 35 psia). Another condition for the process is the catalyst to lipid composition ratio which can vary from about 5 to about 20 and preferably from about 10 to about 15.

In one embodiment of the method for producing a jet fuel, the lipid composition is introduced into the lift section of an FCC reactor. The temperature in the lift section will be very hot and range from about 700° C. (1292° F.) to about 760° C. (1400° F.) with a catalyst to lipid composition ratio of about 100 to about 150. It is anticipated that introducing the lipid composition into the lift section will produce considerable amounts of propylene and ethylene.

In another embodiment of the method for producing a jet fuel using the lipid composition or the lipids produced as described herein, the structure of the lipid composition or the lipids is broken by a process referred to as hydrodeoxygenation (HDO). HDO means removal of oxygen by means of hydrogen, that is, oxygen is removed while breaking the structure of the material. Olefinic double bonds are hydrogenated and any sulphur and nitrogen compounds are removed.

Sulphur removal is called hydrodesulphurization (HDS). Pretreatment and purity of the raw materials (lipid composition or the lipids) contribute to the service life of the catalyst.

Generally in the HDO/HDS step, hydrogen is mixed with the feed stock (lipid composition or the lipids) and then the mixture is passed through a catalyst bed as a co-current flow, either as a single phase or a two phase feed stock. After the HDO/MDS step, the product fraction is separated and passed to a separate isomerzation reactor. An isomerization reactor for biological starting material is described in the literature (FI 100 248) as a co-current reactor.

The process for producing a fuel by hydrogenating a hydrocarbon feed, e.g., the lipid composition or the lipids herein, can also be performed by passing the lipid composition or the lipids as a co-current flow with hydrogen gas through a first hydrogenation zone, and thereafter the hydrocarbon effluent is further hydrogenated in a second hydrogenation zone by passing hydrogen gas to the second hydrogenation zone as a counter-current flow relative to the hydrocarbon effluent. Exemplary HDO applications and catalysts useful for cracking the lipid composition to produce $C_2$-$C_5$ olefins are described in U.S. Pat. No. 7,232,935, which is incorporated in its entirety by reference.

Typically, in the hydrodeoxygenation step, the structure of the biological component, such as the lipid composition or lipids herein, is decomposed, oxygen, nitrogen, phosphorus and sulphur compounds, and light hydrocarbons as gas are removed, and the olefinic bonds are hydrogenated. In the second step of the process, i.e. in the so-called isomerization step, isomerzation is carried out for branching the hydrocarbon chain and improving the performance of the paraffin at low temperatures.

In the first step, i.e. HDO step, of the cracking process, hydrogen gas and the lipid composition or lipids herein which are to be hydrogenated are passed to a HDO catalyst bed system either as co-current or counter-current flows, said catalyst bed system comprising one or more catalyst bed(s), preferably 1-3 catalyst beds. The HDO step is typically operated in a co-current manner. In case of a HDO catalyst bed system comprising two or more catalyst beds, one or more of the beds may be operated using the counter-current flow principle. In the HDO step, the pressure varies between 20 and 150 bar, preferably between 50 and 100 bar, and the temperature varies between 200 and 500° C., preferably in the range of 300-400° C. In the HDO step, known hydrogenation catalysts containing metals from Group VII and/or VIB of the Periodic System may be used. Preferably, the hydrogenation catalysts are supported Pd, Pt, Ni, NiMo or a CoMo catalysts, the support being alumina and/or silica. Typically, NiMo/$Al_2O_3$ and CoMo/$Al_2O_3$ catalysts are used.

Prior to the HDO step, the lipid composition or lipids herein may optionally be treated by prehydrogenation under milder conditions thus avoiding side reactions of the double bonds. Such prehydrogenation is carried out in the presence of a prehydrogenation catalyst at temperatures of 50 400° C. and at hydrogen pressures of 1 200 bar, preferably at a temperature between 150 and 250° C. and at a hydrogen pressure between 10 and 100 bar. The catalyst may contain metals from Group VIII and/or VIB of the Periodic System. Preferably, the prehydrogenation catalyst is a supported Pd, Pt, Ni, NiMo or a CoMo catalyst, the support being alumina and/or silica.

A gaseous stream from the HDO step containing hydrogen is cooled and then carbon monoxide, carbon dioxide, nitrogen, phosphorus and sulphur compounds, gaseous light hydrocarbons and other impurities are removed therefrom. After compressing, the purified hydrogen or recycled hydrogen is returned back to the first catalyst bed and/or between the catalyst beds to make up for the withdrawn gas stream. Water is removed from the condensed liquid. The liquid is passed to the first catalyst bed or between the catalyst beds.

After the HDO step, the product is subjected to an isomerization step. It is substantial for the process that the impurities are removed as completely as possible before the hydrocarbons are contacted with the isomerization catalyst. The isomerization step comprises an optional stripping step, wherein the reaction product from the HDO step may be purified by stripping with water vapour or a suitable gas such as light hydrocarbon, nitrogen or hydrogen. The optional stripping step is carried out in counter-current manner in a unit upstream of the isomerization catalyst, wherein the gas and liquid are contacted with each other, or before the actual isomerization reactor in a separate stripping unit utilizing counter-current principle.

After the stripping step the hydrogen gas and the hydrogenated lipid composition or lipids herein, and optionally an n-paraffin mixture, are passed to a reactive isomerization unit comprising one or several catalyst bed(s). The catalyst beds of the isomerization step may operate either in co-current or counter-current manner.

It is important for the process that the counter-current flow principle is applied in the isomerization step. In the isomerization step this is done by carrying out either the optional stripping step or the isomerization reaction step or both in counter-current manner. In the isomerization step, the pressure varies in the range of 20 150 bar, preferably in the range of 20 100 bar, the temperature being between 200 and 500° C., preferably between 300 and 400° C. In the isomerization step, isomerization catalysts known in the art may be used. Suitable isomerization catalysts contain molecular sieve and/or a metal from Group VII and/or a carrier. Preferably, the isomerization catalyst contains SAPO-11 or SAPO41 or ZSM-22 or ZSM-23 or ferrierite and Pt, Pd or Ni and $Al_2O_3$ or $SiO_2$. Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$. The isomerization step and the HDO step may be carried out in the same pressure vessel or in separate pressure vessels. Optional prehydrogenation may be carried out in a separate pressure vessel or in the same pressure vessel as the HDO and isomerization steps.

Thus, in one embodiment, the product of the one or more chemical reactions is an alkane mixture that comprises ASTM D1655 jet fuel. In some embodiments, the composition conforming to the specification of ASTM 1655 jet fuel has a sulfur content that is less than 10 ppm. In other embodiments, the composition conforming to the specification of ASTM 1655 jet fuel has a T10 value of the distillation curve of less than 205° C. In another embodiment, the composition conforming to the specification of ASTM 1655 jet fuel has a final boiling point (FBP) of less than 300° C. In another embodiment, the composition conforming to the specification of ASTM 1655 jet fuel has a flash point of at least 38° C. In another embodiment, the composition conforming to the specification of ASTM 1655 jet fuel has a density between 775 K/$M^3$ and 840 K/$M^3$. In yet another embodiment, the composition conforming to the specification of ASTM 1655 jet fuel has a freezing point that is below −47° C. In another embodiment, the composition conforming to the specification of ASTM 1655 jet fuel has a net Heat of Combustion that is at least 42.8 MJ/K. In another embodiment, the composition conforming to the specification of ASTM 1655 jet fuel has a hydrogen content that is at least 13.4 mass %. In another embodiment, the composition conforming to the specification of ASTM 1655 jet fuel has a thermal stability, as tested by quantitative gravimetric JFTOT at 260° C., that is below 3 mm of Hg. In another embodiment, the composition conforming to the specification of ASTM 1655 jet fuel has an existent gum that is below 7 mg/dl.

Thus, the present invention discloses a variety of methods in which chemical modification of microalgal lipid is undertaken to yield products useful in a variety of industrial and other applications. Examples of processes for modifying oil produced by the methods disclosed herein include, but are not limited to, hydrolysis of the oil, hydroprocessing of the oil, and esterification of the oil. The modification of the microalgal oil produces basic oleochemicals that can be further modified into selected derivative oleochemicals for a desired function. In a manner similar to that described above with reference to fuel producing processes, these chemical modifications can also be performed on oils generated from the microbial cultures described herein. Examples of basic oleochemicals include, but are not limited to, soaps, fatty acids, fatty acid methyl esters, and glycerol. Examples of derivative oleochemicals include, but are not limited to, fatty nitriles, esters, dimer acids, quats, surfactants, fatty alkanolamides, fatty alcohol sulfates, resins, emulsifiers, fatty alcohols, olefins, and higher alkanes.

Hydrolysis of the fatty acid constituents from the glycerolipids produced by the methods of the invention yields free fatty acids that can be derivatized to produce other useful chemicals. Hydrolysis occurs in the presence of water and a catalyst which may be either an acid or a base. The liberated free fatty acids can be derivatized to yield a variety of products, as reported in the following: U.S. Pat. No. 5,304,664 (Highly sulfated fatty acids); U.S. Pat. No. 7,262,158 (Cleansing compositions); U.S. Pat. No. 7,115,173 (Fabric softener compositions); U.S. Pat. No. 6,342,208 (Emulsions for treating skin); U.S. Pat. No. 7,264,886 (Water repellant compositions); U.S. Pat. No. 6,924,333 (Paint additives); U.S. Pat. No. 6,596,768 (Lipid-enriched ruminant feedstock); and U.S. Pat. No. 6,380,410 (Surfactants for detergents and cleaners).

With regard to hydrolysis, in one embodiment of the invention, a triglyceride oil is optionally first hydrolyzed in a liquid medium such as water or sodium hydroxide so as to obtain glycerol and soaps. There are various suitable triglyceride hydrolysis methods, including, but not limited to, saponification, acid hydrolysis, alkaline hydrolysis, enzymatic hydrolysis (referred herein as splitting), and hydrolysis using hot-compressed water. One skilled in the art will recognize that a triglyceride oil need not be hydrolyzed to produce an oleochemical; rather, the oil may be converted directly to the desired oleochemical by other known processes. For example, the triglyceride oil may be directly converted to a methyl ester fatty acid through esterification.

In some embodiments, catalytic hydrolysis of the oil produced by methods disclosed herein occurs by splitting the oil into glycerol and fatty acids. As discussed above, the fatty acids may then be further processed through several other modifications to obtained derivative oleochemicals. For example, in one embodiment the fatty acids may undergo an amination reaction to produce fatty nitrogen compounds. In another embodiment, the fatty acids may undergo ozonolysis to produce mono- and dibasic-acids.

In other embodiments hydrolysis may occur via the, splitting of oils produced herein to create oleochemicals. In some preferred embodiments of the invention, a triglyceride oil may be split before other processes is performed. One skilled in the art will recognize that there are many suitable triglyceride splitting methods, including, but not limited to, enzymatic splitting and pressure splitting.

Generally, enzymatic oil splitting methods use enzymes, lipases, as biocatalysts acting on a water/oil mixture. Enzymatic splitting then splits the oil or fat, respectively, is into glycerol and free fatty acids. The glycerol may then migrate into the water phase whereby the organic phase is enriched with free fatty acids.

The enzymatic splitting reactions generally take place at the phase boundary between organic and aqueous phase, where the enzyme is present only at the phase boundary. Triglycerides that meet the phase boundary then contribute to or participate in the splitting reaction. As the reaction proceeds, the occupation density or concentration of fatty acids still chemically bonded as glycerides, in comparison to free fatty acids, decreases at the phase boundary so that the reaction is slowed down. In certain embodiments, enzymatic splitting may occur at room temperature. One of ordinary skill in the art knows the suitable conditions for splitting oil into the desired fatty acids.

By way of example, the reaction speed can be accelerated by increasing the interface boundary surface. Once the reaction is complete, free fatty acids are then separated from the organic phase freed from enzyme, and the residue which still contains fatty acids chemically bonded as glycerides is fed back or recycled and mixed with fresh oil or fat to be subjected to splitting. In this manner, recycled glycerides are then subjected to a further enzymatic splitting process. In some embodiments, the free fatty acids are extracted from an oil or fat partially split in such a manner. In that way, if the chemically bound fatty acids (triglycerides) are returned or fed back into the splitting process, the enzyme consumption can be drastically reduced.

The splitting degree is determined as the ratio of the measured acid value divided by the theoretically possible acid value which can be computed for a given oil or fat. Preferably, the acid value is measured by means of titration according to standard common methods. Alternatively, the density of the aqueous glycerol phase can be taken as a measure for the splitting degree.

In one embodiment, the slitting process as described herein is also suitable for splitting the mono-, di- and triglyceride that are contained in the so-called soap-stock from the alkali refining processes of the produced oils. In this manner, the soap-stock can be quantitatively converted without prior saponification of the neutral oils into the fatty acids. For this purpose, the fatty acids being chemically bonded in the soaps are released, preferably before splitting, through an addition of acid. In certain embodiments, a buffer solution is used in addition to water and enzyme for the splitting process.

In one embodiment, oils produced in accordance with the methods of the invention can also be subjected to saponification as a method of hydrolysis. Animal and plant oils are typically made of triacylglycerols (TAGs), which are esters of fatty acids with the trihydric alcohol, glycerol. In an alkaline hydrolysis reaction, the glycerol in a TAG is removed, leaving three carboxylic acid anions that can associate with alkali metal cations such as sodium or potassium to produce fatty acid salts. In this scheme, the carboxylic acid constituents are cleaved from the glycerol moiety and replaced with hydroxyl groups. The quantity of base (e.g., KOH) that is used in the reaction is determined by the desired degree of saponification. If the objective is, for example, to produce a soap product that comprises some of the oils originally present in the TAG composition, an amount of base insufficient to convert all of the TAGs to fatty acid salts is introduced into the reaction mixture. Normally, this reaction is performed in an aqueous solution and proceeds slowly, but may be expedited by the addition of heat. Precipitation of the fatty acid salts can be facilitated by addition of salts, such as water-soluble alkali metal halides (e.g., NaCl or KCl), to the reaction mixture. Preferably, the base is an alkali metal hydroxide, such as NaOH or KOH. Alternatively, other bases, such as alkanolamines, including for example triethanolamine and aminomethylpropanol, can be used in the reaction scheme. In some cases, these alternatives may be preferred to produce a clear soap product.

In some methods, the first step of chemical modification may be hydroprocessing to saturate double bonds, followed by deoxygenation at elevated temperature in the presence of hydrogen and a catalyst. In other methods, hydrogenation and deoxygenation may occur in the same reaction. In still other methods deoxygenation occurs before hydrogenation. Isomerization may then be optionally performed, also in the presence of hydrogen and a catalyst. Finally, gases and naphtha components can be removed if desired. For example, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

In some embodiments of the invention, the triglyceride oils are partially or completely deoxygenated. The deoxygenation reactions form desired products, including, but not limited to, fatty acids, fatty alcohols, polyols, ketones, and aldehydes. In general, without being limited by any particular theory, the deoxygenation reactions involve a combination of various different reaction pathways, including without limitation: hydrogenolysis, hydrogenation, consecutive hydrogenation-hydrogenolysis, consecutive hydrogenolysis-hydrogenation, and combined hydrogenation-hydrogenolysis reactions, resulting in at least the partial removal of oxygen from the fatty acid or fatty acid ester to produce reaction products, such as fatty alcohols, that can be easily converted to the desired chemicals by further processing. For example, in one embodiment, a fatty alcohol may be converted to olefins through FCC reaction or to higher alkanes through a condensation reaction.

One such chemical modification is hydrogenation, which is the addition of hydrogen to double bonds in the fatty acid constituents of glycerolipids or of free fatty acids. The hydrogenation process permits the transformation of liquid oils into semi-solid or solid fats, which may be more suitable for specific applications.

Hydrogenation of oil produced by the methods described herein can be performed in conjunction with one or more of the methods and/or materials provided herein, as reported in the following: U.S. Pat. No. 7,288,278 (Food additives or medicaments); U.S. Pat. No. 5,346,724 (Lubrication products); U.S. Pat. No. 5,475,160 (Fatty alcohols); U.S. Pat. No. 5,091,116 (Edible oils); U.S. Pat. No. 6,808,737 (Structural fats for margarine and spreads); U.S. Pat. No. 5,298,637 (Reduced-calorie fat substitutes); U.S. Pat. No. 6,391,815 (Hydrogenation catalyst and sulfur adsorbent); U.S. Pat. Nos. 5,233,099 and 5,233,100 (Fatty alcohols); U.S. Pat. No. 4,584,139 (Hydrogenation catalysts); U.S. Pat. No. 6,057,375 (Foam suppressing agents); and U.S. Pat. No. 7,118,773 (Edible emulsion spreads).

One skilled in the art will recognize that various processes may be used to hydrogenate oil. One suitable method includes contacting the oil with hydrogen or hydrogen mixed with a suitable gas and a catalyst under conditions sufficient in a hydrogenation reactor to form a hydrogenated product. The hydrogenation catalyst generally can include Cu, Re, Ni, Fe, Co, Ru, Pd, Rh, Pt, Os, Ir, and alloys or any combination thereof, either alone or with promoters such as W, Mo, Au, Ag, Cr, Zn, Mn, Sn, B, P, Bi, and alloys or any combination thereof. Other effective hydrogenation catalyst materials include either supported nickel or ruthenium modified with rhenium. In an embodiment, the hydrogenation catalyst also includes any one of the supports, depending on the desired functionality of the catalyst. The hydrogenation catalysts may be prepared by methods known to those of ordinary skill in the art.

In some embodiments the hydrogenation catalyst includes a supported Group VIII metal catalyst and a metal sponge material (e.g., a sponge nickel catalyst). Raney nickel provides an example of an activated sponge nickel catalyst suitable for use in this invention. In other embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (i.e., molybdenum or chromium) in the amount such that about 1 to 2 weight % remains in the formed sponge nickel catalyst. In another embodiment, the hydrogenation catalyst is prepared using a solution of ruthenium(III) nitrosylnitrate, ruthenium (III) chloride in water to impregnate a suitable support material. The solution is then dried to form a solid having a water content of less than about 1% by weight. The solid may then be reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the catalyst described includes a catalyst support. The catalyst support stabilizes and supports the catalyst. The type of catalyst support used depends on the chosen catalyst and the reaction conditions. Suitable supports for the invention include, but are not limited to, carbon, silica, silica-alumina, zirconia, titania, ceria, vanadia, nitride, boron nitride, heteropolyacids, hydroxyapatite, zinc oxide, chromia, zeolites, carbon nanotubes, carbon fullerene and any combination thereof.

The catalysts used in this invention can be prepared using conventional methods known to those in the art. Suitable methods may include, but are not limited to, incipient wetting, evaporative impregnation, chemical vapor deposition, wash-coating, magnetron sputtering techniques, and the like.

The conditions for which to carry out the hydrogenation reaction will vary based on the type of starting material and the desired products. One of ordinary skill in the art, with the benefit of this disclosure, will recognize the appropriate reaction conditions. In general, the hydrogenation reaction is conducted at temperatures of 80° C. to 250° C., and preferably at 90° C. to 200° C., and most preferably at 100° C. to 150° C. In some embodiments, the hydrogenation reaction is conducted at pressures from 500 KPa to 14000 KPa.

The hydrogen used in the hydrogenolysis reaction of the current invention may include external hydrogen, recycled hydrogen, in situ generated hydrogen, and any combination thereof. As used herein, the term "external hydrogen" refers to hydrogen that does not originate from the biomass reaction itself, but rather is added to the system from another source.

In some embodiments of the invention, it is desirable to convert the starting triglyceride or fatty acid to a smaller molecule that will be more readily converted to desired higher hydrocarbons. One suitable method for this conversion is through a hydrogenolysis reaction. Various processes are known for performing hydrogenolysis of oil. One suitable method includes contacting oil with hydrogen or hydrogen mixed with a suitable gas and a hydrogenolysis catalyst in a hydrogenolysis reactor under conditions sufficient to form a reaction product comprising smaller molecules or polyols. As used herein, the term "smaller molecules or polyols" includes any molecule that has a smaller molecular weight, which can include a smaller number of carbon atoms or oxygen atoms than the starting oil. In an embodiment, the reaction products include smaller molecules that include polyols and alcohols. One of ordinary skill in the art can readily select the appropriate method by which to carry out the hydrogenolysis reaction.

In some embodiments, a 5 and/or 6 carbon sugar or sugar alcohol may be converted to propylene glycol, ethylene glycol, and glycerol using a hydrogenolysis catalyst. The hydrogenolysis catalyst may include Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. The hydrogenolysis catalyst may also include a carbonaceous pyropolymer catalyst containing transition metals (e.g., chromium, molybdemum, tungsten, rhenium, manganese, copper, cadmium) or Group VIII metals (e.g., iron, cobalt, nickel, platinum, palladium, rhodium, ruthenium, iridium, and osmium). In certain embodiments, the hydrogenolysis catalyst may include any of the above metals combined with an alkaline earth metal oxide or adhered to a catalytically active support. In certain embodiments, the catalyst described in the hydrogenolysis reaction may include a catalyst support as described above for the hydrogenation reaction.

The conditions for which to carry out the hydrogenolysis reaction will vary based on the type of starting material and the desired products. One of ordinary skill in the art, with the benefit of this disclosure, will recognize the appropriate conditions to use to carry out the reaction. In general, they hydrogenolysis reaction is conducted at temperatures of 110° C. to 300° C., and preferably at 170° C. to 220° C., and most preferably at 200° C. to 225° C. In some embodiments, the hydrogenolysis reaction is conducted under basic conditions, preferably at a pH of 8 to 13, and even more preferably at a pH of 10 to 12. In some embodiments, the hydrogenolysis reaction is conducted at pressures in a range between 60 KPa and 16500 KPa, and preferably in a range between 1700 KPa and 14000 KPa, and even more preferably between 4800 KPa and 11000 KPa.

The hydrogen used in the hydrogenolysis reaction of the current invention can include external hydrogen, recycled hydrogen, in situ generated hydrogen, and any combination thereof.

In some embodiments, the reaction products discussed above may be converted into higher hydrocarbons through a condensation reaction in a condensation reactor. In such embodiments, condensation of the reaction products occurs in the presence of a catalyst capable of forming higher hydrocarbons. While not intending to be limited by theory, it is believed that the production of higher hydrocarbons proceeds through a stepwise addition reaction including the formation of carbon-carbon, or carbon-oxygen bond. The resulting reaction products include any number of compounds containing these moieties, as described in more detail below.

In certain embodiments, suitable condensation catalysts include an acid catalyst, a base catalyst, or an acid/base catalyst. As used herein, the term "acid/base catalyst" refers to a catalyst that has both an acid and a base functionality. In some embodiments the condensation catalyst can include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the condensation catalyst can also include a modifier. Suitable modifiers include La, Y, Sc, P, B, Bi, Li, Na, K, Rb, Cs, Mg, Ca, Sr, Ba, and any combination thereof. In some embodiments, the condensation catalyst can also include a metal. Suitable metals include Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof.

In certain embodiments, the catalyst described in the condensation reaction may include a catalyst support as described above for the hydrogenation reaction. In certain embodiments, the condensation catalyst is self-supporting. As used herein, the term "self-supporting" means that the catalyst does not need another material to serve as support. In other embodiments, the condensation catalyst in used in conjunction with a separate support suitable for suspending the catalyst. In an embodiment, the condensation catalyst support is silica.

The conditions under which the condensation reaction occurs will vary based on the type of starting material and the desired products. One of ordinary skill in the art, with the benefit of this disclosure, will recognize the appropriate conditions to use to carry out the reaction. In some embodiments, the condensation reaction is carried out at a temperature at which the thermodynamics for the proposed reaction are favorable. The temperature for the condensation reaction will vary depending on the specific starting polyol or alcohol. In some embodiments, the temperature for the condensation reaction is in a range from 80° C. to 500° C., and preferably from 125° C. to 450° C., and most preferably from 125° C. to 250° C. In some embodiments, the condensation reaction is conducted at pressures in a range between 0 KPa to 9000 KPa, and preferably in a range between 0 KPa and 7000 KPa, and even more preferably between 0 KPa and 5000 KPa.

The higher alkanes formed by certain methods of the invention include, but are not limited to, branched or straight chain alkanes that have from 4 to 30 carbon atoms, branched or straight chain alkenes that have from 4 to 30 carbon atoms, cycloalkanes that have from 5 to 30 carbon atoms, cycloalkenes that have from 5 to 30 carbon atoms, aryls, fused aryls, alcohols, and ketones. Suitable alkanes include, but are not limited to, butane, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, nonyldecane, nonyldecene, eicosane, eicosene, uneicosane, uneicosene, doeicosane, doeicosene, trieicosane, trieicosene, tetraeicosane, tetraeicosene, and isomers thereof. Some of these products may be suitable for use as fuels.

In some embodiments, the cycloalkanes and the cycloalkenes are unsubstituted. In other embodiments, the cycloalkanes and cycloalkenes are mono-substituted. In still other embodiments, the cycloalkanes and cycloalkenes are multi-substituted. In the embodiments comprising the substituted cycloalkanes and cycloalkenes, the substituted group includes, without limitation, a branched or straight chain alkyl having 1 to 12 carbon atoms, a branched or straight chain alkylene having 1 to 12 carbon atoms, a phenyl, and any combination thereof. Suitable cycloalkanes and cycloalkenes include, but are not limited to, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, isomers and any combination thereof.

In some embodiments, the aryls formed are unsubstituted. In another embodiment, the aryls formed are mono-substituted. In the embodiments comprising the substituted aryls, the substituted group includes, without limitation, a branched or straight chain alkyl having 1 to 12 carbon atoms, a branched or straight chain alkylene having 1 to 12 carbon atoms, a phenyl, and any combination thereof. Suitable aryls for the invention include, but are not limited to, benzene, toluene, xylene, ethyl benzene, para xylene, meta xylene, and any combination thereof.

The alcohols produced in certain methods of the invention have from 4 to 30 carbon atoms. In some embodiments, the alcohols are cyclic. In other embodiments, the alcohols are branched. In another embodiment, the alcohols are straight chained. Suitable alcohols for the invention include, but are not limited to, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The ketones produced in certain methods of the invention have from 4 to 30 carbon atoms. In an embodiment, the ketones are cyclic. In another embodiment, the ketones are branched. In another embodiment, the ketones are straight chained. Suitable ketones for the invention include, but are not limited to, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

Another chemical modification that may be performed on microalgal oil produced by the methods of the invention is interesterification. Naturally produced glycerolipids do not have a uniform distribution of fatty acid constituents. In the context of oils, interesterification refers to the exchange of acyl radicals between two esters of different glycerolipids. The interesterification process provides a mechanism by which the fatty acid constituents of a mixture of glycerolipids can be rearranged to modify the distribution pattern. Interesterification is a well-known chemical process, and generally comprises heating (to about 200° C.) a mixture of oils for a period (e.g, 30 minutes) in the presence of a catalyst, such as an alkali metal or alkali metal alkylate (e.g., sodium methoxide). This process can be used to randomize the distribution pattern of the fatty acid constituents of an oil mixture, or can be directed to produce a desired distribution pattern. This method of chemical modification of lipids can be performed on materials provided herein, such as microbial biomass with a percentage of dry cell weight as lipid at least 20%.

Directed interesterification, in which a specific distribution pattern of fatty acids is sought, can be performed by maintaining the oil mixture at a temperature below the melting point of some TAGs which might occur. This results in selective crystallization of these TAGs, which effectively removes them from the reaction mixture as they crystallize. The process can be continued until most of the fatty acids in the oil have precipitated, for example. A directed interesterification process can be used, for example, to produce a product with a lower calorie content via the substitution of longer-chain fatty acids with shorter-chain counterparts. Directed interesterification can also be used to produce a product with a mixture of fats that can provide desired melting characteristics and structural features sought in food additives or products (e.g., margarine) without resorting to hydrogenation, which can produce unwanted trans isomers.

Interesterification of oils produced by the methods described herein can be performed in conjunction with one or more of the methods and/or materials, or to produce products, as reported in the following: U.S. Pat. No. 6,080,853 (Non-digestible fat substitutes); U.S. Pat. No. 4,288,378 (Peanut butter stabilizer); U.S. Pat. No. 5,391,383 (Edible spray oil); U.S. Pat. No. 6,022,577 (Edible fats for food products); U.S. Pat. No. 5,434,278 (Edible fats for food products); U.S. Pat. No. 5,268,192 (Low calorie nut products); U.S. Pat. No. 5,258,197 (Reduce calorie edible compositions); U.S. Pat. No. 4,335,156 (Edible fat product); U.S. Pat. No. 7,288,278 (Food additives or medicaments); U.S. Pat. No. 7,115,760 (Fractionation process); U.S. Pat. No. 6,808,737 (Structural fats); U.S. Pat. No. 5,888,947 (Engine lubricants); U.S. Pat. No. 5,686,131 (Edible oil mixtures); and U.S. Pat. No. 4,603,188 (Curable urethane compositions).

In one embodiment in accordance with the invention, transesterification of the oil, as described above, is followed by reaction of the transesterified product with polyol, as reported in U.S. Pat. No. 6,465,642, to produce polyol fatty acid polyesters. Such an esterification and separation process may comprise the steps as follows: reacting a lower alkyl ester with polyol in the presence of soap; removing residual soap from the product mixture; water-washing and drying the product mixture to remove impurities; bleaching the product mixture for refinement; separating at least a portion of the unreacted lower alkyl ester from the polyol fatty acid polyester in the product mixture; and recycling the separated unreacted lower alkyl ester.

Transesterification can also be performed on microbial biomass with short chain fatty acid esters, as reported in U.S. Pat. No. 6,278,006. In general, transesterification may be performed by adding a short chain fatty acid ester to an oil in the presence of a suitable catalyst and heating the mixture. In some embodiments, the oil comprises about 5% to about 90% of the reaction mixture by weight. In some embodiments, the short chain fatty acid esters can be about 10% to about 50% of the reaction mixture by weight. Non-limiting examples of catalysts include base catalysts, sodium methoxide, acid catalysts including inorganic acids such as sulfuric acid and acidified clays, organic acids such as methane sulfonic acid, benzenesulfonic acid, and toluenesulfonic acid, and acidic resins such as Amberlyst 15. Metals such as sodium and magnesium, and metal hydrides also are useful catalysts.

Another such chemical modification is hydroxylation, which involves the addition of water to a double bond resulting in saturation and the incorporation of a hydroxyl moiety. The hydroxylation process provides a mechanism for converting one or more fatty acid constituents of a glycerolipid to a hydroxy fatty acid. Hydroxylation can be performed, for example, via the method reported in U.S. Pat. No. 5,576,027. Hydroxylated fatty acids, including castor oil and its derivatives, are useful as components in several industrial applications, including food additives, surfactants, pigment wetting agents, defoaming agents, water proofing additives, plasticizing agents, cosmetic emulsifying and/or deodorant agents, as well as in electronics, pharmaceuticals, paints, inks, adhesives, and lubricants. One example of how the hydroxylation of a glyceride may be performed is as follows: fat may be heated, preferably to about 30-50° C. combined with heptane and maintained at temperature for thirty minutes or more; acetic acid may then be added to the mixture followed by an aqueous solution of sulfuric acid followed by an aqueous hydrogen peroxide solution which is added in small increments to the mixture over one hour; after the aqueous hydrogen peroxide, the temperature may then be increased to at least about 60° C. and stirred for at least six hours; after the stirring, the mixture is allowed to settle and a lower aqueous layer formed by the reaction may be removed while the upper heptane layer formed by the reaction may be washed with hot water having a temperature of about 60° C.; the washed heptane layer may then be neutralized with an aqueous potassium hydroxide solution to a pH of about 5 to 7 and then removed by distillation under vacuum; the reaction product may then be dried under vacuum at 100° C. and the dried product steam-deodorized under vacuum conditions and filtered at about 50° to 60° C. using diatomaceous earth.

Hydroxylation of microbial oils produced by the methods described herein can be performed in conjunction with one or more of the methods and/or materials, or to produce products, as reported in the following: U.S. Pat. No. 6,590,113 (Oil-based coatings and ink); U.S. Pat. No. 4,049,724 (Hydroxylation process); U.S. Pat. No. 6,113,971 (Olive oil butter); U.S. Pat. No. 4,992,189 (Lubricants and lube additives); U.S. Pat. No. 5,576,027 (Hydroxylated milk); and U.S. Pat. No. 6,869,597 (Cosmetics).

Hydroxylated glycerolipids can be converted to estolides. Estolides consist of a glycerolipid in which a hydroxylated fatty acid constituent has been esterified to another fatty acid molecule. Conversion of hydroxylated glycerolipids to estolides can be carried out by warming a mixture of glycerolipids and fatty acids and contacting the mixture with a mineral acid, as described by Isbell et al., *JAOCS* 71(2):169-174 (1994). Estolides are useful in a variety of applications, including without limitation those reported in the following: U.S. Pat. No. 7,196,124 (Elastomeric materials and floor coverings); U.S. Pat. No. 5,458,795 (Thickened oils for high-temperature applications); U.S. Pat. No. 5,451,332 (Fluids for industrial applications); U.S. Pat. No. 5,427,704 (Fuel additives); and U.S. Pat. No. 5,380,894 (Lubricants, greases, plasticizers, and printing inks).

Other chemical reactions that can be performed on microbial oils include reacting triacylglycerols with a cyclopropanating agent to enhance fluidity and/or oxidative stability, as reported in U.S. Pat. No. 6,051,539; manufacturing of waxes from triacylglycerols, as reported in U.S. Pat. No. 6,770,104; and epoxidation of triacylglycerols, as reported in "The effect of fatty acid composition on the acrylation kinetics of epoxidized triacylglycerols", Journal of the American Oil Chemists' Society, 79:1, 59-63, (2001) and Free Radical Biology and Medicine, 37:1, 104-114 (2004).

The generation of oil-bearing microbial biomass for fuel and chemical products as described above results in the production of delipidated biomass meal. Delipidated meal is a byproduct of preparing algal oil and is useful as animal feed for farm animals, e.g., ruminants, poultry, swine and aquaculture. The resulting meal, although of reduced oil content, still contains high quality proteins, carbohydrates, fiber, ash, residual oil and other nutrients appropriate for an animal feed. Because the cells are predominantly lysed by the oil separation process, the delipidated meal is easily digestible by such animals. Delipidated meal can optionally be combined with other ingredients, such as grain, in an animal feed. Because delipidated meal has a powdery consistency, it can be pressed into pellets using an extruder or expander or another type of machine, which are commercially available.

The invention, having been described in detail above, is exemplified in the following examples, which are offered to illustrate, but not to limit, the claimed invention.

VIII. Examples

Example 1

Methods for Culturing *Prototheca*

*Prototheca* strains were cultivated to achieve a high percentage of oil by dry cell weight. Cryopreserved cells were thawed at room temperature and 500 ul of cells were added to 4.5 ml of medium (4.2 g/L $K_2HPO_4$, 3.1 g/L $NaH_2PO_4$, 0.24 g/L $MgSO_4 \cdot 7H_2O$, 0.25 g/L Citric Acid monohydrate, 0.025 g/L $CaCl_2 \cdot 2H_2O$, 2 g/L yeast extract) plus 2% glucose and grown for 7 days at 28° C. with agitation (200 rpm) in a 6-well plate. Dry cell weights were determined by centrifuging 1 ml of culture at 14,000 rpm for 5 min in a pre-weighed Eppendorf tube. The culture supernatant was discarded and the resulting cell pellet washed with 1 ml of deionized water. The culture was again centrifuged, the supernatant discarded, and the cell pellets placed at −80° C. until frozen. Samples were then lyophilized for 24 hrs and dry cell weights calculated.

For determination of total lipid in cultures, 3 ml of culture was removed and subjected to analysis using an Ankom system (Ankom Inc., Macedon, N.Y.) according to the manufacturer's protocol. Samples were subjected to solvent extraction with an Amkom XT10 extractor according to the manufacturer's protocol. Total lipid was determined as the difference in mass between acid hydrolyzed dried samples and solvent extracted, dried samples. Percent oil dry cell weight measurements are shown in Table 2.

TABLE 2

| Percent oil by dry cell weight | | |
|---|---|---|
| Species | Strain | % Oil |
| *Prototheca stagnora* | UTEX 327 | 13.14 |
| *Prototheca moriformis* | UTEX 1441 | 18.02 |
| *Prototheca moriformis* | UTEX 1435 | 27.17 |

Microalgae samples from the strains listed in Table 22 of U.S. Patent Application Publication 20100151112 were genotyped. Genomic DNA was isolated from algal biomass as follows. Cells (approximately 200 mg) were centrifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and tubes were placed at −80° C. for at least 15 minutes. Samples were removed and 150 µl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 ul of 5M NaCl. Samples were vortexed briefly, followed by the addition of 66 µl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 µl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 µl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 µl of 10 mM TrisCl, 1 mM EDTA (pH 8.0).

Five µl of total algal DNA, prepared as described above, was diluted 1:50 in 10 mM Tris, pH 8.0. PCR reactions, final volume 20 µl, were set up as follows. Ten µl of 2× iProof HF master mix (BIO-RAD) was added to 0.4 µl primer SZ02613 (5'-TGTTGAAGAATGAGCCGGCGAC-3' (SEQ ID NO:13) at 10 mM stock concentration). This primer sequence runs from position 567-588 in Gen Bank accession no. L43357 and is highly conserved in higher plants and algal plastid genomes. This was followed by the addition of 0.4 µl primer SZ02615 (5'-CAGTGAGCTATTACGCACTC-3'

(SEQ ID NO:14) at 10 mM stock concentration). This primer sequence is complementary to position 1112-1093 in Gen Bank accession no. L43357 and is highly conserved in higher plants and algal plastid genomes. Next, 5 µl of diluted total DNA and 3.2 µl dH$_2$O were added. PCR reactions were run as follows: 98° C., 45"; 98° C., 8"; 53° C., 12"; 72° C., 20" for 35 cycles followed by 72° C. for 1 min and holding at 25° C. For purification of PCR products, 20 µl of 10 mM Tris, pH 8.0, was added to each reaction, followed by extraction with 40 µl of Phenol:Chloroform:isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates.

Purified plasmid DNA was sequenced in both directions using M13 forward and reverse primers. In total, twelve *Prototheca* strains were selected to have their 23S rRNA DNA sequenced and the sequences are listed in the Sequence Listing. A summary of the strains and Sequence Listing Numbers is included below. The sequences were analyzed for overall divergence from the UTEX 1435 (SEQ ID NO: 5) sequence. Two pairs emerged (UTEX 329/UTEX 1533 and UTEX 329/UTEX 1440) as the most divergent. In both cases, pairwise alignment resulted in 75.0% pairwise sequence identity. The percent sequence identity to UTEX 1435 is also included below.

| Species | Strain | % nt identity | SEQ ID NO. |
|---|---|---|---|
| Prototheca kruegani | UTEX 329 | 75.2 | SEQ ID NO: 1 |
| Prototheca wickerhamii | UTEX 1440 | 99 | SEQ ID NO: 2 |
| Prototheca stagnora | UTEX 1442 | 75.7 | SEQ ID NO: 3 |
| Prototheca moriformis | UTEX 288 | 75.4 | SEQ ID NO: 4 |
| Prototheca moriformis | UTEX 1439; 1441; 1435; 1437 | 100 | SEQ ID NO: 5 |
| Prototheca wikerhamii | UTEX 1533 | 99.8 | SEQ ID NO: 6 |
| Prototheca moriformis | UTEX 1434 | 75.9 | SEQ ID NO: 7 |
| Prototheca zopfii | UTEX 1438 | 75.7 | SEQ ID NO: 8 |
| Prototheca moriformis | UTEX 1436 | 88.9 | SEQ ID NO: 9 |

Lipid samples from a subset of the above-listed strains were analyzed for lipid profile using HPLC. Results are shown below in Table 3.

TABLE 3

| Diversity of lipid chains in microalgal species | | | | | | | | | |
|---|---|---|---|---|---|---|---|---|---|
| Strain | C14:0 | C16:0 | C16:1 | C18:0 | C18:1 | C18:2 | C18:3 | C20:0 | C20:1 |
| UTEX 327 | 0 | 12.01 | 0 | 0 | 50.33 | 17.14 | 0 | 0 | 0 |
| UTEX 1441 | 1.41 | 29.44 | 0.70 | 3.05 | 57.72 | 12.37 | 0.97 | 0.33 | 0 |
| UTEX 1435 | 1.09 | 25.77 | 0 | 2.75 | 54.01 | 11.90 | 2.44 | 0 | 0 |

Example 2

Methods for Transforming *Prototheca*

A. General Method for Biolistic Transformation of *Prototheca*

S550d gold carriers from Seashell Technology were prepared according to the protocol from manufacturer. Linearized plasmid (20 µg) was mixed with 50 µl of binding buffer and 60 µl (30 mg) of S550d gold carriers and incubated in ice for 1 min Precipitation buffer (100 µl) was added, and the mixture was incubated in ice for another 1 min. After vortexing, DNA-coated particles were pelleted by spinning at 10,000 rpm in an Eppendorf 5415C microfuge for 10 seconds. The gold pellet was washed once with 500 µl of cold 100% ethanol, pelleted by brief spinning in the microfuge, and resuspended with 50 µl of ice-cold ethanol. After a brief (1-2 sec) sonication, 10 µl of DNA-coated particles were immediately transferred to the carrier membrane.

*Prototheca* strains were grown in proteose medium (2 g/L yeast extract, 2.94 mM NaNO$_3$, 0.17 mM CaCl$_2$.2H$_2$O, 0.3 mM MgSO$_4$.7H$_2$O, 0.4 mM K$_2$HPO$_4$, 1.28 mM KH$_2$PO$_4$, 0.43 mM NaCl) on a gyratory shaker until it reaches a cell density of 2×10$^6$ cells/ml. The cells were harvested, washed once with sterile distilled water, and resuspended in 50 µl of medium. 1×10$^7$ cells were spread in the center third of a non-selective proteose media plate. The cells were bombarded with the PDS-1000/He Biolistic Particle Delivery system (Bio-Rad). Rupture disks (1100 and 1350 psi) were used, and the plates are placed 9 and 12 cm below the screen/macrocarrier assembly. The cells were allowed to recover at 25° C. for 12-24 h. Upon recovery, the cells were scraped from the plates with a rubber spatula, mixed with 100 µl of medium and spread on plates containing the appropriate antibiotic selection. After 7-10 days of incubation at 25° C., colonies representing transformed cells were visible on the plates from 1100 and 1350 psi rupture discs and from 9 and 12 cm distances. Colonies were picked and spotted on selective agar plates for a second round of selection.

Example 3

Generation of a Microalgal Strain Capable of Metabolizing Xylose

Methods and effects of expressing a heterologous exogenous gene in *Prototheca* species, including, for example, codon optimization and chromosomal recombination sites, have been previously described in PCT Application No. PCT/US2009/66142, hereby incorporated by reference, for these teachings. This example demonstrates the generation of a transgenic strain derived from *Prototheca moriformis* (UTEX 1435) containing exogenous genes for the metabolism and transport of xylose. The resulting transgenic *Prototheca* strain generated had the ability to grow on media containing xylose as the sole carbon source. As discussed above, the ability to metabolize xylose is important because xylose, a pentose, is a significant component of cellulosic-derived feedstocks. Xylose is the major sugar monomer component of hemicellulose, which, along with cellulose, forms the major structural components of most plant matter.

Preliminary results showed that *Prototheca moriformis* (UTEX 1435) can convert small amounts of xylose to xylitol, as indicated by analytical measurements of the sugar levels in liquid media over time. *Prototheca moriformis* (UTEX 1435)

was cultured in the media and conditions as described in Example 1 above in 4% xylose with 0.25% glucose as carbon sources in the medium. Also included were a no-cells-added negative control and a 4% glucose condition as a positive control for growth and a negative control for xylitol production. Table 4 shows that no xylitol was produced in the negative control condition, whereas xylose containing medium with *Prototheca* cells produced detectable amounts of xylitol in the culture supernatant after 5 days in culture. There was robust growth for cells in the glucose only condition, but no detectable level of xylitol was produced.

TABLE 4

| Strain | Media | OD750 | Day 5 xylose (g/L) | xylitol (g/L) |
|---|---|---|---|---|
| no cells control | 4% xylose + 0.25% glucose | 0.0 | 41.0 | none detected |
| UTEX 1435 | 4% xylose + 0.25% glucose | 2.4 | 37.7 | detected at <2.5 g/L |
| UTEX 1435 | 4% glucose control | 15.4 | none detected | none detected |

This result may indicate that xylose can be converted into xylitol via an endogenous aldo-keto reductase enzymatic activity in *Prototheca moriformis*. Enzymes belonging to this family of NAPDH-dependent oxidoreductases reside within the confines of the plasma membrane, and if such an enzyme is responsible for the conversion of xylose to xylitol, then the xylose in the culture medium must be entering into the cell via an endogenous sugar transporter.

In organisms that can metabolize xylose, xylose is converted into xylulose-5-phosphate, which is further metabolized via the pentose phosphate pathway. *Prototheca moriformis* may be capable of taking up xylose from its surrounding, but is deficient in its ability to efficiently convert xylose into xylulose-5-phosphate. The results shown in Table 4 above suggest that this may be the case. To test this hypothesis, the present invention provides methods and reagents for expressing xylose isomerase to first convert xylose into xylulose and xylulokinase to convert the xylulose to xylulose-5-phosphate. An exemplary illustration of such transgenic microalgal cells is described below using *Prototheca moriformis* (UTEX 1435).

A transgenic recipient strain of *Prototheca moriformis* expressing the xylose isomerase (XylA) gene from *Piromyces* sp. and the xylulokinase (XYL3) gene from *Pichia stipitis* and the invertase gene from *S. cerevisiae* (suc2, a selectable marker) was generated using the methodology and transformations previously described in PCT Patent Publication Nos. WO 2010/063031 and WO 2010/063032, each of which is incorporated herein by reference for their teachings of these methods. Positive clones were selected on sucrose containing medium and plates. The primary amino acid sequence of the *Piromyces* sp. XylA (Gen Bank Accession No. CAB76571, hereby incorporated by reference) is listed as SEQ ID NO: 15. The primary amino acid sequence of *Pichia stipitis* XYL3 (Gen Bank Accession No. CAA39066.1, hereby incorporated by reference) is listed as SEQ ID NO: 51. Relevant portions of the *Piromyces* sp. XylA/*Pichia stipitis* XYL3 transformation cassette are listed below. This cassette contained 5' and 3' *Prototheca moriformis* KE858 homologous recombination targeting sequences for genomic integration and are listed as SEQ ID NOs: 16 and 17. Also contained are (1) *S. cerevisae* suc2 sucrose invertase gene under the control of the *C. reinhardtii* beta-tubulin promoter and the *Chlorella vulgaris* nitrate reductase 3'UTR (SEQ ID NO: 18); (2) *Pichia stipitis* XYL3 under the control of the *Chlorella prototheocoides* EF1a promoter and 3'UTR; and (3) *Piromyces* sp. XylA under the control of the *Chlorella prototheocoides* actin promoter and EF1a 3'UTR. Positive clones were selected on sucrose-containing medium and plates and expression of the transgenes were confirmed using rabbit polyclonal antibodies generated against XylA or XYL3 in Western blots.

| Element | SEQ ID NO: |
|---|---|
| 5' *Prototheca moriformis* KE858 homologous recombination targeting sequence | 16 |
| 3' *Prototheca moriformis* KE858 homologous recombination targeting sequence | 17 |
| *S. cerevisae* suc2 invertase cassette | 18 |
| *C. prototheocoides* actin promoter | 19 |
| Codon optimized *Pichia stipitis* XYL3 coding region | 20 |
| *C. prototheocoides* EF1a 3'UTR | 21 |
| *Chlorella prototheocoides* EF1a promoter | 22 |
| Codon optimized *Piromyces* sp. XylA coding region | 23 |
| *C. prototheocoides* EF1a 3'UTR | 21 |

Once the XylA/XYL3 recipient strain was generated and confirmed using Western blots, the strain was then retransformed with one of two cassettes. The first cassette was an integrative transformation vector that carried a gene conferring resistance to the antibiotic G418 and an additional phosphate/pentose phosphate translocator gene XPT from *Arabidopsis thaliana* with the plastid transit peptide replaced with a transit peptide from an orthologous gene belonging to the same translocator family from *Prototheca moriformis*. The primary amino acid sequence (including the replaced transit peptide SEQ ID NO: 25) is listed in SEQ ID NO: 24. An alternative plastid transit peptide SEQ ID NO: 26 was also tried and was equally successful. The second cassette was an episomal (non-integrative) transformation vector containing a gene conferring resistance to the antibiotic G418 and an additional phosphate/pentose phosphate translocator gene XPT from *Arabidopsis thaliana* with the plastid transit peptide replaced with a transit peptide from an orthologous gene belonging to the same translocator family from *Prototheca moriformis* and the *Pichia stipitis* XYL2 gene, a xylitol dehydrogenase. In yeast (such as *Pichia*), XylA can be inhibited to some extent by xylitol. The preliminary experiment described above examining culture supernatant with non-transformed *Prototheca* cells showed detectable, low levels of xylitol in the medium, indicative of an endogenous reductase activity generating xylitol directly from xylose. This second construct containing the XYL2 xylitol dehydrogenase provides methods for alleviating such xyitol inhibition on XylA. Relevant portions of each of these two vectors are listed as SEQ ID NO: 32 and SEQ ID NO: 23, respectively, along with individual cassette components below. The XPT alone integrative cassette contained the 5' and 3' *Prototheca moriformis* 6S homologous recombination targeting sequence and a neomycin resistance gene under the control of the *C. reinhardtii* beta-tubulin promoter and *Chlorella vulgaris* nitrate reductase 3'UTR and the *A. thaliana* XPT gene with the replaced transit peptide sequence (as described above) under the control of the *Chlorella prototheocoides* actin promoter and EF1a 3'UTR. The episomal cassette contained a neomycin resistance gene under the control of *C. sorokiniana* Gdh promoter and *C. vulgaris* nitrate reductase 3'UTR; the *Pichia stipitis* XYL2 gene under the control of the *C. prototheocoides* actin promoter and EF1a 3'UTR; and the *A. thaliana* XPT gene under the control of *C. reinhardtii* beta-tubulin promoter and *C. prototheocoides* EF1a 3'UTR.

| Element | SEQ ID NO: |
|---|---|
| Integrative Cassette | |
| 5' *Prototheca moriformis* 6S homologous recombination targeting sequence | SEQ ID NO: 27 | source. Growth (measured by OD750 readings) and xylose consumption (measuring the amount of xylose remaining in the media) were measured at various time points during culture. No growth or xylose consumption was observed in the parental recipient strain, while both transgenic strains showed growth and xylose consumption. Table 5 summarizes the growth and xylose consumption results.

TABLE 5

Growth and Xylose Consumption Results.

| Genes expressed | Carbon source | OD750 | xylose (g/L) | OD750 | xylose (g/L) |
|---|---|---|---|---|---|
| | | Day 6 | | Day 8 | |
| no cells control | 2% xylose + 0.5% glucose | 0.0 | 21.3 | 0.0 | 20.5 |
| XylA, XYL3 | 2% xylose + 0.5% glucose | 4.7 | 20.4 | 5.1 | 17.9 |
| XylA, XYL3 | 2% xylose + 0.5% glucose | 4.4 | 21.3 | 4.6 | 19.1 |
| XylA, XYL3, XPT, XYL2 (duplicate 1) | 2% xylose + 0.5% glucose | 6.8 | 15 | 8.2 | 9.1 |
| XylA, XYL3, XPT, XYL2 (duplicate 2) | 2% xylose + 0.5% glucose | 6.3 | 16 | 7.4 | 11.4 |
| none | 2% xylose | 0.0 | 23.9 | 0.0 | 23.9 |
| XylA, XYL3 | 2% xylose | 0.0 | 23.9 | 0.1 | 21.7 |
| XylA, XYL3, XPT, XYL2 | 2% xylose | 1.0 | 21.2 | 2.6 | 19.3 |
| | | Day 7 | | Day 25 | |
| no cells control | 2% xylose + 0.5% glucose | 0 | 24.2 | 0 | 25.7 |
| XylA, XYL3 | 2% xylose + 0.5% glucose | 5.2 | 21.6 | 4.8 | 20.4 |
| XylA, XYL3, XPT | 2% xylose + 0.5% glucose | 5.6 | 18.3 | 10.6 | not detected |

-continued

| Element | SEQ ID NO: |
|---|---|
| 3' *Prototheca moriformis* 6S homologous recombination targeting sequence | SEQ ID NO: 28 |
| Neomycin cassette (*C. reinhardtii* β-tubulin promoter and *C. vulgaris* nitrate reductase 3'UTR) | SEQ ID NO: 29 |
| *C. protothecoides* actin promoter | SEQ ID NO: 19 |
| Codon-optimized *A. thaliana* XPT coding region | SEQ ID NO: 30 |
| *C. protothecoides* EF1a 3'UTR | SEQ ID NO: 21 |
| Nonintegrative Cassette | |
| Neomycin cassette (*C. sorokinana* Gdh promoter and *C. vulgaris* nitrate reductase 3'UTR) | SEQ ID NO: 31 |
| *C. protothecoides* actin promoter | SEQ ID NO: 19 |
| Codon-optimized *P. stipitis* XYL2 coding region | SEQ ID NO: 32 |
| *C. reinhardtii* β-tubulin promoter | SEQ ID NO: 33 |
| Codon-optimized *A. thaliana* XPT coding region | SEQ ID NO: 30 |
| *C. protothecoides* EF1a 3'UTR | SEQ ID NO: 21 |

Positive clones from both transformations were selected using sucrose-containing media/plates with the addition of 50 μg/ml G418.

Of the many positive clones from the transformation, two strains, one from each transformation, were selected for more detailed characterization. Both strains were grown on solid media plates containing 2% xylose as the sole carbon source. After 3-4 weeks of incubation, growth was measured for these transgenic strains and growth was observed for both transgenic strains, but not for the parental recipient strain containing only the XylA and XYL3 transgenes. Confirmation of these results was performed to test xylose consumption using a liquid media environment. Liquid cultures containing both transgenic strains (XylA, XYL3, XPT and XYL2; XylA XYL3 and XPT) and the parental recipient strain (XylA and XYL3 only) were set up using 2% xylose as the sole carbon Example 4

Generation of Engineered Microalgal Strains Expressing Transporters for Transport of Xylose into the Cytoplasm Four xylose-specific transporters (SUT1, GXS1, symporter, and XLT1, SEQ ID NOs: 37, 39, 41 and 43, respectively), some of which transport xylose actively and some of which allow passive diffusion of xylose into the cell, were expressed as transgenes in *Prototheca moriformis*. The gene for each xylose transporter was codon optimized (the codon-optimized coding regions are shown at SEQ ID NOs: 36, 38, 40 and 42, respectively) to allow for maximal expression in *Prototheca moriformis* and inserted into the genome of the microalgal cells under the control of the *Chlorella protothecoides* actin promoter and EF1a 3'UTR. Expression of each of the four genes was confirmed, as was their insertion and localization to the cell membrane. Confirmation of localization to the cell membrane included fusing DNA sequences encoding a fluorescent protein in-frame to the carboxyl terminus of each of the transporter transgenes and observing cells expressing the constructs utilizing fluorescence microscopy.

Micrographs of cells expressing each of the four transporters with a fluorescent protein fused to their carboxyl terminus showed that the transporters were expressed and localized to the cell membrane.

Example 5

Generation of Engineered Microalgal Strains Expressing Enzymes for Conversion of Xylose to Xylulose-5-Phosphate

*Prototheca moriformis* was engineered to express codon-optimized genes encoding oxido-reductase pathway enzymes XYL1, XYL2, or XYL3 (SEQ ID NOs: 34, 32, and 20, respectively), or isomerase pathway enzymes XylA or XYL3 (SEQ ID NO: 23 and 20, respectively) which correspond to two alternative pathways for the biochemical conversion of xylose to xylulose-5-phosphate. The two pathways share the same terminal enzyme (XYL3). Expression of each gene was confirmed at the RNA level. In addition, antibodies were generated against each gene product to permit further monitoring of expression at the protein level using Western blot analysis. Proteins corresponding to the expected size band were observed in extracts made from transgenic strains containing the corresponding inserted transgenes, but not the untransformed parental cells.

Although the expression of enzymes responsible for conversion of xylose to xylulose-5-phosphate did not appear to initially confer the ability to metabolize xylose in the *P. moriformis* cells, the ability to grow on xylose was conferred by increasing the copy number of the transgenes. The copy number of the genes encoding these enzymes was increased using a selectable marker. The original parent cells had a copy number of one for all three transgenes (suc2, XylA and XYL3) and did not appear to grow on xylose, but after growth under selection wherein the ability to grow on sucrose was imparted by a gene (suc2) adjacent to the genes encoding the xylose metabolism enzymes, three independent isolates that were characterized had increased the copy number of all three transgenes by three to fifty-fold. The isolates with increased copy number were assessed for growth on xylose. Isolate A, which displayed the greatest increase in copy number (~50 fold), had acquired the ability to grow on xylose. The original parent was unable to grow on xylose, as were the two isolates (B and C) that displayed only moderate increases in copy number (~3-4 fold). The ability of Isolate A to grow on xylose demonstrates that the transgenes were expressed, retain their enzymatic activity in a heterologous organism, and can confer on that organism the ability to utilize xylose.

Example 6

Generation of Engineered Microalgal Strains Expressing Translocators for Delivery of Xylulose-5-Phosphate to the Pentose Phosphate Metabolic Pathway

*Prototheca moriformis* was engineered to express one of three chimeric plant translocators that specifically transport xylulose-5-phosphate. The chimeric genes were produced by replacing the transit peptide encoded by the plant translocator gene (*Arabadopsis thaliana* XPT) with one of three transit peptides identified in endogenous translocators found in *P. moriformis* or the SAD gene of *C. protothecoides* in order to improve export of the xylulose-5-phosphate to the final cellular destination/compartment. The endogenous *Prototheca* transit peptides were identified by selecting partial DNA sequences of translocator orthologs in *P. moriformis* from contig assemblies and amplifying the selected sequences. Products arising from the amplification were cloned and sequenced, and the signal peptides were derived from the sequences obtained. The chimeric gene products were localized to the inner membrane of plastids; this was determined by fusing a fluorescent protein to the carboxyl terminus of the translocator chimera and examining the cells expressing the fusion utilizing fluorescence microscopy. The fluorescent signal appeared to be concentrated around the organellar-like structures within the cell, consistent with localization in the inner membrane of plastids. The three chimeric translocators GPT-A-XPT, GPT-F-XPT, and S106SAD-XPT are shown in SEQ ID NOs: 45, 47 and 49, respectively.

Example 7

Generation of Engineered Microalgal Strains Expressing Combinations of Genes for Xylose Metabolism As demonstrated in the examples herein, individual transgenes encoding xylose metabolism enzymes were successfully inserted into *Prototheca moriformis*. To investigate the effect of combining these various transgenes in a single cell, strains of *P. moriformis* containing certain combinations (see the Genotypes in Table 6) of the transgenes discussed in Examples 4-6 were prepared and screened for xylose metabolism.

Ten independent transformants of each unique genotype were clonally purified and assessed for growth on solid media containing only 2.5 percent xylose as the sole carbon source. Potential positive clones were further tested in liquid culture containing xylose as the sole carbon source. Growth of the cells was monitored by measuring the optical density of the culture. At the end of the experiment, the culture supernatant was analyzed for xylose content. Table 6 shows the final growth and xylose consumption of the ten best strains (Strains D to M) compared with negative controls (Strains A, B and C). Strains D to M are clearly capable of consuming xylose, as all of the xylose in the culture media had disappeared by the end of the experiment. In contrast, the same amount of xylose that was present at the beginning of the experiment was still detected at the end of the experiment in culture medium hosting the negative control strains A, B and C. The disappearance of xylose was accompanied by increases in cell density, indicating that carbon from xylose was being used to support cell growth. In contrast, the negative controls did not increase in cell density throughout the course of the experiment, and at the end of the experiment, the culture media contained about the same amount of xylose that had been in the media at the beginning of the experiment, indicating that xylose was not consumed at all, or that the amount of xylose consumed was very small.

TABLE 6

Xylose Utilization and Growth of Engineered Strains Compared with Negative Controls.

| Strain | Genotype | Percent of highest OD reached | Xylose remaining in the media, g/L |
|---|---|---|---|
| A | wildtype *P. moriformis* UTEX1435 | 5.0 | 27.1 |
| B | XylA, XYL3 | 5.7 | 24.4 |
| C | XYL2, XYL3 | 5.7 | 26.4 |
| D | XylA, XYL3, SUT1, GPT-F-XPT | 80.1 | 0.0 |
| E | XylA, XYL3, SUT1, GPT-F-XPT | 68.6 | 0.0 |
| F | XylA, XYL2, XYL3, XLT1, S106SAD-XPT | 100.0 | 0.0 |
| G | XylA, XYL1, XYL3, XLT1, S106SAD-XPT | 81.9 | 0.0 |

TABLE 6-continued

Xylose Utilization and Growth of Engineered Strains Compared with Negative Controls.

| Strain | Genotype | Percent of highest OD reached | Xylose remaining in the media, g/L |
|---|---|---|---|
| H | XylA, XYL1, XYL3, GXS1, GPT-A-XPT | 62.8 | 0.0 |
| I | XYL1, XYL2, XYL3, symporter, GPT-F-XPT | 67.9 | 0.0 |
| J | XYL1, XYL2, XYL3, GXS1, GPT-F-XPT | 81.8 | 0.0 |
| K | XYL2, XYL3, symporter, S106SAD-XPT | 74.4 | 0.0 |
| L | XYL2, XYL3, XLT1, S106SAD-XPT | 82.9 | 0.0 |
| M | XYL2, XYL3, GXS1, GPT-A-XPT | 92.0 | 0.0 |

Multiple strains with unique genotypes showed clear increases in biomass using xylose as the sole carbon source. These results demonstrate that microalgae were engineered to grow on xylose via transformation with multiple transgenes or groups of transgenes that transported xylose into the cell, biochemically converted xylose to xylulose-5-phosphate, and delivered xylulose-5-phosphate to an endogenous, central metabolic pathway.

Example 8

Lipid Production Capability of Xylose-Metabolizing Strains

Xylose-metabolizing strains A-M from Example 7 were evaluated for the ability to produce oil when grown using xylose as the sole carbon source. The xylose metabolizing stains were subjected to a lipid productivity assay, together with negative control strains. Cells were first grown up in media containing glucose, and then subjected to a lipid productivity phase using either glucose or xylose as the sole source of carbon. As sugar became depleted from the cultures, more of the corresponding sugar was fed to the cells until consumption ceased. At this point, the experiment was terminated and cells were analyzed for lipid content. Table 7 shows the results of the lipid analysis. All strains were normalized to Strain A's performance on glucose expressed as lipid as percent of dry cell weight. All engineered strains performed similarly to the parental, non-engineered control strains when glucose was fed to the cultures. The negative control strains (A, B, C) produced small amounts of lipid when cultured on xylose (6-8 percent of the amount normally made by Strain A in glucose). In contrast, all ten xylose metabolizing stains were capable of producing significant amounts of lipid when cultured in xylose. The best strain, L, accumulated up to 60 percent of the amount of lipid normally made by Strain A when grown on glucose.

TABLE 7

Lipid Productivity of Xylose-metabolizing Strains Grown in Glucose or Xylose.

| Strain | Genotype | Percent of control lipid production in glucose | Percent of control lipid production in xylose |
|---|---|---|---|
| A | wildtype P. moriformis UTEX1435 | 100 | 8.9 |
| B | XylA, XYL3 | 93.8 | 6.6 |
| C | XYL2, XYL3 | 93.5 | 6.2 |
| D | XylA, XYL3, SUT1, GPT-F-XPT | 93.5 | 32.4 |
| E | XylA, XYL3, SUT1, GPT-F-XPT | 103.8 | 34 |
| F | XylA, XYL2, XYL3, XLT1, S106SAD-XPT | 101 | 30.5 |
| G | XylA, XYL1, XYL3, XLT1, S106SAD-XPT | 100.8 | 32.2 |
| H | XylA, XYL1, XYL3, GXS1, GPT-A-XPT | 100 | 32.4 |
| I | XYL1, XYL2, XYL3, symporter, GPT-F-XPT | 104.7 | 45.7 |
| J | XYL1, XYL2, XYL3, GXS1, GPT-F-XPT | 99.9 | 30.6 |
| K | XYL2, XYL3, symporter, S106SAD-XPT | 102.5 | 35 |
| L | XYL2, XYL3, XLT1, S106SAD-XPT | 100.8 | 60.2 |
| M | XYL2, XYL3, GXS1, GPT-A-XPT | 102 | 27.8 |

These results show that the inserted pathways can divert carbon from xylose and utilize it to produce a lipid.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A recombinant oleaginous microalga comprising an exogenous gene that encodes a xylulose-5-phosphate translocator, wherein the xylulose-5-phosphate translocator is S106SAD-XPT having SEQ ID NO: 49, GPT-A-XPT having SEQ ID NO: 45, or GPT-F-XPT having SEQ ID NO: 47.

2. The recombinant oleaginous microalga of claim 1, further comprising one or more exogenous genes that encode a xylose transporter protein, a symporter protein, an oxidoreductase pathway protein, or a xylose isomerase pathway protein.

3. The recombinant oleaginous microalga of claim 1, wherein the xylulose-5-phosphate translocator is S106SAD-XPT having SEQ ID NO: 49.

4. The recombinant oleaginous microalga of claim 2, wherein the one or more exogenous genes that encode an oxidoreductase pathway protein is XYL3 having SEQ ID NO: 51.

5. The recombinant oleaginous microalga of claim 2, wherein the microalga is of the genus *Prototheca*.

6. The recombinant oleaginous microalga of claim 5, wherein the microalga is *Prototheca kruegani, Prototheca wickerhamii, Prototheca stagnora, Prototheca moriformis,* or *Prototheca zopfii.*

7. The recombinant oleaginous microalga of claim 1, wherein the xylulose-5-phosphate translocator is GPT-A-XPT having SEQ ID NO: 45.

8. The recombinant oleaginous microalga of claim 1, wherein the xylulose-5-phosphate translocator is GPT-F-XPT having SEQ ID NO: 47.

9. The recombinant oleaginous microalga of claim 2, wherein the one or more exogenous genes that encode a xylose isomerase pathway protein is XylA having SEQ ID NO: 15.

10. The recombinant oleaginous microalga of claim 2, wherein the one or more exogenous genes that encode an oxido-reductase pathway protein is XYL1 having SEQ ID NO: 35.

11. The recombinant oleaginous microalga of claim 2, wherein the one or more exogenous genes that encode an oxido-reductase pathway protein is XYL2 having SEQ ID NO: 50.

* * * * *

SEQUENCE LISTING

```
<160> NUMBER OF SEQ ID NOS: 52

<210> SEQ ID NO 1
<211> LENGTH: 541
<212> TYPE: DNA
<213> ORGANISM: Prototheca kruegani

<400> SEQUENCE: 1
tgttgaagaa tgagccggcg agttaaaaag agtggcatgg ttaaagaaaa tactctggag      60
ccatagcgaa agcaagttta gtaagcttag gtcattcttt ttagacccga aaccgagtga     120
tctacccatg atcagggtga agtgttagta aaataacatg gaggcccgaa ccgactaatg     180
ttgaaaaatt agcggatgaa ttgtgggtag gggcgaaaaa ccaatcgaac tcggagttag     240
ctggttctcc ccgaaatgcg tttaggcgca gcagtagcag tacaaataga ggggtaaagc     300
actgtttctt ttgtgggctt cgaaagttgt acctcaaagt ggcaaactct gaatactcta     360
```

```
tttagatatc tactagtgag accttggggg ataagctcct tggtcaaaag ggaaacagcc      420
cagatcacca gttaaggccc caaaatgaaa atgatagtga ctaaggatgt gggtatgtca      480
aaacctccag caggttagct tagaagcagc aatcctttca agagtgcgta atagctcact      540
g                                                                     541

<210> SEQ ID NO 2
<211> LENGTH: 573
<212> TYPE: DNA
<213> ORGANISM: Prototheca wickerhamii

<400> SEQUENCE: 2
tgttgaagaa tgagccggcg acttaaaata aatggcaggc taagagattt ataactcga       60 aacctaagcg aaagcaagtc ttaatagggc gtcaatttaa caaaacttta aataaattat     120
aaagtcattt attttagacc cgaacctgag tgatctaacc atggtcagga tgaaacttgg     180
gtgacaccaa gtggaagtcc gaaccgaccg atgttgaaaa atcggcggat gaactgtggt     240
tagtggtgaa ataccagtcg aactcagagc tagctggttc tccccgaaat gcgttgaggc     300
gcagcaatat atctcgtcta tctaggggta aagcactgtt tcggtgcggg ctatgaaaat     360
ggtaccaaat cgtggcaaac tctgaatact agaaatgacg atatattagt gagactatgg     420
gggataagct ccatagtcga gagggaaaca gcccagacca ccagttaagg ccccaaaatg     480
ataatgaagt ggtaaaggag gtgaaaatgc aaatacaacc aggaggttgg cttagaagca     540
gccatccttt aaagagtgcg taatagctca ctg                                  573

<210> SEQ ID NO 3
<211> LENGTH: 541
<212> TYPE: DNA
<213> ORGANISM: Prototheca stagnora

<400> SEQUENCE: 3
tgttgaagaa tgagccggcg agttaaaaaa aatggcatgg ttaaagatat ttctctgaag      60
ccatagcgaa agcaagtttt acaagctata gtcattttt ttagacccga aaccgagtga     120
tctacccatg atcagggtga agtgttggtc aaataacatg gaggcccgaa ccgactaatg     180
gtgaaaaatt agcggatgaa ttgtgggtag gggcgaaaaa ccaatcgaac tcggagttag     240
ctggttctcc ccgaaatgcg tttaggcgca gcagtagcaa cacaaataga ggggtaaagc     300
actgtttctt ttgtgggctt cgaaagttgt acctcaaagt ggcaaactct gaatactcta     360
tttagatatc tactagtgag accttggggg ataagctcct tggtcaaaag ggaaacagcc     420
cagatcacca gttaaggccc caaaatgaaa atgatagtga ctaaggacgt gagtatgtca     480
aaacctccag caggttagct tagaagcagc aatcctttca agagtgcgta atagctcact     540
g                                                                     541

<210> SEQ ID NO 4
<211> LENGTH: 541
<212> TYPE: DNA
<213> ORGANISM: Prototheca moriformis

<400> SEQUENCE: 4
tgttgaagaa tgagccggcg agttaaaaag agtggcatgg ttaaagataa ttctctggag      60
ccatagcgaa agcaagtttta acaagctaaa gtcacccttt ttagacccga aaccgagtga    120
tctacccatg atcagggtga agtgttggta aaataacatg gaggcccgaa ccgactaatg     180
```

```
gtgaaaaatt agcggatgaa ttgtgggtag gggcgaaaaa ccaatcgaac tcggagttag    240
ctggttctcc ccgaaatgcg tttaggcgca gcagtagcaa cacaaataga ggggtaaagc    300
actgtttctt ttgtgggctt cgaaagttgt acctcaaagt ggcaaactct gaatactcta    360
tttagatatc tactagtgag accttggggg ataagctcct tggtcaaaag ggaaacagcc    420
cagatcacca gttaaggccc caaaatgaaa atgatagtga ctaaggatgt gggtatgtta    480
aaacctccag caggttagct tagaagcagc aatcctttca agagtgcgta atagctcact    540
g                                                                   541

<210> SEQ ID NO 5
<211> LENGTH: 573
<212> TYPE: DNA
<213> ORGANISM: Prototheca moriformis

<400> SEQUENCE: 5
tgttgaagaa tgagccggcg acttaaaata aatggcaggc taagagaatt ataactcga     60 aacctaagcg aaagcaagtc ttaatagggc gctaattta a caaaacatta ataaaatct    120 aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctaggggta aagcactgtt tcggtgcggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                573

<210> SEQ ID NO 6
<211> LENGTH: 573
<212> TYPE: DNA
<213> ORGANISM: Prototheca wickerhamii

<400> SEQUENCE: 6
tgttgaagaa tgagccgtcg acttaaaata aatggcaggc taagagaatt ataactcga     60 aacctaagcg aaagcaagtc ttaatagggc gctaattta a caaaacatta ataaaatct    120 aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctaggggta aagcactgtt tcggtgcggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                573

<210> SEQ ID NO 7
<211> LENGTH: 541
<212> TYPE: DNA
<213> ORGANISM: Prototheca moriformis

<400> SEQUENCE: 7
tgttgaagaa tgagccggcg agttaaaaag agtggcgtgg ttaaagaaaa ttctctggaa     60
```

```
ccatagcgaa agcaagttta acaagcttaa gtcacttttt ttagacccga aaccgagtga    120
tctacccatg atcagggtga agtgttggta aaataacatg gaggcccgaa ccgactaatg    180
gtgaaaaatt agcggatgaa ttgtgggtag gggcgaaaaa ccaatcgaac tcggagttag    240
ctggttctcc ccgaaatgcg tttaggcgca gcagtagcaa cacaaataga ggggtaaagc    300
actgtttctt ttgtgggctc cgaaagttgt acctcaaagt ggcaaactct gaatactcta    360
tttagatatc tactagtgag accttggggg ataagctcct tggtcgaaag ggaaacagcc    420
cagatcacca gttaaggccc caaaatgaaa atgatagtga ctaaggatgt gagtatgtca    480
aaacctccag caggttagct tagaagcagc aatcctttca agagtgcgta atagctcact    540
g                                                                   541

<210> SEQ ID NO 8
<211> LENGTH: 541
<212> TYPE: DNA
<213> ORGANISM: Prototheca zopfii

<400> SEQUENCE: 8
tgttgaagaa tgagccggcg agttaaaaag agtggcatgg ttaaagaaaa ttctctggag     60
ccatagcgaa agcaagttta acaagcttaa gtcacttttt ttagacccga aaccgagtga    120
tctacccatg atcagggtga agtgttggta aaataacatg gaggcccgaa ccgactaatg    180
gtgaaaaatt agcggatgaa ttgtgggtag gggcgaaaaa ccaatcgaac tcggagttag    240
ctggttctcc ccgaaatgcg tttaggcgca gcagtagcaa cacaaataga ggggtaaagc    300
actgtttctt tcgtgggctt cgaaagttgt acctcaaagt ggcaaactct gaatactcta    360
tttagatatc tactagtgag accttggggg ataagctcct tggtcaaaag ggaaacagcc    420
cagatcacca gttaaggccc caaaatgaaa atgatagtga ctaaggatgt gagtatgtca    480
aaacctccag caggttagct tagaagcagc aatcctttca agagtgcgta atagctcact    540
g                                                                   541

<210> SEQ ID NO 9
<211> LENGTH: 565
<212> TYPE: DNA
<213> ORGANISM: Prototheca moriformis

<400> SEQUENCE: 9
tgttgaagaa tgagccggcg acttagaaaa ggtggcatgg ttaaggaaat attccgaagc     60
cgtagcaaaa gcgagtctga atagggcgat aaaatatatt aatatttaga atctagtcat    120
tttttctaga cccgaacccg ggtgatctaa ccatgaccag gatgaagctt gggtgatacc    180
aagtgaaggt ccgaaccgac cgatgttgaa aaatcggcgg atgagttgtg gttagcggtg    240
aaataccagt cgaacccgga gctagctggt tctccccgaa atgcgttgag gcgcagcagt    300
acatctagtc tatctagggg taaagcactg tttcggtgcg ggctgtgaga acggtaccaa    360
atcgtggcaa actctgaata ctagaaatga cgatgtagta gtgagactgt gggggataag    420
ctccattgtc aagagggaaa cagcccagac caccagctaa ggccccaaaa tggtaatgta    480
gtgacaaagg aggtgaaaat gcaaatacaa ccaggaggtt ggcttagaag cagccatcct    540
ttaaagagtg cgtaatagct cactg                                         565

<210> SEQ ID NO 10
<211> LENGTH: 1335
<212> TYPE: DNA
```

<213> ORGANISM: Chlorella sorokiniana

<400> SEQUENCE: 10

```
cgcctgcaac gcaagggcag ccacagccgc tcccacccgc cgctgaaccg acacgtgctt      60
gggcgcctgc cgcctgcctg ccgcatgctt gtgctggtga ggctgggcag tgctgccatg     120
ctgattgagg cttggttcat cgggtggaag cttatgtgtg tgctgggctt gcatgccggg     180
caatgcgcat ggtggcaaga gggcggcagc acttgctgga gctgccgcgg tgcctccagg     240
tggttcaatc gcggcagcca gagggatttc agatgatcgc gcgtacaggt tgagcagcag     300
tgtcagcaaa ggtagcagtt tgccagaatg atcggttcag ctgttaatca atgccagcaa     360
gagaagggt caagtgcaaa cacgggcatg ccacagcacg ggcaccgggg agtggaatgg     420
caccaccaag tgtgtgcgag ccagcatcgc cgcctggctg tttcagctac aacggcagga     480
gtcatccaac gtaaccatga gctgatcaac actgcaatca tcgggcgggc gtgatgcaag     540
catgcctggc gaagacacat ggtgtgcgga tgctgccggc tgctgcctgc tgcgcacgcc     600
gttgagttgg cagcaggctc agccatgcac tggatgcag ctgggctgcc actgcaatgt     660
ggtggatagg atgcaagtgg agcgaatacc aaaccctctg gctgcttgct gggttgcatg     720
gcatcgcacc atcagcagga gcgcatgcga agggactggc cccatgcacg ccatgccaaa     780
ccggagcgca ccgagtgtcc acactgtcac caggcccgca agctttgcag aaccatgctc     840
atggacgcat gtagcgctga cgtcccttga cggcgctcct ctcgggtgtg gaaacgcaa      900
tgcagcacag gcagcagagg cggcggcagc agagcggcgg cagcagcggc ggggggccacc    960
cttcttgcgg ggtcgcgccc cagccagcgg tgatgcgctg atcccaaacg agttcacatt    1020
catttgcatg cctggagaag cgaggctggg gcctttgggc tggtgcagcc cgcaatggaa    1080
tgcgggaccg ccaggctagc agcaaaggcg cctcccctac tccgcatcga tgttccatag    1140
tgcattggac tgcatttggg tggggcggcc ggctgtttct ttcgtgttgc aaaacgcgcc    1200
agctcagcaa cctgtcccgt gggtcccccg tgccgatgaa atcgtgtgca cgccgatcag    1260
ctgattgccc ggctcgcgaa gtaggcgccc tcctttctgc tcgccctctc tccgtcccgc    1320
cactagtggc gcgcc                                                   1335
```

<210> SEQ ID NO 11
<211> LENGTH: 1187
<212> TYPE: DNA
<213> ORGANISM: Parachlorella kessleri

<400> SEQUENCE: 11

```
gatcagacgg gcctgacctg cgagataatc aagtgctcgt aggcaaccaa ctcagcagct      60
gcttggtgtt gggtctgcag gatagtgttg cagggcccca aggacagcag gggaacttac     120
accttgtccc cgacccagtt ttatggagtg cattgcctca agagcctagc cggagcgcta     180
ggctacatac ttgccgcacc ggtatgaggg gatatagtac tcgcactgcg ctgtctagtg     240
agatgggcag tgctgcccat aaacaactgg ctgctcagcc atttgttggc ggaccattct     300
ggggggggcca gcaatgcctg actttcgggt agggtgaaaa ctgaacaaag actaccaaaa     360
cagaatttct tcctccttgg aggtaagcgc aggccggccc gcctgcgccc acatggcgct     420
ccgaacacct ccatagctgt aagggcgcaa acatggccgg actgttgtca gcactctttc     480
atggccatac aaggtcatgt cgagattagt gctgagtaag acactatcac cccatgttcg     540
attgaagccg tgacttcatg ccaacctgcc cctgggcgta gcagacgtat gccatcatga     600
ccactagccg acatgcgctg tcttttgcca ccaaaacaac tggtacaccg ctcgaagtcg     660
```

```
tgccgcacac ctccgggagt gagtccggcg actcctcccc ggcgggccgc ggccctacct    720
gggtagggtc gccatacgcc cacgaccaaa cgacgcagga ggggattggg gtagggaatc    780
ccaaccagcc taaccaagac ggcacctata ataataggtg gggggactaa cagccctata    840
tcgcaagctt tgggtgccta tcttgagaag cacgagttgg agtggctgtg tacggtcgac    900
cctaaggtgg gtgtgccgca gcctgaaaca aagcgtctag cagctgcttc tataatgtgt    960
cagccgttgt gtttcagtta tattgtatgc tattgtttgt tcgtgctagg gtggcgcagg   1020
cccacctact gtggcgggcc attggttggt gcttgaattg cctcaccatc taaggtctga   1080
acgctcactc aaacgccttt gtacaactgc agaactttcc ttggcgctgc aactacagtg   1140
tgcaaaccag cacatagcac tcccttacat cacccagcag tacaaca                1187
```

```
<210> SEQ ID NO 12
<211> LENGTH: 1414
<212> TYPE: DNA
<213> ORGANISM: Chlorella ellipsoidea

<400> SEQUENCE: 12
cgctgcgcac cagggccgcc agctcgctga tgtcgctcca aatgcggtcc cccgattttt     60
tgttcttcat cttctccacc ttggtggcct tcttggccag ggccttcagc tgcatgcgca    120
cagaccgttg agctcctgat cagcatcctc aggaggcccc ttgacaagca agcccctgtg    180
caagcccatt cacggggtac cagtggtgct gaggtagatg ggtttgaaaa ggattgctcg    240
gtcgattgct gctcatggaa ttggcatgtg catgcatgtt cacaatatgc caccaggctt    300
tggagcaaga gagcatgaat gccttcaggc aggttgaaag ttcctggggg tgaagaggca    360
gggccgagga ttggaggagg aaagcatcaa gtcgtcgctc atgctcatgt tttcagtcag    420
agtttgccaa gctcacagga gcagagacaa gactggctgc tcaggtgttg catcgtgtgt    480
gtggtggggg ggggggggtt aatacggtac gaaatgcact tggaattccc acctcatgcc    540
agcggaccca catgcttgaa ttcgaggcct gtggggtgag aaatgctcac tctgccctcg    600
ttgctgaggt acttcaggcc gctgagctca aagtcgatgc cctgctcgtc tatcagggcc    660
tgcacctctg ggctgaccgg ctcagcctcc ttcgcgggca tggagtaggc gccggcagcg    720
ttcatgtccg ggcccagggc agcggtggtg ccataaatgt cggtgatggt ggggagggg   780 gccgtcgcca caccattgcc gttgctggct gacgcatgca catgtggcct ggctggcacc    840
ggcagcactg tctccagcc agccagcaag tggctgttca ggaaagcggc catgttgttg    900
gtccctgcgc atgtaattcc ccagatcaaa ggagggaaca gcttggattt gatgtagtgc    960
ccaaccggac tgaatgtgcg atggcaggtc cctttgagtc tcccgaatta ctagcagggc   1020
actgtgacct aacgcagcat gccaaccgca aaaaatgat tgacagaaaa tgaagcggtg   1080
tgtcaatatt tgctgtattt attcgtttta atcagcaacc aagttcgaaa cgcaactatc   1140
gtggtgatca agtgaacctc atcagactta cctcgttcgg caaggaaacg gaggcaccaa   1200
attccaattt gatattatcg cttgccaagc tagagctgat ctttgggaaa ccaactgcca   1260
gacagtggac tgtgatggag tgccccgagt ggtggagcct cttcgattcg gttagtcatt   1320
actaacgtga accctcagtg aagggaccat cagaccagaa agaccagatc tcctcctcga   1380
caccgagaga gtgttgcggc agtaggacga caag                              1414
```

```
<210> SEQ ID NO 13
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 13
tgttgaagaa tgagccggcg ac                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagtgagcta ttacgcactc                                                 20

<210> SEQ ID NO 15
<211> LENGTH: 437
<212> TYPE: PRT
<213> ORGANISM: Piromyces sp.

<400> SEQUENCE: 15
```

Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His

```
                260             265             270
Ala Thr Leu Ala Gly His Thr Phe Glu His Glu Leu Ala Cys Ala Val
            275                 280                 285

Asp Ala Gly Met Leu Gly Ser Ile Asp Ala Asn Arg Gly Asp Tyr Gln
            290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
            355                 360                 365

Glu Asn Ala Ala Lys Leu Leu Gln Glu Ser Pro Tyr Thr Lys Met Lys
            370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
            405                 410                 415

Gly Glu Pro Lys Gln Thr Ser Gly Lys Gln Glu Leu Tyr Glu Ala Ile
            420                 425                 430

Val Ala Met Tyr Gln
            435

<210> SEQ ID NO 16
<211> LENGTH: 861
<212> TYPE: DNA
<213> ORGANISM: Prototheca moriformis

<400> SEQUENCE: 16
ccgtgatcac acaggtgcct tgcgagcgtg atcacactat tttgggggtc ctacagtact       60
gaaatggtga agtcgtac tgaaatcaag gatgaacaat gaaaatggtg ctgtggtggc       120
ttctcaaagg tcaagaatca gtcgctcgcg tcaggaaatc gcggcgtcaa ccagcgtggg       180
cgcggtcagt ggccccgcac tggtcaccat agcctctcct gccacagtag cgatcccctg       240
ggcgttcact ctcagcagcg gctgtactgc ctcccagatt ttcttcttct ggacctgcgg       300
gcgtgagagg atgagcaggg tggggccaag ggctcaatcc tgaacggccc tcattcggtt       360
tccaatccca caacacatac ccacagcagg tcagaccacg cattcgcacc atgcgcacca       420
ataacgtgtc cttacctgat tgggtgtggc aggctccgtg acaggagtg cctcgtcccc       480 cgcccagacc cgctcccccg tcacggcggc gtccgggacc cgcagcggct ccaccgcggt       540
gtgatccgcg ttggcggcgc agagcagcat cccagccgat ttgaccccgc gcatgctccg       600
aggcttgagg ttggccagca ccaccacccg ccggccgaca aggtcctcca gggtcacgtg       660
ccggaccagg ccactcacga tggtgcgagg gccccctcc tcgccgaggt cgatctgctc       720
gacgtacaga ctgcgacatg cgtggcgagt ggtcatcaga aggaagcagg tgtgcagaag       780
gggcacgtgg ttggtattga gagtagccaa agctttgtgc caatcagaaa gtcaacgcag       840
ctgcctgcct ggctcgcgta c                                                  861

<210> SEQ ID NO 17
<211> LENGTH: 448
<212> TYPE: DNA
<213> ORGANISM: Prototheca moriformis
```

<400> SEQUENCE: 17

```
gtacccatca gcatccgggt gaatcttggc ctccaagata tggccaatcc tcacatccag    60
cttggcaaaa tcgactagac tgtctgcaag tgggaatgtg gagcacaagg ttgcttgtag   120
cgatcgacag actggtgggg tacattgaca ggtgggcagc gccgcatcca tcgtgcctga   180
cgcgagcgcc gccggttgct cgcccgtgcc tgccgtcaaa gagcggcaga gaaatcggga   240
accgaaaacg tcacattgcc tgatgttgtt acatgctgga ctagactttc ttggcgtggg   300
tctgctcctc gccaggtgcg cgacgcctcg gggctgggtg cgagggagcc gtgcggccac   360
gcatttgaca agacccaaag ctcgcatctc agacggtcaa ccgttcgtat tatacattca   420
acatatggta catacgcaaa aagcatgc                                      448
```

<210> SEQ ID NO 18
<211> LENGTH: 2335
<212> TYPE: DNA
<213> ORGANISM: Saccharomyces cerevisae

<400> SEQUENCE: 18

```
ctttcttgcg ctatgacact tccagcaaaa ggtagggcgg gctgcgagac ggcttcccgg    60
cgctgcatgc aacaccgatg atgcttcgac cccccgaagc tccttcgggg ctgcatgggc   120
gctccgatgc cgctccaggg cgagcgctgt ttaaatagcc aggccccccga ttgcaaagac   180
attatagcga gctaccaaag ccatattcaa acacctagat cactaccact tctacacagg   240
ccactcgagc ttgtgatcgc actccgctaa gggggcgcct cttcctcttc gtttcagtca   300
caacccgcaa acgcgcgcc atgctgctgc aggccttcct gttcctgctg gccggcttcg   360
ccgccaagat cagcgcctcc atgacgaacg agacgtccga ccgcccctg gtgcacttca   420
cccccaacaa gggctggatg aacgacccca cggcctgtg gtacgacgag aaggacgcca   480
agtggcacct gtacttccag tacaacccga cgacaccgt ctgggggacg cccttgttct   540
ggggccacgc cacgtccgac gacctgacca actgggagga ccagcccatc gccatcgccc   600
cgaagcgcaa cgactccggc gccttctccg gctccatggt ggtggactac aacaacacct   660
ccggcttctt caacgacacc atcgacccgc gccagcgctg cgtggccatc tggacctaca   720
acaccccgga gtccgaggag cagtacatct cctacagcct ggacggcggc tacaccttca   780
ccgagtacca agaaccccc gtgctggccg ccaactccac ccagttccgc gacccgaagg   840
tcttctggta cgagccctcc cagaagtgga tcatgaccgc ggccaagtcc caggactaca   900
agatcgagat ctactcctcc gacgacctga gtcctggaa gctggagtcc gcgttcgcca   960
acgagggctt cctcggctac cagtacgagt gccccggcct gatcgaggtc cccaccgagc  1020
aggaccccag caagtcctac tgggtgatgt tcatctccat caaccccggc gccccggccg  1080
gcggctcctt caaccagtac ttcgtcggca gcttcaacgg cacccacttc gaggccttcg  1140
acaaccagtc ccgcgtggtg gacttcggca aggactacta cgccctgcag accttcttca  1200
acaccgaccc gacctacggg agcgccctgg gcatcgcgtg ggcctccaac tgggagtact  1260
ccgccttcgt gccaccaac ccctggcgct cctccatgtc cctcgtgcgc aagttctccc  1320
tcaacaccga gtaccaggcc aacccggaga cggagctgat caacctgaag gccgagccga  1380
tcctgaacat cagcaacgcc ggccctgga gccggttcgc caccaacacc acgttgacga  1440
aggccaacag ctacaacgtc gacctgtcca acagcaccgg cacctgag ttcgagctgg  1500
tgtacgccgt caacaccacc cagacgatct ccaagtccgt gttcgcggac ctctccctct  1560
ggttcaaggg cctggaggac cccgaggagt acctccgcat gggcttcgag gtgtccgcgt  1620
```

```
cctccttctt cctggaccgc gggaacagca aggtgaagtt cgtgaaggag aaccccctact    1680 tcaccaaccg catgagcgtg aacaaccagc ccttcaagag cgagaacgac ctgtcctact    1740
acaaggtgta cggcttgctg gaccagaaca tcctggagct gtacttcaac gacggcgacg    1800
tcgtgtccac caacacctac ttcatgacca ccgggaacgc cctgggctcc gtgaacatga    1860 cgacggggt ggacaaccctg ttctacatcg acaagttcca ggtgcgcgag gtcaagtgat    1920
taattaactc gaggcagcag cagctcggat agtatcgaca cactctggac gctggtcgtg    1980
tgatggactg ttgccgccac acttgctgcc ttgacctgtg aatatccctg ccgcttttat    2040
caaacagcct cagtgtgttt gatcttgtgt gtacgcgctt ttgcgagttg ctagctgctt    2100
gtgctatttg cgaataccac ccccagcatc cccttccctc gtttcatatc gcttgcatcc    2160
caaccgcaac ttatctacgc tgtcctgcta tccctcagcg ctgctcctgc tcctgctcac    2220 tgccctcgc acagccttgg tttgggctcc gcctgtattc tcctggtact gcaacctgta    2280
aaccagcact gcaatgctga tgcacgggaa gtagtgggat gggaacacaa atgga        2335

<210> SEQ ID NO 19
<211> LENGTH: 1176
<212> TYPE: DNA
<213> ORGANISM: Chlorella protothecoides

<400> SEQUENCE: 19
gagtttaggt ccagcgtccg tgggggggga cgggctggga gcttgggccg ggaagggcaa      60
gacgatgcag tccctctggg gagtcacagc cgactgtgtg tgttgcactg tgcggcccgc     120
agcactcaca cgcaaaatgc ctggccgaca ggcaggccct gtccagtgca acatccacgg     180
tccctctcat caggctcacc ttgctcattg acataacgga atgcgtaccg ctctttcaga     240
tctgtccatc cagagagggg agcaggctcc ccaccgacgc tgtcaaactt gcttcctgcc     300
caaccgaaaa cattattgtt tgaggggggg ggggggggg cagattgcat ggcgggatat     360
ctcgtgagga acatcactgg gacactgtgg aacacagtga gtgcagtatg cagagcatgt     420
atgctagggg tcagcgcagg aagggggcct ttcccagtct cccatgccac tgcaccgtat     480
ccacgactca ccaggaccag cttcttgatc ggcttccgct cccgtggaca ccagtgtgta     540
gcctctggac tccaggtatg cgtgcaccgc aaaggccagc cgatcgtgcc gattcctggg     600
gtggaggata tgagtcagcc aacttggggc tcagagtgca cactgggca cgatacgaaa     660 caacatctac accgtgtcct ccatgctgac acaccacagc ttcgctccac ctgaatgtgg     720
gcgcatgggc ccgaatcaca gccaatgtcg ctgctgccat aatgtgatcc agaccctctc     780
cgcccagatg ccgagcggat cgtgggcgct gaatagattc ctgtttcgat cactgtttgg     840
gtcctttcct tttcgtctcg gatgcgcgtc tcgaaacagg ctgcgtcggg ctttcggatc     900 cctttgctc cctccgtcac catcctgcgc gcgggcaagt tgcttgaccc tgggctggta     960
ccagggttgg agggtattac cgcgtcaggc cattcccagc ccggattcaa ttcaaagtct    1020
gggccaccac cctccgccgc tctgtctgat cactccacat tcgtgcatac actacgttca    1080
agtcctgatc caggcgtgtc tcgggacaag gtgtgcttga gtttgaatct caaggaccca    1140
ctccagcaca gctgctggtt gaccccgccc tcgcaa                              1176

<210> SEQ ID NO 20
<211> LENGTH: 1872
<212> TYPE: DNA
<213> ORGANISM: Pichia stipitis
```

<400> SEQUENCE: 20

```
atgaccacca ccccttcga cgccccgac aagctgttcc tgggcttcga cctgtccacc      60
cagcagctga agatcatcgt caccgacgag aacctggcgg ccctgaagac ctacaacgtg     120
gagttcgact cgatcaactc cagcgtgcag aagggcgtca tcgcgatcaa cgacgagatc     180
tccaagggcg ccatcatcag ccccgtctac atgtggctgg acgcgctgga ccacgtgttc     240
gaggacatga agaaggacgg cttcccttc aacaaggtcg tgggcatctc cggctcgtgc     300
cagcagcacg gcagcgtcta ctggtcccgc accgccgaga aggtgctgtc ggagctggac     360
gccgagtcgt ccctgagctc ccagatgcgc tcggccttca ccttcaagca cgcgcccaac     420
tggcaggacc acagcaccgg caaggagctg gaggagttcg agcgcgtgat cggcgcggac     480
gccctggcgg acatctcggg ctcccgcgcc cactaccgct tcaccggcct gcagatccgc     540
aagctgagca cccgcttcaa gcccgagaag tacaaccgca ccgcgcgcat ctccctggtg     600
tcgagcttcg tggcctcggt gctgctgggc cgcatcacca gcatcgagga ggccgacgcc     660
tgcggcatga acctgtacga catcgagaag cgcgagttca cgaggagct gctggccatc      720
gccgccggcg tgcaccccga gctggacggc gtggagcagg acggcgagat ctaccgcgcc     780
ggcatcaacg agctgaagcg caagctgggc ccgtgaagc ccatcaccta cgagtcggag      840
ggcgacatcg cctcctactt cgtgacccgc tacggcttca ccccgactg caagatctac      900
tccttcacgg cgacaacct ggccaccatc atctcgctgc cctggcccc aacgacgcc       960
ctgatctcgc tgggcaccag caccaccgtc ctgatcatca ccaagaacta cgccccctcc    1020
tcgcagtacc acctgttcaa gcaccccacc atgcccgacc actacatggg catgatctgc    1080
tactgcaacg gcagcctggc ccgcgagaag gtccgcgacg aggtcaacga aagttcaac     1140
gtcgaggaca agaagtcctg gacaagttc aacgagatcc tggacaagtc gaccgacttc    1200
aacaacaagc tgggcatcta cttccccctg gcgagatcg tgcccaacgc cgcggcccag     1260
atcaagcgca gcgtcctgaa ctccaagaac gagatcgtcg acgtggagct gggcgacaag    1320
aactggcagc ccgaggacga cgtctcgtcc atcgtggaga gccagaccct gagctgccgc    1380
ctgcgcaccg gccccatgct gtccaagtcc ggcgactcgt cggcgagctc ctccgcctcg    1440
ccccagcccg agggcgacgg caccgacctg cacaaggtct accaggacct ggtcaagaag    1500
ttcgcgacc tgtacaccga cggcaagaag cagaccttcg agagcctgac cgcccgcccc    1560
aaccgctgct actacgtcgg cggcgcgtcc aacaacggct cgatcatccg caagatgggc    1620
agcatcctgg cgcccgtcaa cggcaactac aaggtggaca tccccaacgc gtgcgccctg    1680
ggcggcgcct acaaggcctc ctggtcctac gagtgcgagg ccaagaagga gtggatcggc    1740
tacgaccagt acatcaaccg cctgttcgag gtgagcgacg agatgaactc gttcgaggtc    1800
aaggacaagt ggctggagta cgccaacggc gtcggcatgc tggccaagat ggagtcggag    1860
ctgaagcact ag                                                        1872
```

<210> SEQ ID NO 21
<211> LENGTH: 160
<212> TYPE: DNA
<213> ORGANISM: Chlorella protothecoides

<400> SEQUENCE: 21

```
acggagcgtc gtgcgggagg gagtgtgccg agcggggagt cccggtctgt gcgaggcccg      60
gcagctgacg ctggcgagcc gtacgccccg agggtccccc tcccctgcac cctcttcccc     120
ttccctctga cggccgcgcc tgttcttgca tgttcagcga                           160
```

<210> SEQ ID NO 22
<211> LENGTH: 1296
<212> TYPE: DNA
<213> ORGANISM: Chlorella protothecoides

<400> SEQUENCE: 22

```
gtttaggtcc agcgtccgtg ggggggcgt gagactcccc cctgaccttc gtatggcagg      60
gactcctact tgccaagtaa tcagttgaca atgccacttc aatgctcgtt gtggtacact     120
gacgcgggtc taacatactg gaagcatga attgccgaca tggactcagt tggagacagt    180
aacagctctt tgtgttctat cttcaggaac acatttggca gcgcacccat acagtggcgc    240
acacgcagct gtacctgatg tggctctatt cccacatgtt tcaacttgat ccaaaagtca    300
ctcagactct cagcagctag acttgatcgc atctttggcc aagaagatgc ttgcgcaact    360
ctaggaatgg aacgagaaaa gagcctgctc tgatcggata tttccattct ctggatggga    420
ctgagatgat tctgaagaaa tgctgctcga cttatttgga agaacagcac ctgacgcatg    480
ctttgaggct gctgtggctg ggatgtgctg tatttgtcag cattgagcat ctacgggtag    540
atggccataa ccacgcgctg cctatcatgc ggtgggttgt gtagaaaacg tacaatggac    600
agaaatcaat cccattgcga gcctagcgtg cagccatgcg ctccctctgt agccccgctc    660
caagacaaag ccagccaatg ccagaaccca catagagagg gtatcttcct aatgacctcg    720
cccatcattt cctccaaatt aactataatg ccttgattgt ggagttggct ttggcttgca    780
gctgctcgcg ctggcacttt tgtaggcagc acagggtatg ccagcgccga actttgtgcc    840
cttgagcagg ccacaagggc acaagactac accatgcagc tggtatactt ggaactgata    900
ccattcttac caagcaaggc acagcacagc ctgcaccgac tcactttgct tgagcggggc    960
acagcgccgc gactgatcct gcgagctgtg gggagttccg actgttctgg acctcggtct   1020
ctgaaagatg tgtacgatgg gatcaagtca ttcaagtatg ctcttcacat gagcaatcgg   1080
gggagacacg gtggccctaa aggtgttcat ctgattcaag tgtagtgggg gggtgctgtt   1140
tgtcccgggg cgcccccgc tccccgaccc cggagaaggg ccccagagga ctcggccgcc   1200
cacagaggaa taaccgggcg tggctcggcc ctgcgcctcc ctctttcaat atttcacctg   1260
gtgttcagtg cacggacacg taaagaacta gataca                             1296
```

<210> SEQ ID NO 23
<211> LENGTH: 1314
<212> TYPE: DNA
<213> ORGANISM: Piromyces sp.

<400> SEQUENCE: 23

```
atggccaagg agtacttccc ccagatccag aagatcaagt cgagggcaa ggacagcaag      60 aacccgctgg cgttccacta ctacgacgcg gagaaggagg tcatgggcaa gaagatgaag    120
gactggctgc gcttcgcgat ggcctggtgg cacacccctgt gcgcggaggg gcggaccag    180 ttcggcggcg gcaccaagtc gttcccgtgg aacgagggca ccgacgccat cgagatcgcc    240
aagcagaagg tcgacgcggg cttcgagatc atgcagaagc tgggcatccc ctactactgc    300
ttccacgacg tggacctggt gagcgagggc aactccatcg aggagtacga gtcgaacctg    360
aaggccgtgg tggcgtacct gaaggagaag cagaaggaga ccggcatcaa gctgctgtgg    420
tcgaccgcga acgtcttcgg ccacaagcgc tacatgaacg cgccagcac caaccccgac    480 ttcgacgtgg tcgcgcgcgc catcgtccag atcaagaacg cgatcgacgc cggcatcgag    540
```

```
ctgggcgccg agaactacgt gttctggggc ggccgcgagg gctacatgtc cctgctgaac    600
acggaccaga agcgcgagaa ggagcacatg gcgaccatgc tgacgatggc ccgcgactac    660
gcccgctcga agggcttcaa gggcaccttc ctgatcgagc ccaagccgat ggagcccacc    720
aagcaccagt acgacgtcga caccgagacc gcgatcggct tcctgaaggc gcacaacctg    780
gacaaggact tcaaggtgaa catcgaggtg aaccacgcca ccctggcggg ccacaccttc    840
gagcacgagc tggcgtgcgc cgtggacgcc ggcatgctgg gcagcatcga cgcgaaccgc    900
ggcgactacc agaacggctg ggacaccgac cagttcccca tcgaccagta cgagctggtg    960
caggcctgga tggagatcat ccgcggcggc ggcttcgtca ccggcggcac gaacttcgac   1020
gccaagaccc gccgcaactc caccgacctg gaggacatca tcatcgcgca cgtctcgggc   1080
atggacgcca tggcccgcgc cctggagaac gccgcgaagc tgctgcagga gagcccctac   1140
accaagatga agaaggagcg ctacgcctcc ttcgactcgg gcatcggcaa ggacttcgag   1200
gacggcaagc tgaccctgga gcaggtctac gagtacggca agaagaacgg cgagcccaag   1260
cagacctccg gcaagcagga gctgtacgag gccatcgtgg cgatgtacca gtag         1314
```

<210> SEQ ID NO 24
<211> LENGTH: 398
<212> TYPE: PRT
<213> ORGANISM: Arabidopsis thaliana

<400> SEQUENCE: 24

Met Arg Val Glu Ile Trp Arg Thr Gly Ser Pro Tyr Ala Val Pro Glu
1               5                   10                  15

Gly Leu Tyr Trp Val Glu Ser Asp Leu Gly Ala Ala Thr His Arg Glu
            20                  25                  30

Ser Glu Pro Ser Arg Gly Gly Thr Leu Leu Arg Gly Pro Ala Leu Thr
        35                  40                  45

Pro Arg Pro Pro Ala Cys Ile Arg Asp Leu Arg Arg Gly Arg Ala Ala
    50                  55                  60

Val Gly Ser Ser Asp Ser Asn Pro Asp Glu Lys Ser Asp Leu Gly Glu
65                  70                  75                  80

Ala Glu Lys Lys Glu Lys Lys Ala Lys Thr Leu Gln Leu Gly Ile Val
                85                  90                  95

Phe Gly Leu Trp Tyr Phe Gln Asn Ile Val Phe Asn Ile Phe Asn Lys
            100                 105                 110

Lys Ala Leu Asn Val Phe Pro Tyr Pro Trp Leu Leu Ala Ser Phe Gln
        115                 120                 125

Leu Phe Ala Gly Ser Ile Trp Met Leu Val Leu Trp Ser Phe Lys Leu
    130                 135                 140

Tyr Pro Cys Pro Lys Ile Ser Lys Pro Phe Ile Ile Ala Leu Leu Gly
145                 150                 155                 160

Pro Ala Leu Phe His Thr Ile Gly His Ile Ser Ala Cys Val Ser Phe
                165                 170                 175

Ser Lys Val Ala Val Ser Phe Thr His Val Ile Lys Ser Ala Glu Pro
            180                 185                 190

Val Phe Ser Val Ile Phe Ser Ser Leu Leu Gly Asp Ser Tyr Pro Leu
        195                 200                 205

Ala Val Trp Leu Ser Ile Leu Pro Ile Val Met Gly Cys Ser Leu Ala
    210                 215                 220

Ala Val Thr Glu Val Ser Phe Asn Leu Gly Gly Leu Ser Gly Ala Met
225                 230                 235                 240

```
Ile Ser Asn Val Gly Phe Val Leu Arg Asn Ile Tyr Ser Lys Arg Ser
            245                 250                 255

Leu Gln Ser Phe Lys Glu Ile Asp Gly Leu Asn Leu Tyr Gly Cys Ile
        260                 265                 270

Ser Ile Leu Ser Leu Leu Tyr Leu Phe Pro Val Ala Ile Phe Val Glu
    275                 280                 285

Gly Ser His Trp Val Pro Gly Tyr His Lys Ala Ile Ala Ser Val Gly
290                 295                 300

Thr Pro Ser Thr Phe Tyr Phe Trp Val Trp Leu Ser Gly Val Phe Tyr
305                 310                 315                 320

His Leu Tyr Asn Gln Ser Ser Tyr Gln Ala Leu Asp Glu Ile Ser Pro
            325                 330                 335

Leu Thr Phe Ser Val Gly Asn Thr Met Lys Arg Val Val Ile Ile
        340                 345                 350

Ser Thr Val Leu Val Phe Arg Asn Pro Val Arg Pro Leu Asn Ala Leu
    355                 360                 365

Gly Ser Ala Ile Ala Ile Cys Gly Thr Phe Leu Tyr Ser Gln Ala Thr
370                 375                 380

Ala Lys Lys Lys Lys Ile Glu Val Gly Gly Asp Lys Lys Asn
385                 390                 395

<210> SEQ ID NO 25
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Arg Val Glu Ile Trp Arg Thr Gly Ser Pro Tyr Ala Val Pro Glu
1               5                   10                  15

Gly Leu Tyr Trp Val Glu Ser Asp Leu Gly Ala Ala Thr His Arg Glu
            20                  25                  30

Ser Glu Pro Ser Arg Gly Gly Thr Leu Leu Arg Gly Pro Ala Leu Thr
        35                  40                  45

Pro Arg Pro Pro Ala Cys Ile Arg Asp Leu Arg Arg
    50                  55                  60

<210> SEQ ID NO 26
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Arg Val Glu Ile Trp Arg Thr Gly Ser Pro His Ala Ala Gln Gly
1               5                   10                  15

Gly Leu Cys Trp His Val Ser Asp Leu Gly Ala Ala Thr His Arg Glu
            20                  25                  30

Ser Glu Pro Ser Arg Gly Gly Thr Leu Phe Arg Gly Pro Ala Leu Thr
        35                  40                  45

Pro Arg Pro Pro Ala Cys Ile Arg Asp Leu Arg Arg
    50                  55                  60

<210> SEQ ID NO 27
<211> LENGTH: 713
```

```
<212> TYPE: DNA
<213> ORGANISM: Prototheca moriformis

<400> SEQUENCE: 27
gccgccgcca ctcctgctcg agcgcgcccg cgcgtgcgcc gccagcgcct tggccttttc      60
gccgcgctcg tgcgcgtcgc tgatgtccat caccaggtcc atgaggtctg ccttgcgccg     120
gctgagccac tgcttcgtcc gggcggccaa gaggagcatg agggaggact cctggtccag     180
ggtcctgacg tggtcgcggc tctgggagcg ggccagcatc atctggctct gccgcaccga     240
ggccgcctcc aactggtcct ccagcagccg cagtcgccgc cgaccctggc agaggaagac     300
aggtgagggg ggtatgaatt gtacagaaca accacgagcc ttgtctaggc agaatcccta     360
ccagtcatgg ctttacctgg atgacggcct gcaacagct gtccagcgac cctcgctgcc     420
gccgcttctc ccgcacgctt cttccagca ccgtgatggc gcgagccagc gccgcacgct     480
ggcgctgcgc ttcgccgatc tgaggacagt cggggaactc tgatcagtct aaaccccctt     540
gcgcgttagt gttgccatcc tttgcagacc ggtgagagcc gacttgttgt gcgccacccc     600
ccacaccacc tcctcccaga ccaattctgt caccttttttg gcgaaggcat cggcctcggc     660
ctgcagagag acagcagtg cccagccgct gggggttggc ggatgcacgc tca            713

<210> SEQ ID NO 28
<211> LENGTH: 734
<212> TYPE: DNA
<213> ORGANISM: Prototheca moriformis

<400> SEQUENCE: 28
ttgttttcca gaaggagttg ctccttgagc ctttcattct cagcctcgat aacctccaaa      60
gccgctctaa ttgtggaggg ggttcgaatt taaaagcttg gaatgttggt tcgtgcgtct     120
ggaacaagcc cagacttgtt gctcactggg aaaaggacca tcagctccaa aaaacttgcc     180
gctcaaaccg cgtacctctg ctttcgcgca atctgccctg ttgaaatcgc caccacattc     240
atattgtgac gcttgagcag tctgtaattg cctcagaatg tggaatcatc tgcccctgt     300
gcgagcccat gccaggcatg tcgcgggcga ggacacccgc cactcgtaca gcagaccatt     360
atgctacctc acaatagttc ataacagtga ccatatttct cgaagctccc caacgagcac     420
ctccatgctc tgagtggcca ccccccggcc ctggtgcttg cggagggcag gtcaaccggc     480
atggggctac cgaaatcccc gaccggatcc caccaccccc gcgatgggaa gaatctctcc     540
ccgggatgtg ggcccaccac cagcacaacc tgctggccca ggcgagcgtc aaaccatacc     600
acacaaatat ccttggcatc ggccctgaat tccttctgcc gctctgctac ccggtgcttc     660
tgtccgaagc aggggttgct agggatcgct ccgagtccgc aaaccttgt cgcgtggcgg     720
ggcttgttcg agct                                                       734

<210> SEQ ID NO 29
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
ctttcttgcg ctatgacact tccagcaaaa ggtagggcgg gctgcgagac ggcttcccgg      60
cgctgcatgc aacaccgatg atgcttcgac cccccgaagc tccttcgggg ctgcatgggc     120
gctccgatgc cgctccaggg cgagcgctgt ttaaatagcc aggcccccga ttgcaaagac     180
```

```
attatagcga gctaccaaag ccatattcaa acacctagat cactaccact tctacacagg    240
ccactcgagc ttgtgatcgc actccgctaa gggggcgcct cttcctcttc gtttcagtca    300
caacccgcaa actctagaat atcaatgatc gagcaggacg gcctccacgc cggctccccc    360
gccgcctggg tggagcgcct gttcggctac gactgggccc agcagaccat cggctgctcc    420
gacgccgccg tgttccgcct gtccgcccag ggccgccccg tgctgttcgt gaagaccgac    480
ctgtccggcg ccctgaacga gctgcaggac gaggccgccc gctgtcctg gctgccacc     540
accggcgtgc cctgcgccgc cgtgctggac gtggtgaccg aggccggccg cgactggctg    600
ctgctgggcg aggtgcccgg ccaggacctg ctgtcctccc acctggcccc cgccgagaag    660
gtgtccatca tggccgacgc catgcgccgc ctgcacaccc tggaccccgc cacctgcccc    720
ttcgaccacc aggccaagca ccgcatcgag gcgcccgca cccgcatgga ggccggcctg    780
gtggaccagg acgacctgga cgaggagcac cagggcctgg ccccgccga gctgttcgcc    840
cgcctgaagg cccgcatgcc cgacggcgag gacctggtgg tgacccacgg cgacgcctgc    900
ctgcccaaca tcatggtgga gaacggccgc ttctccggct tcatcgactg cggccgcctg    960
ggcgtggccg accgctacca ggacatcgcc ctggccaccc gcgacatcgc cgaggagctg    1020
ggcggcgagt gggccgaccg ctgacaattg gcagcagcag ctcggatagt atcgacacac    1080
tctggacgct ggtcgtgtga tggactgttg ccgccacact gctgccttg acctgtgaat    1140
atccctgccg cttttatcaa acagcctcag tgtgtttgat cttgtgtgta cgcgcttttg    1200
cgagttgcta gctgcttgtg ctatttgcga ataccacccc cagcatcccc ttccctcgtt    1260
tcatatcgct tgcatcccaa ccgcaactta tctacgctgt cctgctatcc ctcagcgctg    1320
ctcctgctcc tgctcactgc ccctcgcaca gccttggttt gggctccgcc tgtattctcc    1380
tggtactgca acctgtaaac cagcactgca atgctgatgc acgggaagta gtgggatggg    1440
aacacaaatg ga                                                        1452

<210> SEQ ID NO 30
<211> LENGTH: 1197
<212> TYPE: DNA
<213> ORGANISM: Arabidopsis thaliana

<400> SEQUENCE: 30
atgagggtgg agatctggag aactgggtcg ccttatgccg tgccggaggg cttgtactgg     60
gttgagagtg atttgggtgc ggcgacgcac cgggagagcg agcccagccg aggcggtact    120
ttgctccgcg ggcccgccct cacgcccgc ccacccgcat gcatccgcga cctgcgcagg    180
ggcgcgcccg ccgtgggctc ctccgactcg aaccccgacg agaagtccga cctgggcgag    240
gccgagaaga aggagaagaa ggccaagacc ctgcagctgg catcgtgtt cggcctgtgg    300
tacttccaga acatcgtctt caacatcttc aacaagaagg ccctgaacgt gttcccctac    360
ccctggctcc tggcctcctt ccagctgttc gccggctcca tctggatgct ggtgctgtgg    420
tcgttcaagc tgtaccctg ccccaagatc tcgaagccgt tcatcatcgc gctgctgggc    480
cccgccctgt tccacaccat cggccacatc tccgcctgcg tgtccttctc caaggtggcc    540
gtctcgttca cccacgtgat caagtccgcc gagcccgtgt tctccgtgat cttctcctcg    600
ctgctgggcg actcctaccc cctggccgtg tggctgtcca tcctgcccat cgtgatgggc    660
tgctccctgg ccgccgtgac cgaggtctcg ttcaacctgg cggcctgtc cggcgccatg    720
atctccaacg tgggcttcgt gctgcgcaac atctactcca agcgctccct gcagtccttc    780
```

```
aaggagatcg acggcctcaa cctgtacggc tgcatctcca tcctgtccct gctgtacctg    840
ttccccgtgg ccatcttcgt ggagggctcc cactgggtgc ccggctacca caaggccatc    900
gcctccgtgg gcaccccctc caccttctac ttctgggtct ggctgtcggg cgtgttctac    960
cacctgtaca accagtcctc ctaccaggcc ctggacgaga tctcccccct gaccttctcg   1020
gtcggcaaca ccatgaagcg cgtggtggtg atcatctcca ccgtgctggt gttccgcaac   1080
cccgtgcgcc ccctgaacgc cctgggctcc gccatcgcca tctgcggcac cttcctgtac   1140
tcccaggcca ccgccaagaa gaagaagatc gaggtgggcg gcgacaagaa gaactga      1197
```

```
<210> SEQ ID NO 31
<211> LENGTH: 1333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
```

```
ggtacccgcc tgcaacgcaa gggcagccac agccgctccc acccgccgct gaaccgacac     60
gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg gcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct tgcagaacc    840 atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgccccagc cagcggtgat gcgctgatcc caaacgagtt   1020
cacattcatt tgcatgcctg gagaagcgag gctgggcct ttgggctggt gcagcccgca   1080
atggaatgcg ggaccgccag gctagcagca aaggcgcctc ccctactccg catcgatgtt   1140
ccatagtgca ttggactgca tttgggtggg gcggccggct gtttctttcg tgttgcaaaa   1200
cgcgccagct cagcaacctg tcccgtgggt ccccgtgcc gatgaaatcg tgtgcacgcc   1260
gatcagctga ttgcccggct cgcgaagtag gcgccctcct ttctgctcgc cctctctccg   1320
tcccgcctct aga                                                       1333
```

```
<210> SEQ ID NO 32
<211> LENGTH: 1092
<212> TYPE: DNA
<213> ORGANISM: Pichia stipitis

<400> SEQUENCE: 32
```

```
atgaccgcca acccctccct ggtgctgaac aagatcgacg acatctcgtt cgagacctac      60
gacgcgccgg agatcagcga gcccaccgac gtcctggtgc aggtcaagaa gaccggcatc     120
tgcggctccg acatccactt ctacgcccac ggccgcatcg gcaacttcgt cctgaccaag     180
ccgatggtgc tgggccacga gtcggcgggc accgtggtcc aggtcggcaa gggcgtgacc     240
agcctgaagg tcggcgacaa cgtcgccatc gagcccggca tcccctcccg cttctcggac     300
gagtacaaga gcggccacta caacctgtgc ccgcacatgg cgttcgccgc gaccccaac      360 tccaaggagg gcgagcccaa cccgcccggc accctgtgca agtacttcaa gtcgcccgag     420
gacttcctgg tcaagctgcc cgaccacgtg agcctggagc tgggcgccct ggtcgagccg     480
ctgtccgtcg gcgtccacgc gtcgaagctg ggctccgtcg cgttcggcga ctacgtggcg     540
gtgttcggcg cgggccccgt gggcctgctg cggccgcgg tggccaagac cttcggcgcg      600
aagggcgtca tcgtcgtgga catcttcgac aacaagctga agatggccaa ggacatcggc     660
gcggccaccc acaccttcaa ctcgaagacc ggcggctcgg aggagctgat caaggccttc     720
ggcggcaacg tcccgaacgt ggtgctggag tgcaccggcg ccgagccctg catcaagctg     780
ggcgtcgacg cgatcgcccc cggcggccgc ttcgtgcagg tgggcaacgc ggccggcccc     840
gtcagcttcc ccatcaccgt gttcgccatg aaggagctga ccctgttcgg ctccttccgc     900
tacggcttca cgactacaa gaccgccgtc ggcatcttcg acaccaacta ccagaacggc      960
cgcgagaacg ccccccatcga cttcgagcag ctgatcaccc accgctacaa gttcaaggac    1020
gccatcgagg cctacgacct ggtccgcgcc ggcaagggcg ccgtgaagtg cctgatcgac     1080
ggccccgagt ag                                                         1092

<210> SEQ ID NO 33
<211> LENGTH: 312
<212> TYPE: DNA
<213> ORGANISM: Chlamydomonas reinhardtii

<400> SEQUENCE: 33
ctttcttgcg ctatgacact tccagcaaaa ggtagggcgg gctgcgagac ggcttcccgg      60
cgctgcatgc aacaccgatg atgcttcgac ccccgaagc tccttcgggg ctgcatgggc      120
gctccgatgc cgctccaggg cgagcgctgt ttaaatagcc aggcccccga ttgcaaagac     180
attatagcga gctaccaaag ccatattcaa acacctagat cactaccact tctacacagg     240
ccactcgagc ttgtgatcgc actccgctaa ggggcgcct cttcctcttc gtttcagtca      300
caacccgcaa ac                                                         312

<210> SEQ ID NO 34
<211> LENGTH: 957
<212> TYPE: DNA
<213> ORGANISM: Pichia stipitis

<400> SEQUENCE: 34 atgcccctcca tcaagctgaa ctcgggctac gacatgccgg ccgtcggctt cggctgctgg      60
aaggtggacg tcgacaccctg cagcgagcag atctaccgcg cgatcaagac cggctaccgc    120
ctgttcgacg gcgccgagga ctacgcgaac gagaagctgg tcggcgccgg cgtgaagaag     180
gccatcgacg agggcatcgt gaagcgcgag gacctgttcc tgacctccaa gctgtggaac     240
aactaccacc ccccgacaa cgtggagaag gcgctgaacc gcaccctgtc ggacctccag      300
gtcgactacg tggacctctt cctgatccac ttccgggtga ccttcaagtt cgtgcccctg     360
gaggagaagt acccgccgg cttctactgc ggcaagggcg acaacttcga ctacgaggac     420
```

```
gtcccgatcc tggagacctg gaaggccctg gagaagctgg tcaaggcggg caagatccgc    480
tccatcggcg tgagcaactt ccccggcgcc ctgctgctgg acctgctgcg cggcgcgacc    540
atcaagccgt ccgtcctgca ggtcgagcac caccoctacc tgcagcagcc ccgcctgatc    600
gagttcgccc agtcccgcgg catcgccgtg accgcgtaca gctccttcgg cccccagtcc    660
ttcgtggagc tgaaccaggg ccgcgccctg aacacctcgc ccctgttcga aacgagacg     720
atcaaggcca tcgccgccaa gcacggcaag agccccgccc aggtcctgct cgctggtcc     780
tcgcagcgcg gcatcgcgat catccccaag agcaacaccg tgccgcgcct gctggagaac    840
aaggacgtga actccttcga cctggacgag caggacttcg ccgacatcgc caagctggac    900
atcaacctgc gcttcaacga ccctgggac tgggacaaga tccccatctt cgtgtag        957
```

<210> SEQ ID NO 35
<211> LENGTH: 318
<212> TYPE: PRT
<213> ORGANISM: Pichia stipitis

<400> SEQUENCE: 35

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
```

275                 280                 285
Asp Glu Gln Asp Phe Ala Asp Ile Ala Lys Leu Asp Ile Asn Leu Arg
        290                 295                 300

Phe Asn Asp Pro Trp Asp Trp Asp Lys Ile Pro Ile Phe Val
305                 310                 315

<210> SEQ ID NO 36
<211> LENGTH: 1669
<212> TYPE: DNA
<213> ORGANISM: Pichia stipitis

<400> SEQUENCE: 36

| | |
|---|---|
| atgtcctccc aggacatccc ctccggcgtg cagaccccct ccaacgcctc gttcctggag | 60 |
| aaggacgagg acaagatcga ggaggtgccc cagaaccacg acgcgaccct ggtcgccctg | 120 |
| gagtccaagg gcatctccga gtacctgctg atctgcttct tctgcctgct cgtcgccttc | 180 |
| ggcggcttcg tcttcggctt cgacaccggc accatctccg gcttcgtgaa catgtccgac | 240 |
| ttcctggagc gcttcggcca gacccgcgcc gacggcaccc actacctgtc caacgtgcgc | 300 |
| gtgggcctgc tggtgtccat cttcaacatc ggctgcgcca tcggcggcat cttcctgtcc | 360 |
| aagatcggcg acgtgtacgg ccgccgcgtc ggcatcatgg cctccatggt gatctacgtg | 420 |
| gtcggcatca tcgtgcagat cgcctcccag cacgcgtggt accaggtcat gatcggccgc | 480 |
| gccatcaccg gctggcggt cggcaccgtg tccgtcctgt cgccgctgtt catcggcgag | 540 |
| tcctccccca gcacctgcg cggcaccctg gtgtactgct ccagctgtg catcaccctg | 600 |
| ggcatcttca tcggctactg cgtgacgtac ggcacgaagc gcctgtccga ctcccgccag | 660 |
| tggcgcgtgc ccctgggcct gtgcttcctg tgggcgatct tcctggtggt gggcatgctg | 720 |
| gccatgcccg agtcccccg ctacctggtg gagaagaagc gcatcgagga cgccaagaag | 780 |
| tccgtggccc gctccaacaa gctgtccccc gaggacccct cggtctacac ggagatccag | 840 |
| ctgatccagg ccggcatcga ccgcgaggcg atcgccggct ccgcctcctg gaccgagctg | 900 |
| atcaccggca gcccgccat cttccgccgc gtggtgatgg catcatcat gcagtccctg | 960 |
| cagcagctga ccggcgtgaa ctacttcttc tactacggca ccaccatctt ccaggccgtc | 1020 |
| ggcctgaagg actccttcca gacctccatc atcctgggcg tggtgaactt cgccgccacg | 1080 |
| tttatcggca tctgggccat cgagcgcttt ggccgccgct cctgcctcct ggtgggctcc | 1140 |
| gccggcatgt tcgtgtgctt catcatctac tccaccatcg gctccttcca cctgtacaag | 1200 |
| gacggcgagt acaacaacga caacacctac aagccctccg caacgcccct gatcttcatc | 1260 |
| acctgcctct tcatcgtctt cttcgcctcc acctgggccg gcggcgtgta ccaccatcatc | 1320 |
| tcggagtcct accccctgcg catccgctcc aaggcgatgg cgatcgcgac cgccgccaac | 1380 |
| tgggtctttg gcttcctgat ctccttcttc accccttca tcgtgagcgc catccacttc | 1440 |
| aagttcggct acgtgttctc cggctgcctg ctgttctcgt tcttctacgt gtacttcttc | 1500 |
| gtggtggaga ccaagggcct gtccctggag gacgtggacg agctgtacgc ctccaacgtg | 1560 |
| gtgccctgga agtcctccaa gtgggtcccc ccctcgacgg cggcgatggc caccgaggcc | 1620 |
| ggctacgccg ccgacgagaa gcccgtcgac gagcacgtgt gatacgtac | 1669 |

<210> SEQ ID NO 37
<211> LENGTH: 553
<212> TYPE: PRT
<213> ORGANISM: Pichia stipitis

<400> SEQUENCE: 37

-continued

```
Met Ser Ser Gln Asp Ile Pro Ser Gly Val Gln Thr Pro Ser Asn Ala
1               5                   10                  15

Ser Phe Leu Glu Lys Asp Glu Asp Lys Ile Glu Val Pro Gln Asn
            20              25                  30

His Asp Ala Thr Leu Val Ala Leu Glu Ser Lys Gly Ile Ser Glu Tyr
        35                  40                  45

Leu Leu Ile Cys Phe Phe Cys Leu Leu Val Ala Phe Gly Gly Phe Val
50                      55                  60

Phe Gly Phe Asp Thr Gly Thr Ile Ser Gly Phe Val Asn Met Ser Asp
65                  70              75                  80

Phe Leu Glu Arg Phe Gly Gln Thr Arg Ala Asp Gly Thr His Tyr Leu
                85                  90                  95

Ser Asn Val Arg Val Gly Leu Leu Val Ser Ile Phe Asn Ile Gly Cys
            100                 105                 110

Ala Ile Gly Gly Ile Phe Leu Ser Lys Ile Gly Asp Val Tyr Gly Arg
            115                 120                 125

Arg Val Gly Ile Met Ala Ser Met Val Ile Tyr Val Val Gly Ile Ile
            130                 135                 140

Val Gln Ile Ala Ser Gln His Ala Trp Tyr Gln Val Met Ile Gly Arg
145                 150                 155                 160

Ala Ile Thr Gly Leu Ala Val Gly Thr Val Ser Val Leu Ser Pro Leu
            165                 170                 175

Phe Ile Gly Glu Ser Ser Pro Lys His Leu Arg Gly Thr Leu Val Tyr
            180                 185                 190

Cys Phe Gln Leu Cys Ile Thr Leu Gly Ile Phe Ile Gly Tyr Cys Val
            195                 200                 205

Thr Tyr Gly Thr Lys Arg Leu Ser Asp Ser Arg Gln Trp Arg Val Pro
            210                 215                 220

Leu Gly Leu Cys Phe Leu Trp Ala Ile Phe Leu Val Val Gly Met Leu
225                 230                 235                 240

Ala Met Pro Glu Ser Pro Arg Tyr Leu Val Glu Lys Lys Arg Ile Glu
                245                 250                 255

Asp Ala Lys Lys Ser Val Ala Arg Ser Asn Lys Leu Ser Pro Glu Asp
            260                 265                 270

Pro Ser Val Tyr Thr Glu Ile Gln Leu Ile Gln Ala Gly Ile Asp Arg
            275                 280                 285

Glu Ala Ile Ala Gly Ser Ala Ser Trp Thr Glu Leu Ile Thr Gly Lys
            290                 295                 300

Pro Ala Ile Phe Arg Arg Val Val Met Gly Ile Met Gln Ser Leu
305                 310                 315                 320

Gln Gln Leu Thr Gly Val Asn Tyr Phe Phe Tyr Tyr Gly Thr Thr Ile
            325                 330                 335

Phe Gln Ala Val Gly Leu Lys Asp Ser Phe Gln Thr Ser Ile Ile Leu
            340                 345                 350

Gly Val Val Asn Phe Ala Ala Thr Phe Ile Gly Ile Trp Ala Ile Glu
            355                 360                 365

Arg Phe Gly Arg Arg Ser Cys Leu Leu Val Gly Ser Ala Gly Met Phe
            370                 375                 380

Val Cys Phe Ile Ile Tyr Ser Thr Ile Gly Ser Phe His Leu Tyr Lys
385                 390                 395                 400

Asp Gly Glu Tyr Asn Asn Asp Asn Thr Tyr Lys Pro Ser Gly Asn Ala
                405                 410                 415
```

```
Leu Ile Phe Ile Thr Cys Leu Phe Ile Val Phe Ala Ser Thr Trp
            420                 425                 430

Ala Gly Gly Val Tyr Thr Ile Ile Ser Glu Ser Tyr Pro Leu Arg Ile
        435                 440                 445

Arg Ser Lys Ala Met Ala Ile Ala Thr Ala Ala Asn Trp Val Phe Gly
    450                 455                 460

Phe Leu Ile Ser Phe Phe Thr Pro Phe Ile Val Ser Ala Ile His Phe
465                 470                 475                 480

Lys Phe Gly Tyr Val Phe Ser Gly Cys Leu Leu Phe Ser Phe Phe Tyr
                485                 490                 495

Val Tyr Phe Phe Val Val Glu Thr Lys Gly Leu Ser Leu Glu Asp Val
            500                 505                 510

Asp Glu Leu Tyr Ala Ser Asn Val Val Pro Trp Lys Ser Ser Lys Trp
        515                 520                 525

Val Pro Pro Ser Thr Ala Ala Met Ala Thr Glu Ala Gly Tyr Ala Ala
    530                 535                 540

Asp Glu Lys Pro Val Asp Glu His Val
545                 550

<210> SEQ ID NO 38
<211> LENGTH: 1576
<212> TYPE: DNA
<213> ORGANISM: Candida intermedia

<400> SEQUENCE: 38
atgggcctgg aggacaaccg catggtcaag cgcttcgtca acgtcggcga gaagaaggcc      60
ggctcgacgg ccatggccat catcgtgggc ctgttcgccg cctccggcgg cgtgctgttc     120
ggctacgaca ccggcaccat ctcgggcgtg atgaccatgg actacgtgct ggcccgctac     180
ccctccaaca agcactcgtt caccgccgac gagtcctcgc tgatcgtgtc catcctgtcc     240
gtgggcacct tcttcggcgc cctgtgcgcc cccttcctga cgacaccct gggccgccgc      300 tggtgcctga tcctgtcggc cctgatcgtc ttcaacatcg gcgcgatcct gcaggtgatc     360
tccaccgcca tcccgctgct gtgcgccggc cgcgtgatcg ccggcttcgg cgtcggcctg     420
atctccgcga cgatccccct gtaccagtcc gagaccgccc ccaagtggat ccgcggcgcc     480
atcgtgtcct gctaccagtg ggccatcacc atcggcctgt cctggcctc ctgcgtgaac      540 aagggcaccg agcacatgac caactccggc tcctaccgca tccccctggc gatccagtgc     600
ctgtggggcc tcatcctggg catcggcatg atcttcctgc ccgagacccc ccgcttctgg     660
atctcgaagg gcaaccagga gaaggccgcc gagtccctgg cccgcctgcg caagctgccc     720
atcgaccacc ccgactccct ggaggagctg cgcgacatca ccgccgccta cgagttcgag     780
accgtgtacg gcaagtcgtc gtggtcccag gtgttctccc acaagaacca ccagctgaag     840
cgcctgttca ccggcgtcgc gatccaggcg ttccagcagc tgaccggcgt gaacttcatc     900
ttctactacg cacgacgtt cttcaagcgc gcgggcgtca acggcttcac catctccctg     960
gccaccaaca tcgtgaacgt gggctccacc atccccggca tcctgctgat ggaggtgctc    1020
ggccgccgca catgctgat gggcggcgcc accggcatgt ccctgtccca gctgatcgtg    1080
gcgatcgtcg gcgtggccac ctccgagaac aacaagtcct cccagtccgt gctggtcgcg    1140
ttctcctgca tcttcatcgc cttcttcgcc gccacctggg gcccctgcgc ctgggtggtg    1200
gtgggcgagc tgttcccct gcgcaccgc gccaagtccg tgtccctgtg caccgcctcc      1260
aactggctgt ggaactgggg catcgcctac gccacccct acatggtgga cgaggacaag   1320
```

-continued

```
ggcaacctgg gctccaacgt cttcttcatc tggggcggct tcaacctggc ctgcgtgttc    1380
ttcgcctggt acttcatcta cgagaccaag ggcctgtccc tggagcaggt cgacgagctg    1440
tacgagcacg tgtccaaggc ctggaagtcc aagggcttcg tgccctccaa gcactccttc    1500
cgcgagcagg tggaccagca gatggactcc aagaccgagg ccatcatgtc cgaggaggcg    1560
tcggtgtgat acgtac                                                    1576
```

```
<210> SEQ ID NO 39
<211> LENGTH: 522
<212> TYPE: PRT
<213> ORGANISM: Candida intermedia

<400> SEQUENCE: 39
```

| | | | | | | | | | | | | | | |
|---|---|---|---|---|---|---|---|---|---|---|---|---|---|---|
| Met | Gly | Leu | Glu | Asp | Asn | Arg | Met | Val | Lys | Arg | Phe | Val | Asn | Val | Gly |
| 1 | | | | 5 | | | | | 10 | | | | | 15 | |
| Glu | Lys | Lys | Ala | Gly | Ser | Thr | Ala | Met | Ala | Ile | Ile | Val | Gly | Leu | Phe |
| | | | 20 | | | | | 25 | | | | | 30 | | |
| Ala | Ala | Ser | Gly | Gly | Val | Leu | Phe | Gly | Tyr | Asp | Thr | Gly | Thr | Ile | Ser |
| | | 35 | | | | | 40 | | | | | 45 | | | |
| Gly | Val | Met | Thr | Met | Asp | Tyr | Val | Leu | Ala | Arg | Tyr | Pro | Ser | Asn | Lys |
| | 50 | | | | | 55 | | | | | 60 | | | | |
| His | Ser | Phe | Thr | Ala | Asp | Glu | Ser | Ser | Leu | Ile | Val | Ser | Ile | Leu | Ser |
| 65 | | | | | 70 | | | | | 75 | | | | | 80 |
| Val | Gly | Thr | Phe | Phe | Gly | Ala | Leu | Cys | Ala | Pro | Phe | Leu | Asn | Asp | Thr |
| | | | | 85 | | | | | 90 | | | | | 95 | |
| Leu | Gly | Arg | Arg | Trp | Cys | Leu | Ile | Leu | Ser | Ala | Leu | Ile | Val | Phe | Asn |
| | | | 100 | | | | | 105 | | | | | 110 | | |
| Ile | Gly | Ala | Ile | Leu | Gln | Val | Ile | Ser | Thr | Ala | Ile | Pro | Leu | Leu | Cys |
| | | 115 | | | | | 120 | | | | | 125 | | | |
| Ala | Gly | Arg | Val | Ile | Ala | Gly | Phe | Gly | Val | Gly | Leu | Ile | Ser | Ala | Thr |
| | 130 | | | | | 135 | | | | | 140 | | | | |
| Ile | Pro | Leu | Tyr | Gln | Ser | Glu | Thr | Ala | Pro | Lys | Trp | Ile | Arg | Gly | Ala |
| 145 | | | | | 150 | | | | | 155 | | | | | 160 |
| Ile | Val | Ser | Cys | Tyr | Gln | Trp | Ala | Ile | Thr | Ile | Gly | Leu | Phe | Leu | Ala |
| | | | | 165 | | | | | 170 | | | | | 175 | |
| Ser | Cys | Val | Asn | Lys | Gly | Thr | Glu | His | Met | Thr | Asn | Ser | Gly | Ser | Tyr |
| | | | 180 | | | | | 185 | | | | | 190 | | |
| Arg | Ile | Pro | Leu | Ala | Ile | Gln | Cys | Leu | Trp | Gly | Leu | Ile | Leu | Gly | Ile |
| | | 195 | | | | | 200 | | | | | 205 | | | |
| Gly | Met | Ile | Phe | Leu | Pro | Glu | Thr | Pro | Arg | Phe | Trp | Ile | Ser | Lys | Gly |
| | 210 | | | | | 215 | | | | | 220 | | | | |
| Asn | Gln | Glu | Lys | Ala | Ala | Glu | Ser | Leu | Ala | Arg | Leu | Arg | Lys | Leu | Pro |
| 225 | | | | | 230 | | | | | 235 | | | | | 240 |
| Ile | Asp | His | Pro | Asp | Ser | Leu | Glu | Glu | Leu | Arg | Asp | Ile | Thr | Ala | Ala |
| | | | | 245 | | | | | 250 | | | | | 255 | |
| Tyr | Glu | Phe | Glu | Thr | Val | Tyr | Gly | Lys | Ser | Ser | Trp | Ser | Gln | Val | Phe |
| | | | 260 | | | | | 265 | | | | | 270 | | |
| Ser | His | Lys | Asn | His | Gln | Leu | Lys | Arg | Leu | Phe | Thr | Gly | Val | Ala | Ile |
| | | 275 | | | | | 280 | | | | | 285 | | | |
| Gln | Ala | Phe | Gln | Gln | Leu | Thr | Gly | Val | Asn | Phe | Ile | Phe | Tyr | Tyr | Gly |
| | 290 | | | | | 295 | | | | | 300 | | | | |
| Thr | Thr | Phe | Phe | Lys | Arg | Ala | Gly | Val | Asn | Gly | Phe | Thr | Ile | Ser | Leu |
| 305 | | | | | 310 | | | | | 315 | | | | | 320 |
| Ala | Thr | Asn | Ile | Val | Asn | Val | Gly | Ser | Thr | Ile | Pro | Gly | Ile | Leu | Leu |

|   |   | 325 |   |   |   | 330 |   |   |   | 335 |   |
|---|---|---|---|---|---|---|---|---|---|---|---|

Met Glu Val Leu Gly Arg Arg Asn Met Leu Met Gly Gly Ala Thr Gly
            340                      345                  350

Met Ser Leu Ser Gln Leu Ile Val Ala Ile Val Gly Val Ala Thr Ser
    355                    360                    365

Glu Asn Asn Lys Ser Ser Gln Ser Val Leu Val Ala Phe Ser Cys Ile
   370                    375                  380

Phe Ile Ala Phe Phe Ala Ala Thr Trp Gly Pro Cys Ala Trp Val Val
385                390                    395                400

Val Gly Glu Leu Phe Pro Leu Arg Thr Arg Ala Lys Ser Val Ser Leu
            405                    410                415

Cys Thr Ala Ser Asn Trp Leu Trp Asn Trp Gly Ile Ala Tyr Ala Thr
    420                    425                  430

Pro Tyr Met Val Asp Glu Asp Lys Gly Asn Leu Gly Ser Asn Val Phe
        435                  440                445

Phe Ile Trp Gly Gly Phe Asn Leu Ala Cys Val Phe Phe Ala Trp Tyr
450                455                    460

Phe Ile Tyr Glu Thr Lys Gly Leu Ser Leu Glu Gln Val Asp Glu Leu
465                470                    475                480

Tyr Glu His Val Ser Lys Ala Trp Lys Ser Lys Gly Phe Val Pro Ser
                485                    490                495

Lys His Ser Phe Arg Glu Gln Val Asp Gln Gln Met Asp Ser Lys Thr
        500                  505                510

Glu Ala Ile Met Ser Glu Glu Ala Ser Val
   515                    520

<210> SEQ ID NO 40
<211> LENGTH: 1677
<212> TYPE: DNA
<213> ORGANISM: Arabidopsis thaliana

<400> SEQUENCE: 40

```
atggccttcg cggtctcggt gcagtcccac ttcgccatcc gcgccctgaa gcgcgaccac      60
ttcaagaacc cctcccccg caccttctgc tcctgcttca gtcccgccc cgactcctcc      120
tacctgtcgc tcaaggagcg cacctgcttc gtgtccaagc ccggcctggt gaccacccgc      180
taccgccaca tcttccaggt cggcgcggag accggcggcg acttcgccga ctccggcgag      240
gtcgcggact cgctggcgtc cgacgccccc gagtccttct cctggtcctc cgtgatcctg      300
cccttcatct cccccgcgct gggcggcctg ctgttcggct acgacatcgg cgccacctcg      360
ggcgcgaccc tgtccctgca gtcccccgcg ctgtcgggca ccacctggtt caacttctcg      420
cccgtgcagc tgggcctggt cgtgtccggc tccctgtacg gcgcgctgct gggctcgatc      480
tccgtgtacg gcgtggccga cttcctcggc cgccgccgcg agctgatcat cgccgcggtc      540
ctgtacctcc tgggctccct catcaccggc tgcgcccccg acctgaacat cctgctggtg      600
ggccgcctgc tctacggctt cggcatcggc ctggccatgc acggcgcccc cctgtacatc      660
gccgagacct gcccctccca gatccgcggc accctgatct cgctcaagga gctgttcatc      720
gtgctgggca tctcctgggg cttctcggtg ggctccttcc agatcgacgt ggtgggcggc      780
tggcgctaca tgtacggctt cggcaccccc gtggcgctcc tgatgggcct gggcatgtgg      840
tccctgcccg cgtcgccccg ctggctgctg ctgcgcgcgg tgcagggcaa gggccagctg      900
caggagtaca aggagaaggc gatgctggcc ctgtccaagc tgcgcggccg ccccccgggc      960
gacaagatct ccgagaagct ggtcgacgac gcctacctgt ccgtgaagac cgcctacgag     1020
```

```
gacgagaagt ccggcggcaa cttcctggag gtgttccagg gccccaacct gaaggccctg    1080
accatcggcg ggggcctggt cctgttccag cagatcaccg ccagccctc cgtgctgtac     1140 tacgccggct ccatcctgca gaccgccggc ttctcggcgg ccgccgacgc cacccgcgtg    1200
tccgtgatca tcggcgtgtt caagctgctg atgacctggg tcgcggtcgc caaggtggac    1260
gacctgggcc gccgcccct gctgatcggc ggcgtgtccg gcatcgcgct gtcgctgttc     1320
ctgctgtccg cctactacaa gttcctcggc ggcttccccc tggtggccgt gggcgccctg    1380
ctgctgtacg tgggctgcta ccagatctcc ttcggcccca tctcctggct gatggtgtcc    1440
gagatcttcc cctccgcac ccgcggccgc ggcatctccc tggccgtgct gaccaacttc     1500
ggctccaacg ccatcgtgac cttcgccttc tccccctga aggagttcct gggcgccgag     1560
aacctgttcc tcctgttcgg cggcatcgcc tggtgtcgc tcctgttcgt catcctggtg     1620
gtgcccgaga ccaagggcct ctcgctggag gagatcgagt ccaagatcct gaagtga       1677
```

<210> SEQ ID NO 41
<211> LENGTH: 558
<212> TYPE: PRT
<213> ORGANISM: Arabidopsis thaliana

<400> SEQUENCE: 41

```
Met Ala Phe Ala Val Ser Val Gln Ser His Phe Ala Ile Arg Ala Leu
1               5                   10                  15

Lys Arg Asp His Phe Lys Asn Pro Ser Pro Arg Thr Phe Cys Ser Cys
                20                  25                  30

Phe Lys Ser Arg Pro Asp Ser Tyr Leu Ser Leu Lys Glu Arg Thr
        35                  40                  45

Cys Phe Val Ser Lys Pro Gly Leu Val Thr Thr Arg Tyr Arg His Ile
    50                  55                  60

Phe Gln Val Gly Ala Glu Thr Gly Gly Asp Phe Ala Asp Ser Gly Glu
65                  70                  75                  80

Val Ala Asp Ser Leu Ala Ser Asp Ala Pro Glu Ser Phe Ser Trp Ser
                85                  90                  95

Ser Val Ile Leu Pro Phe Ile Pro Ala Leu Gly Gly Leu Leu Phe
                100                 105                 110

Gly Tyr Asp Ile Gly Ala Thr Ser Gly Ala Thr Leu Ser Leu Gln Ser
            115                 120                 125

Pro Ala Leu Ser Gly Thr Thr Trp Phe Asn Phe Ser Pro Val Gln Leu
    130                 135                 140

Gly Leu Val Val Ser Gly Ser Leu Tyr Gly Ala Leu Leu Gly Ser Ile
145                 150                 155                 160

Ser Val Tyr Gly Val Ala Asp Phe Leu Gly Arg Arg Arg Glu Leu Ile
                165                 170                 175

Ile Ala Ala Val Leu Tyr Leu Leu Gly Ser Leu Ile Thr Gly Cys Ala
                180                 185                 190

Pro Asp Leu Asn Ile Leu Leu Val Gly Arg Leu Leu Tyr Gly Phe Gly
            195                 200                 205

Ile Gly Leu Ala Met His Gly Ala Pro Leu Tyr Ile Ala Glu Thr Cys
    210                 215                 220

Pro Ser Gln Ile Arg Gly Thr Leu Ile Ser Leu Lys Glu Leu Phe Ile
225                 230                 235                 240

Val Leu Gly Ile Leu Leu Gly Phe Ser Val Gly Ser Phe Gln Ile Asp
                245                 250                 255
```

Val Val Gly Gly Trp Arg Tyr Met Tyr Gly Phe Gly Thr Pro Val Ala
            260                 265                 270

Leu Leu Met Gly Leu Gly Met Trp Ser Leu Pro Ala Ser Pro Arg Trp
        275                 280                 285

Leu Leu Leu Arg Ala Val Gln Gly Lys Gly Gln Leu Gln Glu Tyr Lys
    290                 295                 300

Glu Lys Ala Met Leu Ala Leu Ser Lys Leu Arg Gly Arg Pro Pro Gly
305                 310                 315                 320

Asp Lys Ile Ser Glu Lys Leu Val Asp Asp Ala Tyr Leu Ser Val Lys
                325                 330                 335

Thr Ala Tyr Glu Asp Glu Lys Ser Gly Gly Asn Phe Leu Glu Val Phe
            340                 345                 350

Gln Gly Pro Asn Leu Lys Ala Leu Thr Ile Gly Gly Gly Leu Val Leu
        355                 360                 365

Phe Gln Gln Ile Thr Gly Gln Pro Ser Val Leu Tyr Tyr Ala Gly Ser
    370                 375                 380

Ile Leu Gln Thr Ala Gly Phe Ser Ala Ala Ala Asp Ala Thr Arg Val
385                 390                 395                 400

Ser Val Ile Ile Gly Val Phe Lys Leu Leu Met Thr Trp Val Ala Val
                405                 410                 415

Ala Lys Val Asp Asp Leu Gly Arg Arg Pro Leu Leu Ile Gly Gly Val
            420                 425                 430

Ser Gly Ile Ala Leu Ser Leu Phe Leu Leu Ser Ala Tyr Tyr Lys Phe
        435                 440                 445

Leu Gly Gly Phe Pro Leu Val Ala Val Gly Ala Leu Leu Leu Tyr Val
    450                 455                 460

Gly Cys Tyr Gln Ile Ser Phe Gly Pro Ile Ser Trp Leu Met Val Ser
465                 470                 475                 480

Glu Ile Phe Pro Leu Arg Thr Arg Gly Arg Gly Ile Ser Leu Ala Val
                485                 490                 495

Leu Thr Asn Phe Gly Ser Asn Ala Ile Val Thr Phe Ala Phe Ser Pro
            500                 505                 510

Leu Lys Glu Phe Leu Gly Ala Glu Asn Leu Phe Leu Leu Phe Gly Gly
        515                 520                 525

Ile Ala Leu Val Ser Leu Leu Phe Val Ile Leu Val Val Pro Glu Thr
    530                 535                 540

Lys Gly Leu Ser Leu Glu Ile Glu Ser Lys Ile Leu Lys
545                 550                 555

<210> SEQ ID NO 42
<211> LENGTH: 1552
<212> TYPE: DNA
<213> ORGANISM: Trichoderma reesii

<400> SEQUENCE: 42
atgtaccgca tctggaacat ctacgtcctg gcggcgttcg gcaccatcgg cggcatgatc        60
tttggcttcg agatctcgtc gatgtcggcg tggatcggct ccgagcagta cctggagtac       120
ttcaaccacc ccgactccac cgagcagggc ggcatcaccg ccgccatgtc cgccggctcc       180
ctggtgggct ccctgctggc cggctggctg gcggaccgcc tgggccgccg cctggccatc       240
cagatcgcct ccgtggactg gatcgtgggc gcggtcctgc agtgctcgtc gcagaacgtg       300
gcccacctgg tggtgggccg catcgtgtcc ggcctggcga tcggcatcac gtcctcccag       360
tgcatcgtgt acctgtccga gctggccccc tcccgcatcc gcggccgcgt ggtgggcatc       420

```
cagcagtggt ccatcgactg gggcatcctg atcatgtacc tgatctccta cggctgctcc    480
gtgtccatcc accgccccgc cgccttccgc atcgcctggg cctccaggc ggtgcccggc    540
gccgtcctgt tcttctccct cttttcttc cccgagtccc cgcgctggct ggccaccaag    600
gaccgctggg aggagtgcca cgaggtcctg gcgaacctgc acgcgaaggg cgaccgcaac    660
aacatcgagg tgctggccga gctggaggag gtgcgcgagg ccgcgcgcat cgcggccgag    720
tccaaggaga tcggctacct gggcctgttc gcccccaaga gtggaagcg caccctggtc    780
ggcgtctccg cgcagatctg gcagcagctc ctgggcggca acgtgatgct gtactacctg    840
gtgtacatct tcaacatggc cggcatgtcc ggcaacaccg ccctgacctc gtcgatcatc    900
cagtacgtga tcttcctggt gaccaccggc ggcgtgctgt cgtggtgga ccgcatcggc    960
cgccgctggc tgctgatcgt cggcgcgatc atctgcggcg tgatccactt catcgtgggc   1020
gccgtgatgg ccgtctacgg ccaccacgtg gactcggtcg acgcaacga catcctgcgc   1080
tggcagatcg gcggcccccc cgccaaggcc atcatcgccc tgtgctacat cttcgtgggc   1140
gtgtacggcg tgacctgggc ccacggcgcc tggatctact gcggcgaggt gttccccctg   1200
aagtaccgcg ccaagggcgt gggcctggcg gcggccggca actgggcctt caacctggcc   1260
ctggccttct tcgtgccccc cgccttcacc aacatccagt ggaaggccta catgatcttc   1320
ggcacgttct gcatcgccat ggtgtttcac atctacttca gtaccccga ccgtgaag    1380
aagtccctgg aggagatcga cgtcctgttc gagggcgaca tccccgcctg cgctccgcc   1440
tccgccgtgt ccaccttcga cgagaaggtg gcccgcgcga aggaggccgg cggcctggag   1500
gagttctcca gcaggccga catcaagcac gaggagaagg tgtgatacgt ac           1552
```

<210> SEQ ID NO 43
<211> LENGTH: 514
<212> TYPE: PRT
<213> ORGANISM: Trichoderma reesii

<400> SEQUENCE: 43

Met Tyr Arg Ile Trp Asn Ile Tyr Val Leu Ala Ala Phe Gly Thr Ile
1               5                   10                  15

Gly Gly Met Ile Phe Gly Phe Glu Ile Ser Ser Met Ser Ala Trp Ile
            20                  25                  30

Gly Ser Glu Gln Tyr Leu Glu Tyr Phe Asn His Pro Asp Ser Thr Glu
        35                  40                  45

Gln Gly Gly Ile Thr Ala Ala Met Ser Ala Gly Ser Leu Val Gly Ser
    50                  55                  60

Leu Leu Ala Gly Trp Leu Ala Asp Arg Leu Arg Arg Leu Ala Ile
65                  70                  75                  80

Gln Ile Ala Ser Val Asp Trp Ile Val Gly Val Leu Gln Cys Ser
                85                  90                  95

Ser Gln Asn Val Ala His Leu Val Val Gly Arg Ile Val Ser Gly Leu
            100                 105                 110

Ala Ile Gly Ile Thr Ser Ser Gln Cys Ile Val Tyr Leu Ser Glu Leu
        115                 120                 125

Ala Pro Ser Arg Ile Arg Gly Arg Val Val Gly Ile Gln Gln Trp Ser
    130                 135                 140

Ile Asp Trp Gly Ile Leu Ile Met Tyr Leu Ile Ser Tyr Gly Cys Ser
145                 150                 155                 160

Val Ser Ile His Arg Pro Ala Ala Phe Arg Ile Ala Trp Gly Leu Gln
                165                 170                 175

```
Ala Val Pro Gly Ala Val Leu Phe Phe Ser Leu Phe Phe Phe Pro Glu
                180                 185                 190

Ser Pro Arg Trp Leu Ala Thr Lys Asp Arg Trp Glu Glu Cys His Glu
            195                 200                 205

Val Leu Ala Asn Leu His Ala Lys Gly Asp Arg Asn Asn Ile Glu Val
        210                 215                 220

Leu Ala Glu Leu Glu Glu Val Arg Glu Ala Ala Arg Ile Ala Ala Glu
225                 230                 235                 240

Ser Lys Glu Ile Gly Tyr Leu Gly Leu Phe Ala Pro Lys Met Trp Lys
                245                 250                 255

Arg Thr Leu Val Gly Val Ser Ala Gln Ile Trp Gln Gln Leu Leu Gly
            260                 265                 270

Gly Asn Val Met Leu Tyr Tyr Leu Val Tyr Ile Phe Asn Met Ala Gly
        275                 280                 285

Met Ser Gly Asn Thr Ala Leu Thr Ser Ser Ile Ile Gln Tyr Val Ile
290                 295                 300

Phe Leu Val Thr Thr Gly Gly Val Leu Phe Val Val Asp Arg Ile Gly
305                 310                 315                 320

Arg Arg Trp Leu Leu Ile Val Gly Ala Ile Ile Cys Gly Val Ile His
                325                 330                 335

Phe Ile Val Gly Ala Val Met Ala Val Tyr Gly His His Val Asp Ser
            340                 345                 350

Val Asp Gly Asn Asp Ile Leu Arg Trp Gln Ile Gly Pro Pro Ala
        355                 360                 365

Lys Ala Ile Ile Ala Leu Cys Tyr Ile Phe Val Gly Val Tyr Gly Val
                370                 375                 380

Thr Trp Ala His Gly Ala Trp Ile Tyr Cys Gly Glu Val Phe Pro Leu
385                 390                 395                 400

Lys Tyr Arg Ala Lys Gly Val Gly Leu Ala Ala Ala Gly Asn Trp Ala
                405                 410                 415

Phe Asn Leu Ala Leu Ala Phe Phe Val Pro Pro Ala Phe Thr Asn Ile
            420                 425                 430

Gln Trp Lys Ala Tyr Met Ile Phe Gly Thr Phe Cys Ile Ala Met Val
        435                 440                 445

Phe His Ile Tyr Phe Met Tyr Pro Glu Thr Val Lys Lys Ser Leu Glu
450                 455                 460

Glu Ile Asp Val Leu Phe Glu Gly Asp Ile Pro Ala Trp Arg Ser Ala
465                 470                 475                 480

Ser Ala Val Ser Thr Phe Asp Glu Lys Val Ala Arg Ala Lys Glu Ala
                485                 490                 495

Gly Gly Leu Glu Glu Phe Ser Lys Gln Ala Asp Ile Lys His Glu Glu
            500                 505                 510

Lys Val

<210> SEQ ID NO 44
<211> LENGTH: 1189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atgagggtgg agatctggag aactgggtcg cctcatgccg cgcagggggg attgtgctgg      60
catgtgagtg atttgggtgc ggcgacgcac cgggagagcg agcccagccg aggcggtact     120
```

```
ttgttccgcg ggcccgccct cacgccccgc ccacccgcat gcatccgcga cctgcgcagg      180
ggccgtgggc tcctccgact cgaaccccga cgagaagtcc gacctgggcg aggccgagaa      240
gaaggagaag aaggccaaga ccctgcagct gggcatcgtg ttcggcctgt ggtacttcca      300
gaacatcgtc ttcaacatct tcaacaagaa ggccctgaac gtgttcccct accccctggct     360 cctggcctcc ttccagctgt tcgccggctc catctggatg ctggtgctgt ggtcgttcaa      420
gctgtacccc tgcccaaga tctcgaagcc gttcatcatc gcgctgctgg ccccgccct       480 gttccacacc atcggccaca tctccgcctg cgtgtccttc tccaaggtgg ccgtctcgtt      540
cacccacgtg atcaagtccg ccgagcccgt gttctccgtg atcttctcct cgctgctggg     600
cgactcctac cccctggccg tgtggctgtc catcctgccc atcgtgatgg gctgctccct      660
ggccgccgtg accgaggtct cgttcaacct gggcggcctg tccggcgcca tgatctccaa      720
cgtgggcttc gtgctgcgca acatctactc caagcgctcc ctgcagtcct tcaaggagat      780
cgacggcctc aacctgtacg gctgcatctc catcctgtcc ctgctgtacc tgttccccgt      840
ggccatcttc gtggagggct cccactgggt gcccggctac cacaaggcca tcgcctccgt      900
gggcaccccc tccaccttct acttctgggt ctggctgtcg ggcgtgttct accacctgta      960
caaccagtcc tcctaccagg ccctggacga gatctccccc ctgaccttct cggtcggcaa     1020
caccatgaag cgcgtggtgg tgatcatctc caccgtgctg gtgttccgca accccgtgcg     1080
ccccctgaac gccctgggct ccgccatcgc catctgcggc accttcctgt actcccaggc     1140
caccgccaag aagaagaaga tcgaggtggg cggcgacaag aagaactga               1189
```

<210> SEQ ID NO 45
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Met Arg Val Glu Ile Trp Arg Thr Gly Ser Pro His Ala Ala Gln Gly
1               5                   10                  15

Gly Leu Cys Trp His Val Ser Asp Leu Gly Ala Ala Thr His Arg Glu
            20                  25                  30

Ser Glu Pro Ser Arg Gly Gly Thr Leu Phe Arg Gly Pro Ala Leu Thr
        35                  40                  45

Pro Arg Pro Pro Ala Cys Ile Arg Asp Leu Arg Gly Arg Gly Leu
    50                  55                  60

Leu Arg Leu Glu Pro Arg Arg Glu Val Arg Pro Gly Arg Gly Arg Glu
65                  70                  75                  80

Glu Gly Glu Glu Gly Gln Asp Pro Ala Ala Gly His Arg Val Arg Pro
                85                  90                  95

Val Val Leu Pro Glu His Arg Leu Gln His Leu Gln Gln Glu Gly Pro
            100                 105                 110

Glu Arg Val Pro Leu Pro Leu Ala Pro Gly Leu Leu Pro Ala Val Arg
        115                 120                 125

Arg Leu His Leu Asp Ala Gly Ala Val Val Gln Ala Val Pro Leu
    130                 135                 140

Pro Gln Asp Leu Glu Ala Val His His Arg Ala Ala Gly Pro Arg Pro
145                 150                 155                 160

Val Pro His His Arg Pro His Leu Arg Leu Arg Val Leu Leu Gln Gly
```

```
                165                 170                 175
Gly Arg Leu Val His Pro Arg Asp Gln Val Arg Arg Ala Arg Val Leu
            180                 185                 190
Arg Asp Leu Leu Leu Ala Ala Gly Arg Leu Leu Pro Pro Gly Arg Val
        195                 200                 205
Ala Val His Pro Ala His Arg Asp Gly Leu Leu Pro Gly Arg Arg Asp
    210                 215                 220
Arg Gly Leu Val Gln Pro Gly Arg Pro Val Arg His Asp Leu Gln
225                 230                 235                 240
Arg Gly Leu Arg Ala Ala Gln His Leu Leu Gln Ala Leu Pro Ala Val
                245                 250                 255
Leu Gln Gly Asp Arg Arg Pro Gln Pro Val Arg Leu His Leu His Pro
            260                 265                 270
Val Pro Ala Val Pro Val Pro Arg Gly His Leu Arg Gly Leu Pro
        275                 280                 285
Leu Gly Ala Arg Leu Pro Gln Gly His Arg Leu Arg Gly His Pro Leu
    290                 295                 300
His Leu Leu Leu Gly Leu Ala Val Gly Arg Val Leu Pro Pro Val
305                 310                 315                 320
Gln Pro Val Leu Leu Pro Gly Pro Gly Arg Asp Leu Pro Pro Asp Leu
                325                 330                 335
Leu Gly Arg Gln His His Glu Ala Arg Gly Gly Asp His Leu His Arg
            340                 345                 350
Ala Gly Val Pro Gln Pro Arg Ala Pro Pro Glu Arg Pro Gly Leu Arg
        355                 360                 365
His Arg His Leu Arg His Leu Pro Val Leu Pro Gly His Arg Gln Glu
    370                 375                 380
Glu Glu Asp Arg Gly Gly Arg Arg Gln Glu Glu Leu
385                 390                 395

<210> SEQ ID NO 46
<211> LENGTH: 1189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atgagggtgg agatctggag aactgggtcg ccttatgccg tgccggaggg cttgtactgg      60
gttgagagtg atttgggtgc ggcgacgcac cgggagagcg agcccagccg aggcggtact     120
ttgctccgcg ggcccgccct cacgccccgc ccacccgcat gcatccgcga cctgcgcagg     180
ggccgtgggc tcctccgact cgaaccccga cgagaagtcc gacctgggcg aggccgagaa     240
gaaggagaag aaggccaaga ccctgcagct gggcatcgtg ttcggcctgt ggtacttcca     300
gaacatcgtc ttcaacatct tcaacaagaa ggccctgaac gtgttcccct accctggct      360 cctggcctcc ttccagctgt tcgccggctc catctggatg ctggtgctgt ggtcgttcaa     420
gctgtacccc tgccccaaga tctcgaagcc gttcatcatc gcgctgctgg gccccgccct     480
gttccacacc atcggccaca tctccgcctg cgtgtccttc ccaaggtggg ccgtctcgtt     540
cacccacgtg atcaagtccg ccgagcccgt gttctccgtg atcttctcct cgctgctggg     600
cgactcctac cccctggccg tgtggctgtc catcctgccc atcgtgatgg gctgctcct      660 ggccgccgtg accgaggtct cgttcaacct gggcggcctg tccggcgcca tgatctccaa     720
```

```
cgtgggcttc gtgctgcgca acatctactc caagcgctcc ctgcagtcct tcaaggagat    780
cgacggcctc aacctgtacg gctgcatctc catcctgtcc ctgctgtacc tgttccccgt    840
ggccatcttc gtggagggct cccactgggt gcccggctac acaaggcca tcgcctccgt    900 gggcacccc tccaccttct acttctgggt ctggctgtcg ggcgtgttct accacctgta    960
caaccagtcc tcctaccagg ccctggacga gatctccccc ctgaccttct cggtcggcaa   1020
caccatgaag cgcgtggtgg tgatcatctc caccgtgctg gtgttccgca acccgtgcg   1080 cccctgaac gccctgggct ccgccatcgc catctgcggc accttcctgt actcccaggc   1140
caccgccaag aagaagaaga tcgaggtggg cggcgacaag aagaactga              1189
```

<210> SEQ ID NO 47
<211> LENGTH: 396
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Met Arg Val Glu Ile Trp Arg Thr Gly Ser Pro Tyr Ala Val Pro Glu
1               5                   10                  15

Gly Leu Tyr Trp Val Glu Ser Asp Leu Gly Ala Ala Thr His Arg Glu
            20                  25                  30

Ser Glu Pro Ser Arg Gly Gly Thr Leu Leu Arg Gly Pro Ala Leu Thr
        35                  40                  45

Pro Arg Pro Pro Ala Cys Ile Arg Asp Leu Arg Arg Gly Arg Gly Leu
    50                  55                  60

Leu Arg Leu Glu Pro Arg Arg Glu Val Arg Pro Gly Arg Gly Arg Glu
65                  70                  75                  80

Glu Gly Glu Glu Gly Gln Asp Pro Ala Ala Gly His Arg Val Arg Pro
                85                  90                  95

Val Val Leu Pro Glu His Arg Leu Gln His Leu Gln Gln Glu Gly Pro
            100                 105                 110

Glu Arg Val Pro Leu Pro Leu Ala Pro Gly Leu Leu Pro Ala Val Arg
        115                 120                 125

Arg Leu His Leu Asp Ala Gly Ala Val Val Val Gln Ala Val Pro Leu
    130                 135                 140

Pro Gln Asp Leu Glu Ala Val His Arg Ala Ala Gly Pro Arg Pro
145                 150                 155                 160

Val Pro His His Arg Pro His Leu Arg Leu Arg Val Leu Leu Gln Gly
                165                 170                 175

Gly Arg Leu Val His Pro Arg Asp Gln Val Arg Arg Ala Arg Val Leu
            180                 185                 190

Arg Asp Leu Leu Leu Ala Ala Gly Arg Leu Leu Pro Pro Gly Arg Val
        195                 200                 205

Ala Val His Pro Ala His Arg Asp Gly Leu Leu Pro Gly Arg Arg Asp
    210                 215                 220

Arg Gly Leu Val Gln Pro Gly Arg Pro Val Arg His Asp Leu Gln
225                 230                 235                 240

Arg Gly Leu Arg Ala Ala Gln His Leu Leu Gln Ala Leu Pro Ala Val
                245                 250                 255

Leu Gln Gly Asp Arg Arg Pro Gln Pro Val Arg Leu His Leu His Pro
            260                 265                 270

Val Pro Ala Val Pro Val Pro Arg Gly His Leu Arg Gly Gly Leu Pro
```

```
                275                 280                 285
Leu Gly Ala Arg Leu Pro Gln Gly His Arg Leu Arg Gly His Pro Leu
        290                 295                 300

His Leu Leu Leu Leu Gly Leu Ala Val Gly Arg Val Leu Pro Pro Val
305                 310                 315                 320

Gln Pro Val Leu Leu Pro Gly Pro Gly Arg Asp Leu Pro Pro Asp Leu
                325                 330                 335

Leu Gly Arg Gln His His Glu Ala Arg Gly Gly Asp His Leu His Arg
                340                 345                 350

Ala Gly Val Pro Gln Pro Arg Ala Pro Pro Glu Arg Pro Gly Leu Arg
                355                 360                 365

His Arg His Leu Arg His Leu Pro Val Leu Pro Gly His Arg Gln Glu
            370                 375                 380

Glu Glu Asp Arg Gly Gly Arg Arg Gln Glu Glu Leu
385                 390                 395

<210> SEQ ID NO 48
<211> LENGTH: 1114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atggccaccg catccacttt ctcggcgttc aatgcccgct gcggcgacct gcgtcgctcg      60
gcgggctccg ggccccggcg cccagcgagg cccctcccg tgcgcggccg tgggctcctc     120
cgactcgaac cccgacgaga agtccgacct gggcgaggcc gagaagaagg agaagaaggc     180
caagaccctg cagctgggca tcgtgttcgg cctgtggtac ttccagaaca tcgtcttcaa     240
catcttcaac aagaaggccc tgaacgtgtt ccctacccc tggctcctgg cctccttcca     300
gctgttcgcc ggctccatct ggatgctggt gctgtggtcg ttcaagctgt accctgccc     360 caagatctcg aagccgttca tcatcgcgct gctgggcccc gccctgttcc acaccatcgg     420
ccacatctcc gcctgcgtgt ccttctccaa ggtggccgtc tcgttcaccc acgtgatcaa     480
gtccgccgag cccgtgttct ccgtgatctt ctcctcgctg ctgggcgact cctacccct     540 ggccgtgtgg ctgtccatcc tgcccatcgt gatgggctgc tccctggccg ccgtgaccga     600
ggtctcgttc aacctgggcg gcctgtccgg cgccatgatc tccaacgtgg gcttcgtgct     660
gcgcaacatc tactccaagc gctccctgca gtccttcaag gagatcgacg gcctcaacct     720
gtacggctgc atctccatcc tgtccctgct gtacctgttc cccgtggcca tcttcgtgga     780
gggctcccac tgggtgcccg gctaccacaa ggccatcgcc tccgtgggca ccccctccac     840
cttctacttc tgggtctggc tgtcgggcgt gttctaccac ctgtacaacc agtcctccta     900
ccaggccctg gacagagatct ccccctgac cttctcggtc ggcaacacca tgaagcgcgt     960
ggtggtgatc atctccaccg tgctggtgtt ccgcaacccc gtgcgccccc tgaacgccct    1020
gggctccgcc atcgccatct gcggcacctt cctgtactcc caggccaccg ccaagaagaa    1080
gaagatcgag gtgggcggcg acaagaagaa ctga                                1114

<210> SEQ ID NO 49
<211> LENGTH: 371
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 49

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Gly Leu Leu Arg Leu Glu Pro Arg Arg Glu Val
        35                  40                  45

Arg Pro Gly Arg Gly Arg Glu Glu Gly Glu Glu Gly Gln Asp Pro Ala
    50                  55                  60

Ala Gly His Arg Val Arg Pro Val Val Leu Pro Glu His Arg Leu Gln
65                  70                  75                  80

His Leu Gln Gln Glu Gly Pro Glu Arg Val Pro Leu Pro Leu Ala Pro
                85                  90                  95

Gly Leu Leu Pro Ala Val Arg Arg Leu His Leu Asp Ala Gly Ala Val
            100                 105                 110

Val Val Gln Ala Val Pro Leu Pro Gln Asp Leu Glu Ala Val His His
        115                 120                 125

Arg Ala Ala Gly Pro Arg Pro Val Pro His His Arg Pro His Leu Arg
    130                 135                 140

Leu Arg Val Leu Leu Gln Gly Gly Arg Leu Val His Pro Arg Asp Gln
145                 150                 155                 160

Val Arg Arg Ala Arg Val Leu Arg Asp Leu Leu Ala Ala Gly Arg
                165                 170                 175

Leu Leu Pro Pro Gly Arg Val Ala Val His Pro Ala His Arg Asp Gly
            180                 185                 190

Leu Leu Pro Gly Arg Arg Asp Arg Gly Leu Val Gln Pro Gly Arg Pro
        195                 200                 205

Val Arg Arg His Asp Leu Gln Arg Gly Leu Arg Ala Ala Gln His Leu
    210                 215                 220

Leu Gln Ala Leu Pro Ala Val Leu Gln Gly Asp Arg Arg Pro Gln Pro
225                 230                 235                 240

Val Arg Leu His Leu His Pro Val Pro Ala Val Pro Val Pro Arg Gly
                245                 250                 255

His Leu Arg Gly Gly Leu Pro Leu Gly Ala Arg Leu Pro Gln Gly His
            260                 265                 270

Arg Leu Arg Gly His Pro Leu His Leu Leu Leu Gly Leu Ala Val
        275                 280                 285

Gly Arg Val Leu Pro Pro Val Gln Pro Val Leu Leu Pro Gly Pro Gly
    290                 295                 300

Arg Asp Leu Pro Pro Asp Leu Leu Gly Arg Gln His His Glu Ala Arg
305                 310                 315                 320

Gly Gly Asp His Leu His Arg Ala Gly Val Pro Gln Pro Arg Ala Pro
                325                 330                 335

Pro Glu Arg Pro Gly Leu Arg His His Leu Arg His Leu Pro Val
            340                 345                 350

Leu Pro Gly His Arg Gln Glu Glu Glu Asp Arg Gly Gly Arg Arg Gln
        355                 360                 365

Glu Glu Leu
    370
```

<210> SEQ ID NO 50
<211> LENGTH: 363

```
<212> TYPE: PRT
<213> ORGANISM: Pichia stipitis

<400> SEQUENCE: 50

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360

<210> SEQ ID NO 51
<211> LENGTH: 623
<212> TYPE: PRT
<213> ORGANISM: Pichia stipitis
```

<400> SEQUENCE: 51

```
Met Thr Thr Thr Pro Phe Asp Ala Pro Asp Lys Leu Phe Leu Gly Phe
1               5                   10                  15

Asp Leu Ser Thr Gln Gln Leu Lys Ile Ile Val Thr Asp Glu Asn Leu
            20                  25                  30

Ala Ala Leu Lys Thr Tyr Asn Val Glu Phe Asp Ser Ile Asn Ser Ser
            35                  40                  45

Val Gln Lys Gly Val Ile Ala Ile Asn Asp Glu Ile Ser Lys Gly Ala
        50                  55                  60

Ile Ile Ser Pro Val Tyr Met Trp Leu Asp Ala Leu Asp His Val Phe
65                  70                  75                  80

Glu Asp Met Lys Lys Asp Gly Phe Pro Phe Asn Lys Val Val Gly Ile
                85                  90                  95

Ser Gly Ser Cys Gln Gln His Gly Ser Val Tyr Trp Ser Arg Thr Ala
            100                 105                 110

Glu Lys Val Leu Ser Glu Leu Asp Ala Glu Ser Ser Leu Ser Ser Gln
            115                 120                 125

Met Arg Ser Ala Phe Thr Phe Lys His Ala Pro Asn Trp Gln Asp His
130                 135                 140

Ser Thr Gly Lys Glu Leu Glu Glu Phe Glu Arg Val Ile Gly Ala Asp
145                 150                 155                 160

Ala Leu Ala Asp Ile Ser Gly Ser Arg Ala His Tyr Arg Phe Thr Gly
                165                 170                 175

Leu Gln Ile Arg Lys Leu Ser Thr Arg Phe Lys Pro Glu Lys Tyr Asn
            180                 185                 190

Arg Thr Ala Arg Ile Ser Leu Val Ser Ser Phe Val Ala Ser Val Leu
        195                 200                 205

Leu Gly Arg Ile Thr Ser Ile Glu Glu Ala Asp Ala Cys Gly Met Asn
210                 215                 220

Leu Tyr Asp Ile Glu Lys Arg Glu Phe Asn Glu Leu Leu Ala Ile
225                 230                 235                 240

Ala Ala Gly Val His Pro Glu Leu Asp Gly Val Glu Gln Asp Gly Glu
                245                 250                 255

Ile Tyr Arg Ala Gly Ile Asn Glu Leu Lys Arg Lys Leu Gly Pro Val
            260                 265                 270

Lys Pro Ile Thr Tyr Glu Ser Glu Gly Asp Ile Ala Ser Tyr Phe Val
        275                 280                 285

Thr Arg Tyr Gly Phe Asn Pro Asp Cys Lys Ile Tyr Ser Phe Thr Gly
290                 295                 300

Asp Asn Leu Ala Thr Ile Ile Ser Leu Pro Leu Ala Pro Asn Asp Ala
305                 310                 315                 320

Leu Ile Ser Leu Gly Thr Ser Thr Thr Val Leu Ile Ile Thr Lys Asn
                325                 330                 335

Tyr Ala Pro Ser Ser Gln Tyr His Leu Phe Lys His Pro Thr Met Pro
            340                 345                 350

Asp His Tyr Met Gly Met Ile Cys Tyr Cys Asn Gly Ser Leu Ala Arg
        355                 360                 365

Glu Lys Val Arg Asp Glu Val Asn Glu Lys Phe Asn Val Glu Asp Lys
            370                 375                 380

Lys Ser Trp Asp Lys Phe Asn Glu Ile Leu Asp Lys Ser Thr Asp Phe
385                 390                 395                 400

Asn Asn Lys Leu Gly Ile Tyr Phe Pro Leu Gly Glu Ile Val Pro Asn
```

```
                        405                 410                 415
Ala Ala Ala Gln Ile Lys Arg Ser Val Leu Asn Ser Lys Asn Glu Ile
            420                 425                 430

Val Asp Val Glu Leu Gly Asp Lys Asn Trp Gln Pro Glu Asp Asp Val
        435                 440                 445

Ser Ser Ile Val Glu Ser Gln Thr Leu Ser Cys Arg Leu Arg Thr Gly
    450                 455                 460

Pro Met Leu Ser Lys Ser Gly Asp Ser Ser Ala Ser Ser Ser Ala Ser
465                 470                 475                 480

Pro Gln Pro Glu Gly Asp Gly Thr Asp Leu His Lys Val Tyr Gln Asp
                485                 490                 495

Leu Val Lys Lys Phe Gly Asp Leu Tyr Thr Asp Gly Lys Lys Gln Thr
            500                 505                 510

Phe Glu Ser Leu Thr Ala Arg Pro Asn Arg Cys Tyr Tyr Val Gly Gly
        515                 520                 525

Ala Ser Asn Asn Gly Ser Ile Ile Arg Lys Met Gly Ser Ile Leu Ala
    530                 535                 540

Pro Val Asn Gly Asn Tyr Lys Val Asp Ile Pro Asn Ala Cys Ala Leu
545                 550                 555                 560

Gly Gly Ala Tyr Lys Ala Ser Trp Ser Tyr Glu Cys Glu Ala Lys Lys
                565                 570                 575

Glu Trp Ile Gly Tyr Asp Gln Tyr Ile Asn Arg Leu Phe Glu Val Ser
            580                 585                 590

Asp Glu Met Asn Ser Phe Glu Val Lys Asp Lys Trp Leu Glu Tyr Ala
        595                 600                 605

Asn Gly Val Gly Met Leu Ala Lys Met Glu Ser Glu Leu Lys His
    610                 615                 620

<210> SEQ ID NO 52
<211> LENGTH: 4
<212> TYPE: PRT
<213> ORGANISM: Unknown
<220> FEATURE:
<223> OTHER INFORMATION: Description of Unknown: Retention
      signal peptide

<400> SEQUENCE: 52

Lys Asp Glu Leu
1
```